(12) United States Patent
Tomaney et al.

(10) Patent No.: US 8,182,993 B2
(45) Date of Patent: May 22, 2012

(54) METHODS AND PROCESSES FOR CALLING BASES IN SEQUENCE BY INCORPORATION METHODS

(75) Inventors: Austin B. Tomaney, San Francisco, CA (US); Kenneth Mark Maxham, Redwood City, CA (US); David Holden, Burlingame, CA (US); Kevin Hester, Belmont, CA (US); Devon Murphy, Mountain View, CA (US); Patrick Marks, San Francisco, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 452 days.

(21) Appl. No.: 12/134,186

(22) Filed: Jun. 5, 2008

(65) Prior Publication Data
US 2009/0024331 A1    Jan. 22, 2009

Related U.S. Application Data

(60) Provisional application No. 60/933,399, filed on Jun. 6, 2007.

(51) Int. Cl.
C12Q 1/68 (2006.01)
C12P 19/34 (2006.01)
C07H 21/04 (2006.01)
(52) U.S. Cl. .................. 435/6.12; 435/91.2; 536/24.33
(58) Field of Classification Search ............. 435/6, 91; 536/23.1, 24.33
See application file for complete search history.

(56) References Cited

U.S. PATENT DOCUMENTS

| | | | |
|---|---|---|---|
| 2003/0044781 A1* | 3/2003 | Korlach et al. | 435/6 |
| 2003/0064366 A1 | 4/2003 | Hardin et al. | |
| 2003/0096302 A1 | 5/2003 | Yguerabide et al. | |
| 2004/0009586 A1 | 1/2004 | Oldham et al. | |
| 2005/0233363 A1 | 10/2005 | Hardin et al. | |
| 2006/0014151 A1 | 1/2006 | Ogura et al. | |
| 2006/0019267 A1* | 1/2006 | Quake | 435/6 |
| 2006/0063264 A1 | 3/2006 | Turner et al. | |
| 2007/0036511 A1 | 2/2007 | Lundquist et al. | |
| 2008/0293071 A1* | 11/2008 | Gelfand et al. | 435/6 |

OTHER PUBLICATIONS

Friedman (Feb. 24, 1999) "Greedy Function Approximation: A Gradient Boosting Machine," Technical Report, Dept. of Statistics, Stanford University, p. 1-39.
Friedman (Mar. 26, 1999) "Stochastic Gradient Boosting," Technical Report, Dept. of Statistics, Stanford University, p. 1-10.
Lafferty, et al. (2001) "Conditional Random Fields: Probabilistic Models for Segmenting and Labeling Sequence Data," Proc. Int'l Conf Machine Learning 2001, p. 282-289.
Parker, et al. (2006) "Gradient Boosting for Sequence Alignment," Proceedings of the 21st National Conference on Artificial Intelligence, pp. 452-457.
International Search Report and Written Opinion dated Sep. 11, 2008 for related case PCT/US2008/065996.
International Preliminary Report on Patentability dated Dec. 17, 2009 for related case PCT/US2008/065996.

* cited by examiner

*Primary Examiner* — Prabha Chunduru
(74) *Attorney, Agent, or Firm* — Morgan, Lewis & Bockius LLP

(57) ABSTRACT

Computer implemented methods, and systems performing such methods for processing signal data from analytical operations and systems, and particularly in processing signal data from sequence-by-incorporation processes to identify nucleotide sequences of template nucleic acids and larger nucleic acid molecules, e.g., genomes or fragments thereof.

52 Claims, 37 Drawing Sheets

| START: CALCULATE AND STORE OR UTILIZE PULSE METRICS |
|---|

↓ L1

| for each detected pulse in a dye trace for a ZMW and/or for each pulse mapped to captured pixel data determine one or more pulse metrics:<br>   t1 – Pulse Arrival;<br>   dt – Pulse Width;<br>   ds - Pulse spacing;<br>   Signal – integrated counts*;<br>   Peak – Pulse height;<br>   SNR of total pulse signal;<br>   PNR – statistical significance of pulse amplitude;<br>   PDR – pulse to diffusion BG ratio;<br>   minChi2 – spectral fit Chi2 of best fit dye;<br>   minDeltaChi2 – difference of lowest pair of Chi2 values (spectral separation metric);<br>   Sharpness – concentration of flux in one pixel, which can indicate cosmic ray or clock-induced-charge;<br>   DYEfraction – fraction of classified base dye that describes pulse spectrum (spectral overlap/spectral shift);<br>   xcen, xcenDYE, DYEshift – xcorr centroid of spectrum (spectral shift metrics);<br>   BASE – base assignment |
|---|

↓ L2

| for each dye trace for a ZMW determine one or more trace metrics:<br>   Baseline and sigma in all channels<br>   Pulse statistics<br>   Waviness score<br>   Read length<br>   Alignment, Classifier scores etc |
|---|

↓ L3

| use one or more pulse metrics and/or trace metrics in confirming |
|---|

↓ L4

| optionally, store one or more pulse metrics and/or trace metrics along with base call for later analysis |
|---|

*FIGURE 34*

METHODS AND PROCESSES FOR CALLING BASES IN SEQUENCE BY INCORPORATION METHODS

CROSS REFERENCE TO RELATED APPLICATIONS

This application claims priority from provisional patent application 60/933,399 filed 6 Jun. 2007 and incorporated herein by reference.

STATEMENT REGARDING FEDERALLY SPONSORED RESEARCH

Not Applicable.

BACKGROUND OF THE INVENTION

Analysis of the subtleties of the voluminous amounts of genetic information will continue to have profound effects on the personalization of medicine. For example, this advanced genetic knowledge of patients has and will continue to have broad impact on the ability to diagnose diseases, identify predispositions to diseases or other genetically impacted disorders, the ability to identify reactivity to given drugs or other treatments, whether adverse or beneficial.

Before one can begin to interpret genetic data from patients, one must first obtain the genetic information from that patient. Technologies have been developed that allow for broad screening of large swaths of a patient's genetic code by identifying key signposts in that code and using this fragmented data as a general interpretation mechanism, e.g., using libraries of known genetic variations, such as SNPs or other polymorphisms, and correlating the profile of such variations against profiles that have a suspected association with a given disease or other phenotype.

Rather than rely upon disparate pieces of information from the genetic code, it would be of far more value to be able to rely upon the entire text of a patient's genetic code in making any interpretations from that code. In using an analogy of a novel, one gains a substantially deeper understanding of all the elements of the novel, e.g., plot, characters, setting etc., by reading the entire text, rather than by picking out individual words from disparate pages or chapters of the novel.

Technologies related to analysis of biological information have advanced rapidly over the past decade. In particular, with the improved ability to characterize genetic sequence information, identify protein structure, elucidate biological pathways, and manipulate any or all of these, has come the need for improved abilities to derive and process this information.

In the field of genetic analysis, for example, faster and faster methods of obtaining nucleic acid sequence information have consequences in terms of requiring different and often times better methods and processes for processing the raw genetic information that is generated by these processes. This progress has been evidenced in the improvements applied to separations based Sanger sequencing, where improvements in throughput and read-length have come not only through multiplexing of multi-capillary systems, but also from improvements in base calling processes that are applied to the data derived from the capillary systems.

With shifts in the underlying technology surrounding genetic analysis, also comes a necessity for a shift in the methods and processes for processing the information from these systems. The present invention provides solutions to these and other problems.

Various embodiments and components of the present invention employ pulse, signal, and data analysis techniques that are familiar in a number of technical fields. For clarity of description, details of known techniques are not provided herein. These techniques are discussed in a number of available references works, such as: R. B. Ash. Real Analysis and Probability. Academic Press, New York, 1972; D. T. Bertsekas and J. N. Tsitsiklis. Introduction to Probability. 2002; K. L. Chung. Markov Chains with Stationary Transition Probabilities, 1967; W. B. Davenport and W. L Root. An Introduction to the Theory of Random Signals and Noise. McGraw-Hill, New York, 1958; S. M. Kay, Fundamentals of Statistical Processing, Vols. 1-2, (Hardcover—1998); Monsoon H. Hayes, Statistical Digital Signal Processing and Modeling, 1996; Introduction to Statistical Signal Processing by R. M. Gray and L. D. Davisson; Modern Spectral Estimation: Theory and Application/Book and Disk (Prentice-Hall Signal Processing Series) by Steven M. Kay (Hardcover—January 1988); Modern Spectral Estimation: Theory and Application by Steven M. Kay (Paperback—March 1999); Spectral Analysis and Filter Theory in Applied Geophysics by Burkhard Buttkus (Hardcover—May 11, 2000); Spectral Analysis for Physical Applications by Donald B. Percival and Andrew T. Walden (Paperback—Jun. 25, 1993); Astronomical Image and Data Analysis (Astronomy and Astrophysics Library) by J.-L. Starck and F. Murtagh (Hardcover—Sep. 25, 2006); Spectral Techniques In Proteomics by Daniel S. Sem (Hardcover—Mar. 30, 2007); Exploration and Analysis of DNA Microarray and Protein Array Data (Wiley Series in Probability and Statistics) by Dhammika Amaratunga and Javier Cabrera (Hardcover—Oct. 21, 2003).

BRIEF SUMMARY OF THE INVENTION

The invention is generally directed to processes, and particularly computer implemented processes for analyzing fluorescent signals from sequence by incorporation systems, and for ultimately identifying sequence information of a target nucleic acid sequence. Consequently, the invention is also directed to systems that carry out these processes.

The invention and various specific aspects and embodiments will be better understood with reference to the following drawings and detailed descriptions. In different figures, similarly numbered items are intended to represent similar functions within the scope of the teachings provided herein. In some of the drawings and detailed descriptions below, the present invention is described in terms of the important independent embodiment of a system operating on a logic processing device, such as a computer system. This should not be taken to limit the invention, which, using the teachings provided herein, can be applied to any number of logic processors working together, whether incorporated into a camera, a detector, other optical components, or other information enabled devices or logic components incorporated into laboratory or diagnostic equipment or in functional communication therewith. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims.

Furthermore, it is well known in the art that logic systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification. The functional aspects of the invention that are implemented on a computer or other logic processing systems or circuits, as will be understood from the teachings herein, may be implemented or accomplished using any appropriate implementation environment or programming language, such as C, C++, Cobol, Pascal, Java, Java-script, HTML, XML, dHTML, assembly or machine code programming, RTL, etc. All references, publications, patents, and patent applications cited herein are hereby incorporated by reference in their entirety for all purposes.

BRIEF DESCRIPTION OF THE DRAWINGS

FIG. 34 is a flow chart illustrating an example method of determining pulse metrics according to specific embodiments of the invention.

DETAILED DESCRIPTION OF THE INVENTION

Figure 1:
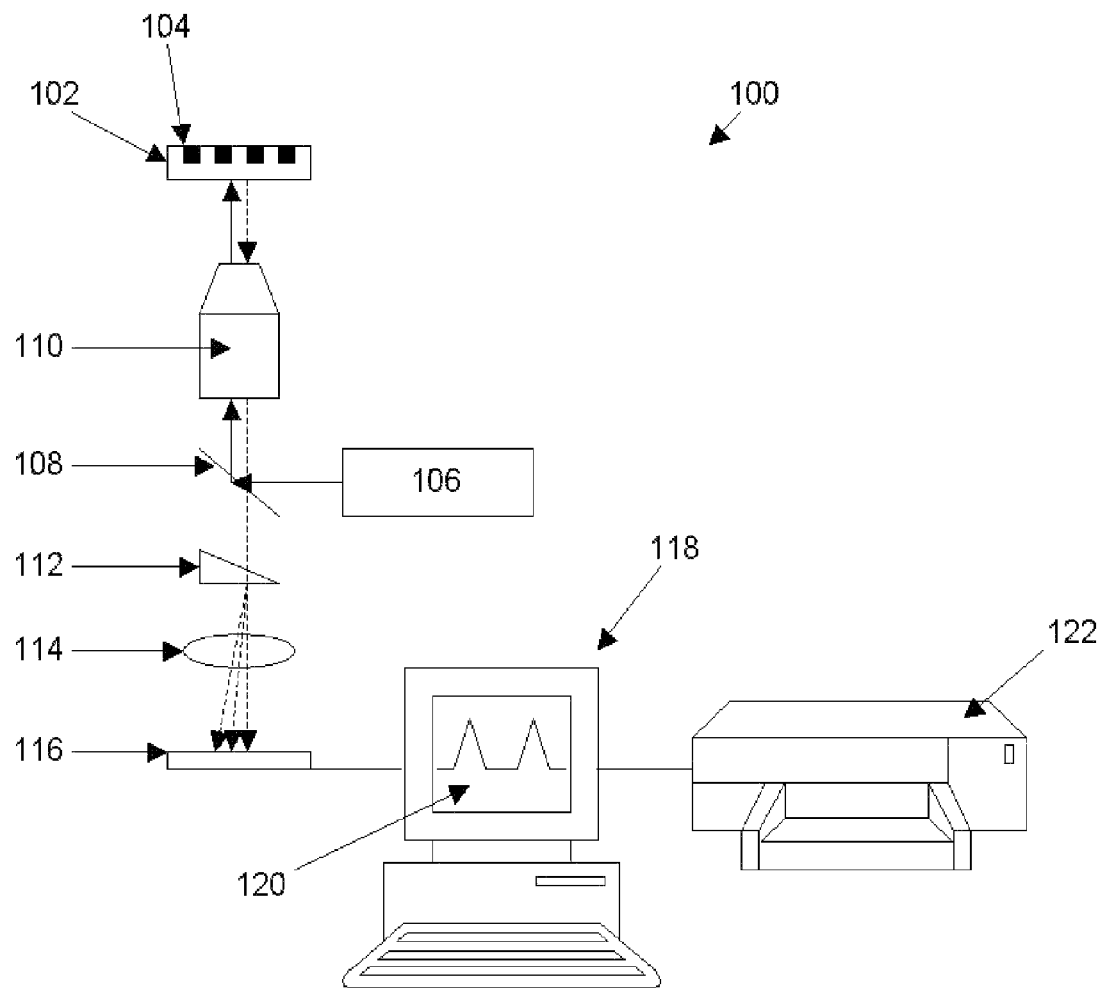
FIG. 1 provides a schematic illustration of an overall system used, inter alia, for sequencing by incorporation analyses.

I. Sequencing by Incorporation Processes and Systems

The present invention is generally directed to novel processes, and particularly computer implemented processes, software and systems for monitoring and characterizing optical signals from analytical systems, and particularly systems that produce signals related to the sequence of nucleic acids in a target or template nucleic acid sequence, using a sequencing by incorporation process. The present invention is also generally directed to novel processes for analyzing optical and associated data from sequencing by incorporation processes to ultimately determine a nucleotide base sequence (also referred to herein as "base calling'). The present invention is also generally directed to novel processes for analyzing sequencing by incorporation processes from many reactions locations in real time.

In sequencing by incorporation methods, the identity of the sequence of nucleotides in a template nucleic acid sequence is determined by identifying each complementary base that is added to a nascent strand being synthesized against the template sequence, as such bases are added. While detection of added bases may be a result of detecting a byproduct of the synthesis or extension reaction, e.g., detecting released pyrophosphate, in many systems and processes, added bases are labeled with fluorescent dyes that permit their detection. By uniquely labeling each base with a distinguishable fluorescent dye, one attaches a distinctive detectable characteristic to each dye that is incorporated, and as a result provides a basis for identification of an incorporated base, and by extension, its complementary base upon the template sequence.

A number of sequencing by incorporation methods utilize a solid phase immobilized synthesis complex that includes a DNA polymerase enzyme, a template nucleic acid sequence, and a primer sequence that is complementary to a portion of the template sequence. The fluorescently labeled nucleotides are then added to the immobilized complex and if complementary to the next base in the template adjacent to the primer sequence, they are incorporated onto the 5' end of the primer as an extension reaction product.

In some cases, the labeled bases are added under conditions that prevent more than a single nucleotide addition. Typically, this is accomplished through the inclusion of a removable extension terminating group on the 5' position of the added nucleotide, which prevents any further extension reactions. In some cases, the removable terminating group may include the fluorescent label. In this context, the immobilized complex is interrogated with one or more labeled nucleotide analogs. When a labeled analog is added, the extension reaction stops. The complex is then washed to eliminate all unincorporated labeled nucleotides. Incorporation is then determined based upon the presence of a particular fluorescent label with the immobilized complex, indicating incorporation of the base that was so labeled. The removable chain terminating group and the label, which in some cases may comprise the same group, are then removed from the extension product and the reaction and interrogation is repeated, stepwise, along the template sequence.

In an alternative and preferred aspect, incorporation events are detected in real-time as the bases are incorporated into the extension product. Briefly, this is accomplished by providing the complex immobilized within an optically confined space or otherwise resolved as an individual molecular complex. Nucleotide analogs that include fluorescent labels coupled to the polyphosphate chain of the analog are then exposed to the complex. Upon incorporation, the nucleotide along with its label is retained by the complex for a time and in a manner that permits its detection that is distinguishable from detection of random diffusion of unincorporated bases. Upon completion of incorporation, all but the alpha phosphate group of the nucleotide is cleaved away, liberating the label from retention by the complex, and diffusing the signal from that label. Thus, during an incorporation event, a complementary nucleotide analog including its fluorescent labels is effectively "immobilized" for a time at the incorporation site, and then the fluorescent label is subsequently released and diffuses away when incorporation is completed. According to specific embodiments of the invention, detecting the localized "pulses" of florescent tags at the incorporation site, and distinguishing those pulses from a variety of other signals and background noise as described below, allows the invention to effective call bases is real-time as they are being incorporated. In conjunction with optical confinements and/or single molecule resolution techniques, the signal resulting from incorporation can have one or more of increased intensity and duration as compared to random diffusion events and/or other non-incorporation events.

In all of the foregoing aspects, optical signal data is required to be processed to indicate real incorporation events as compared to other signals derived from non-incorporation events, and to identify the bases that are incorporated in those real incorporation events. The processing requirements become even greater where multiple different colored labels are used in interrogating larger and larger numbers of immobilized complexes arrayed over reaction substrates.

For purposes of the present invention, the processes and systems will be described with reference to detection of incorporation events in a real time, sequence by incorporation process, e.g., as described in U.S. Pat. Nos. 7,056,661, 7,052, 847, 7,033,764 and 7,056,676 (the full disclosures of which are incorporated herein by reference in their entirety for all purposes), when carried out in arrays of discrete reaction regions or locations. An exemplary sequencing system for use in conjunction with the invention is shown in FIG. 1. As shown, the system 100 includes a substrate 102 that includes a plurality of discrete sources of optical signals, e.g., reaction wells or optical confinements or reaction locations 104. In typical systems, reaction locations 104 are regularly spaced and thus substrate 102 can also be understood as an array 102 of reaction locations 104. An excitation light source, e.g., laser 106, is optionally provided in the system and is positioned to direct excitation radiation at the various signal sources. This is typically done by directing excitation radiation at or through appropriate optical components, e.g., dichroic 108 and objective lens 110, that direct the excitation radiation at the substrate or array 102, and particularly the signal sources 104. Emitted signals from source 104 are then collected by the optical components, e.g., objective lens 110, and passed through additional optical elements, e.g., dichroic 108, prism 112 and lens 114, until they are directed to and impinge upon an optical detection system, e.g., detector array (or camera) 116. The signals are then detected by detector array 116, and the data from that detection is transmitted to an appropriate data processing unit, e.g., computer 118, where the data is subjected to interpretation, analysis, and ultimately presented in a user ready format, e.g., on display 120, printout 122 from printer 124, or the like, or may be stored in an appropriate database, transmitted to another computer system, or recorded onto tangible media for further analysis and/or later review. Connection of the detector to the computer may take on a variety of different forms. For example, in preferred aspects, the detector is coupled to appropriate Analog to Digital (A/D) converter that is then coupled to an appropriate connector in the computer. Such connections may be standard USB connections, Firewire® connections, Ethernet connections or other high speed data connections. In other cases, the detector or camera may be formatted to provide output in a digital format and be readily connected to the computer without any intermediate components.

This system, and other hardware descriptions herein, are provided solely as a specific example of sample handling and image capture hardware to provide a better understanding of the invention. It should be understood, however, that the present invention is directed to data analysis and interpretation of a wide variety of real-time florescent detecting systems, including systems that use substantially different illumination optics, systems that include different detector elements (e.g., EB-CMOS detectors, CCD's, etc.), and/or systems that localize a template sequence other than using the wave-guides described herein.

In the context of the nucleic acid sequencing methods described herein, it will be appreciated that the signal sources each represent sequencing reactions, and particularly, polymerase mediated, template dependent primer extension reactions, where in preferred aspects, each base incorporation event results in a prolonged illumination (or localization) of one of four differentially labeled nucleotides being incorporated, so as to yield a recognizable pulse that carries a distinguishable spectral profile or color.

As noted previously, the present invention is generally directed to machine or computer implemented processes, and/or software incorporated onto a computer readable medium instructing such processes, as set forth in greater detail below. As such, signal data generated by the reactions and optical systems described above, is input or otherwise received into a computer or other data processor, and subjected to one or more of the various process steps or components set forth below. Once these processes are carried out, the resulting output of the computer implemented processes may be produced in a tangible or observable format, e.g., printed in a user readable report, displayed upon a computer display, or it may be stored in one or more databases for later evaluation, processing, reporting or the like, or it may be retained by the computer or transmitted to a different computer for use in configuring subsequent reactions or data processes.

Computers for use in carrying out the processes of the invention can range from personal computers such as PC or MacIntosh® type computers running Intel Pentium or Duo-Core processors, to workstations, laboratory equipment, or high speed servers, running UNIX, LINUX, Windows®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

While described in terms of a particular sequencing by incorporation process or system, it will be appreciated that certain aspects of the processes of the invention may be applied to a broader range of analytical sequencing or other operations and varying system configurations than those described for exemplary purposes.

Figure 2:
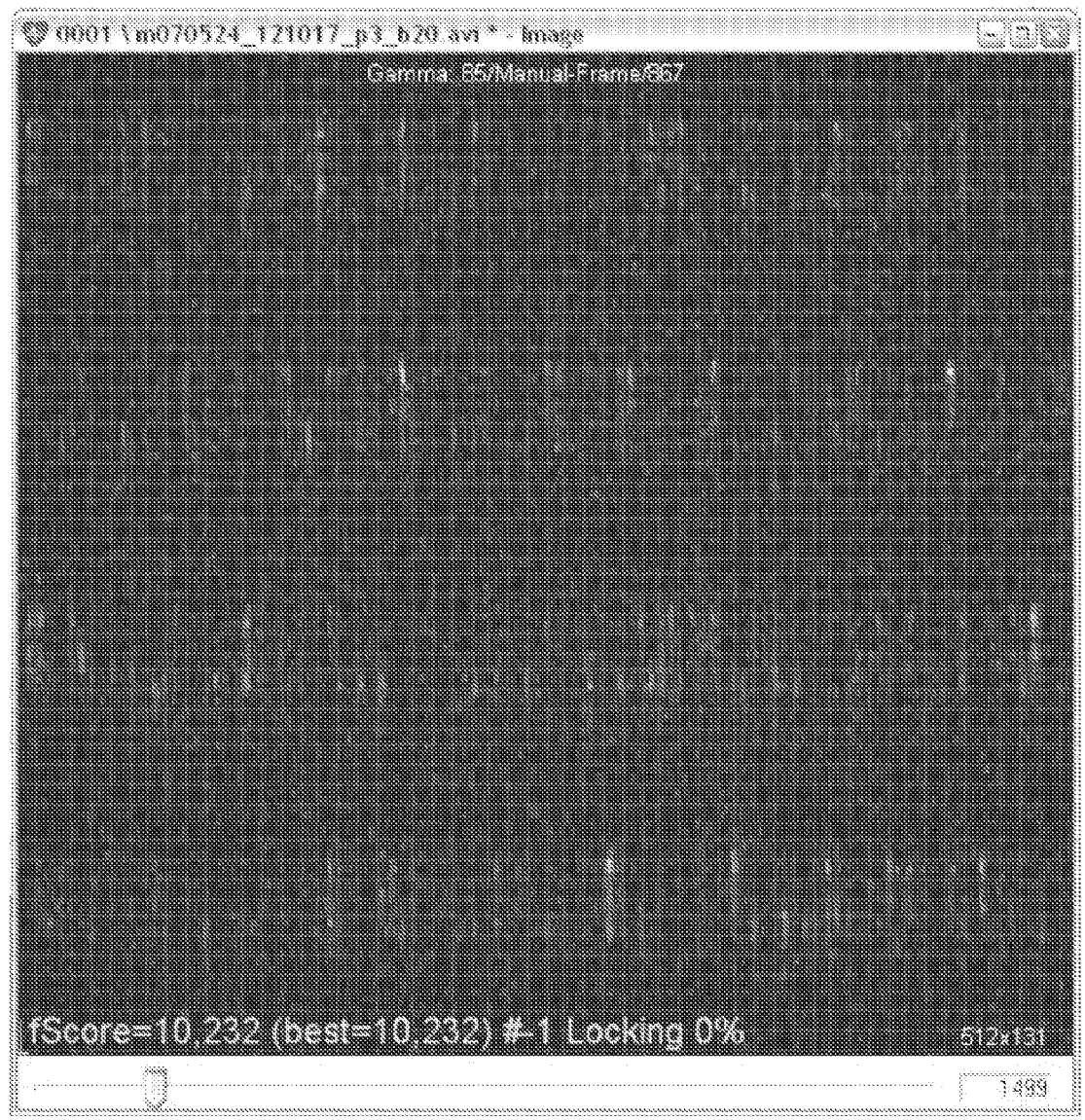
FIG. 2 is an EMCCD derived image of fluorescent signal pulses from an array of sequencing reactions.

FIG. 2 provides a single captured image frame of signal data on a portion of an EMCCD, where light portions correspond to optical signals that are incident upon the detector. Over time, these light areas appear as a series of flashes. Where those flashes have the appropriate characteristics, they are identified as an incorporation based signal, and assigned a color, based upon their spectral composition, e.g., as determined from their location of the detector.

II. Signal Data Processing Overview

In general, the present invention is directed to automated processes, and machine readable software that instructs such processes, for deciphering the signal data from a detection system that is optically coupled to any of the foregoing reactions, and particularly where such processes identify the incorporation of a nucleotide or nucleotide analog in a template dependent fashion, and identify the label associated with the incorporated analog and by extension, the analog and its complementary base in the template sequence.

Figure 3:
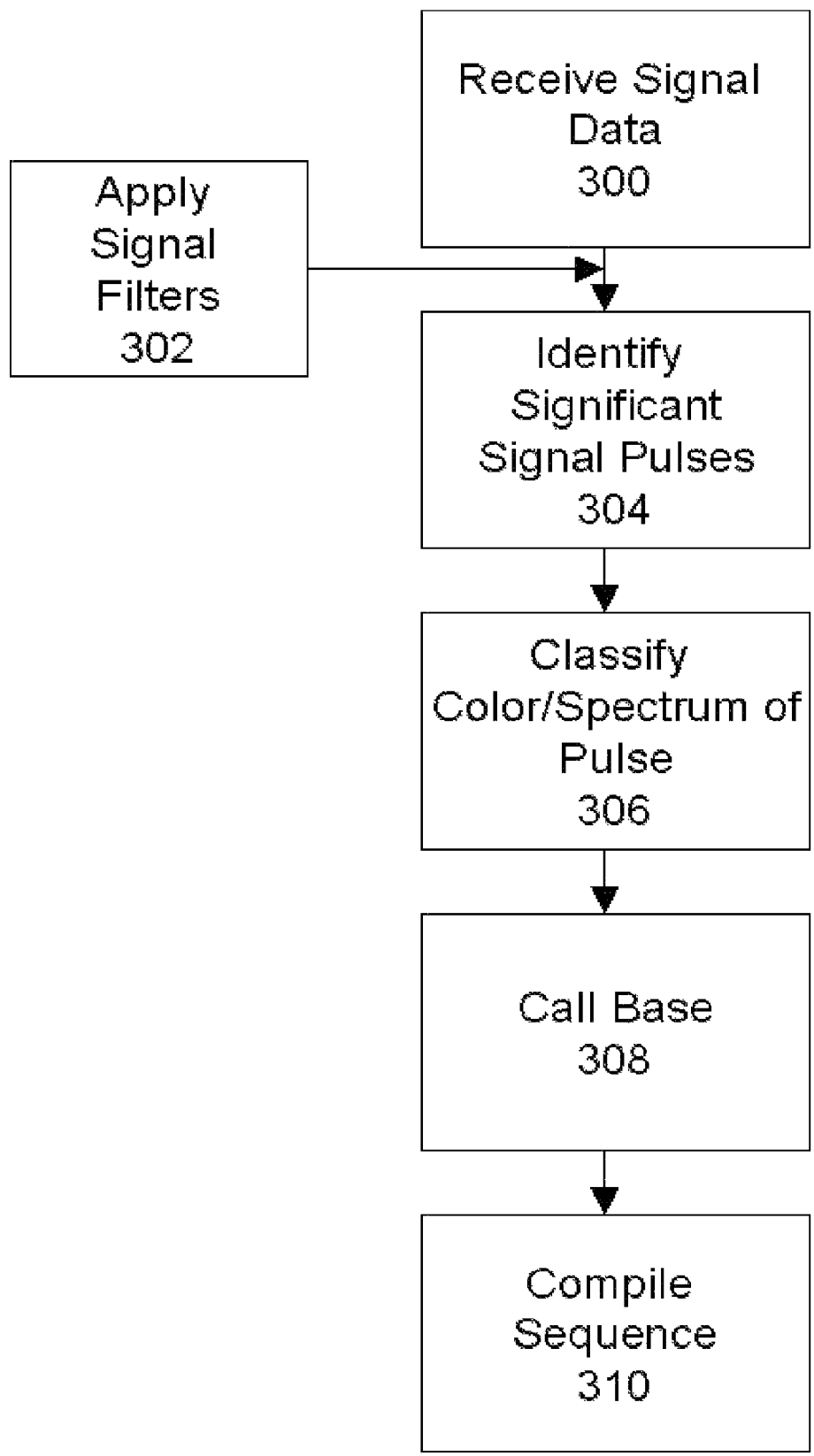
FIG. 3 provides a schematic flow-chart of the process used in monitoring sequencing reactions and identifying bases in the sequence.

A general flow chart illustrating the processing of signal data is provided in FIG. 3. In general, signal data is received by the processor at step 300. A number of initial calibrations operations may be applied as step 302. Some of these initial calibration steps may be performed just once at the beginning of a run or on a more continuous basis during the run. These initial calibration steps can include such things as centroid determination, alignment, gridding, drift correction, initial background subtraction, noise parameter adjustment, framerate adjustment, etc. Some of these initial calibration steps, such as binning, may involve communication from the processor back to the detector/camera, as discussed further below.

Generally, some type of spectral trace determination/spectral trace extraction/spectral filters are applied to the initial signal data at step 302. Some of all of this filter step may optionally be carried out at a later point in the process, e.g., after the pulse identification step 304. The spectral trace extraction/spectral filters may include a number of noise reduction and other filters as set forth elsewhere herein. Spectral trace determination is performed at this stage for many of the example systems discussed herein because the initial signal data received are the light levels, or photon counts, captured by a series of adjacent pixel detectors. For example, in one example system, 14 pixels (or intensity levels) from 14 positions are captured for an individual wave-guide at each frame. Light of different frequencies or spectrum will fall on more than one of the 14 positions and there is generally some overlap and possibly substantial overlap. According to specific embodiments of the invention, spectral trace extraction may be performed using various analysis, as discussed below, that provide the highest signal-to-noise ratio for each spectral trace.

As an alternative to a spectral trace determination, methods of the invention may also analyze a single signal derived from the intensity levels at the multiple pixel positions (this may be referred to as a summed spectral signal or a gray-scale spectral signal or an intensity level signal). In many situations, it has been found that spectral extraction, however, provides better SNR and therefore pulse detection when extracted spectral traces are analyzed for pulses somewhat separately. In further embodiments, a method according to the invention may analyze the multiple captured pixel data using a statistical model such as a Hidden Markov Model. In present systems, however, determining multiple (e.g., four) spectral traces from the initial signal data has proven a preferred method.

Whether the signal can be categorized as a significant signal pulse or event is determined at step 304. In some example systems, because of the small number of photons available for detection and because of the speed of detection, various statistical analysis techniques may be performed in determining whether a significant pulse has been detected.

If the signal is identified as a significant pulse or signal event at step 304, a further optional spectral profile comparison may be performed to verify the spectral assignment. This spectral profile comparison is optional in embodiments where spectral traces are determined prior to or during pulse identification. Once a color is assigned to a given incorporation signal, that assignment is used to call either the base incorporated, or its complement in the template sequence, at step 308. The compilation of called bases is then subjected to additional processing at step 310, to provide linear sequence information, e.g., the successive sequence of nucleotides in the template sequence, assemble sequence fragments into longer contigs, or the like.

As noted above, the signal data is input into the processing system, e.g., an appropriately programmed computer or other processor. Signal data may input directly from a detection system, e.g., for real time signal processing, or it may be input from a signal data storage file or database. In some cases, e.g., where one is seeking immediate feedback on the performance of the detection system, adjusting detection or other experimental parameters, real-time signal processing will be employed. In some embodiments, signal data is stored from the detection system in an appropriate file or database and is subject to processing in post reaction or non-real time fashion.

The signal data used in conjunction with the present invention may be in a variety of forms. For example, the data may be numerical data representing intensity values for optical signals received at a given detector or detection point of an array based detector. Signal data may comprise image data from an imaging detector, such as a CCD, EMCCD, ICCD or CMOS sensor. In either event, signal data used according to specific embodiments of the invention generally includes both intensity level information and spectral information. In the context of separate detector elements, such spectral information will generally includes identification of the location or position of the detector portion (e.g., a pixel) upon which an intensity is detected. In the context of image data, the spectral image data will typically be the data derived from the image data that correlates with the calibrated spectral image data for the imaging system and detector when the system includes spectral resolution of overall signals, e.g., as shown in FIG. 1. As discussed elsewhere herein, the spectral data may be obtained from the image data that is extracted from the detector, or alternatively, the derivation of spectral data may occur on the detector such that spectral data will be extracted from the detector.

For the sequencing methods described above, there will be a certain amount of optical signal that is detected by the detection system that is not the result of a signal from an incorporation event. Such signal, referred to hereafter as "noise" may derive from a number of sources that may be internal to the monitored reaction, internal to the detection system and/or external to all of the above. Examples of noise internal to the reaction being monitored includes, e.g.: presence of fluorescent labels that are not associated with a detection event, e.g., liberated labels, labels associated with unincorporated bases in diffused in solution, bases associated with the complex but not incorporated; presence of multiple complexes in an individual observation volume or region; non-specific adsorption of dyes or nucleotides to the substrate or enzyme complex within an observation volume; contaminated nucleotide analogs, e.g., contaminated with other fluorescent components; other reaction components that may be weakly fluorescent; spectrally shifting dye components, e.g., as a result of reaction conditions; and the like.

Sources of noise internal to the detection system, but outside of the reaction mixture can include, e.g., reflected excitation radiation that bleeds through the filtering optics; scattered excitation or fluorescent radiation from the substrate or any of the optical components; spatial cross-talk of adjacent signal sources; auto-fluorescence of any or all of the optical components of the system; read noise from the detector, e.g., CCDs, gain register noise, e.g., for EMCCD cameras, and the like. Other system derived noise contributions can come from data processing issues, such as background correction errors, focus drift errors, autofocus errors, pulse frequency resolution, alignment errors, and the like. Still other noise contributions can derive from sources outside of the overall system, including ambient light interference, dust, and the like.

These noise components contribute to the background photons underlying any signal pulses that may be associated with an incorporation event. As such, the noise level will typically form the limit against which any signal pulses may be determined to be statistically significant.

Identification of noise contribution to overall signal data may be carried out by a number of methods, including, for example, signal monitoring in the absence of the reaction of interest, where any signal data is determined to be irrelevant. Alternatively, and preferably, a baseline signal is estimated and subtracted from the signal data that is produced by the system, so that the noise measurement is made upon and contemporaneously with the measurements on the reaction of interest. Generation and application of the baseline may be carried out by a number of means, which are described in greater detail below.

In accordance with the present invention, signal processing methods distinguish between noise, as broadly applied to all non-significant pulse based signal events, and significant signal pulses that may, with a reasonable degree of confidence, be considered to be associated with, and thus can be tentatively identified as, an incorporation event. In the context of the present invention, a signal event is first classified as to whether it constitutes a significant signal pulse based upon whether such signal event meets any of a number of different pulse criteria. Once identified or classified as a significant pulse, the signal pulse may be further assessed to determine whether the signal pulse constitutes an incorporation event and may be called as a particular incorporated base. As will be appreciated, the basis for calling a particular signal event as a significant pulse, and ultimately as an incorporation event, will be subject to a certain amount of error, based upon a variety of parameters as generally set forth herein. As such, it will be appreciated that the aspects of the invention that involve classification of signal data as a pulse, and ultimately as an incorporation event or an identified base, are subject to the same or similar errors, and such nomenclature is used for purposes of discussion and as an indication that it is expected with a certain degree of confidence that the base called is the correct base in the sequence, and not as an indication of absolute certainty that the base called is actually the base in a given position in a given sequence.

One such signal pulse criterion is the ratio of the signals associated with the signal event in question to the level of all background noise ("signal to noise ratio" or "SNR"), which provides a measure of the confidence or statistical significance with which one can classify a signal event as a significant signal pulse. In distinguishing a significant pulse signal from systematic or other noise components, the signal generally must exceed a signal threshold level in one or more of a number of metrics, including for example, signal intensity, signal duration, temporal signal pulse shape, pulse spacing, and pulse spectral characteristics.

By way of a simplified example, signal data may be input into the processing system. If the signal data exceeds a signal threshold value in one or more of signal intensity and signal duration, it may be deemed a significant pulse signal. Similarly, if additional metrics are employed as thresholds, the signal may be compared against such metrics in identifying a particular signal event as a significant pulse. As will be appreciated, this comparison will typically involve at least one of the foregoing metrics, and preferably at least two such thresholds, and in many cases three or all four of the foregoing thresholds in identifying significant pulses.

Signal threshold values, whether in terms of signal intensity, signal duration, pulse shape, spacing or pulse spectral characteristics, or a combination of these, will generally be determined based upon expected signal profiles from prior experimental data, although in some cases, such thresholds may be identified from a percentage of overall signal data, where statistical evaluation indicates that such thresholding is appropriate. In particular, in some cases, a threshold signal intensity and/or signal duration may be set to exclude all but a certain fraction or percentage of the overall signal data, allowing a real-time setting of a threshold. Again, however, identification of the threshold level, in terms of percentage or absolute signal values, will generally correlate with previous experimental results. In alternative aspects, the signal thresholds may be determined in the context of a given evaluation. In particular, for example, a pulse intensity threshold may be based upon an absolute signal intensity, but such threshold would not take into account variations in signal background levels, e.g., through reagent diffusion, that might impact the threshold used, particularly in cases where the signal is relatively weak compared to the background level. As such, in certain aspects, the methods of the invention determine the background fluorescence of the particular reaction in question, including, in particular, the contribution of freely diffusing dyes or dye labeled analogs into a zero mode waveguide, and set the signal threshold above that actual background by the desired level, e.g., as a ratio of pulse intensity to background fluorophore diffusion, or by statistical methods, e.g., 5 sigma, or the like. By correcting for the actual reaction background, such as fluorophore diffusion background, the threshold is automatically calibrated against influences of variations in dye concentration, laser power, or the like. By reaction background is meant the level of background signal specifically associated with the reaction of interest and that would be expected to vary depending upon reaction conditions, as opposed to systemic contributions to background, e.g., autofluorescence of system or substrate components, laser bleedthrough, or the like.

In particularly preferred aspects that rely upon real-time detection of incorporation events, identification of a significant signal pulse may rely upon a signal profile that traverses thresholds in both signal intensity and signal duration. For example, when a signal is detected that crosses a lower intensity threshold in an increasing direction, ensuing signal data from the same set of detection elements, e.g., pixels, are monitored until the signal intensity crosses the same or a different intensity threshold in the decreasing direction. Once a peak of appropriate intensity is detected, the duration of the period during which it exceeded the intensity threshold or thresholds is compared against a duration threshold. Where a peak comprises a sufficiently intense signal of sufficient duration, it is called as a significant signal pulse. FIG. 3 provides a schematic of the process flow for an exemplary pulse classification aspect of the invention.

In addition to, or as an alternative to using the intensity and duration thresholds, pulse classification may employ a number of other signal parameters in classifying pulses as significant. Such signal parameters include, e.g., pulse shape, spectral profile of the signal, e.g., pulse spectral centroid, pulse height, pulse diffusion ratio, pulse spacing, total signal levels, and the like.

Either following or prior to identification of a significant signal pulse, signal data may be correlated to a particular signal type. In the context of the optical detection schemes used in conjunction with the invention, this typically denotes a particular spectral profile of the signal giving rise to the signal data. In particular, the optical detection systems used in conjunction with the methods and processes of the invention are generally configured to receive optical signals that have distinguishable spectral profiles, where each spectrally distinguishable signal profile may generally be correlated to a different reaction event. In the case of nucleic acid sequencing, for example, each spectrally distinguishable signal may be correlated or indicative of a specific nucleotide incorporated or present at a given position of a nucleic acid sequence. Consequently, the detection systems include optical trains that receive such signals and separate the signals based upon their spectra. The different signals are then directed to different detectors, to different locations on a single array based detector, or are differentially imaged upon the same imaging detector (See, e.g., U.S. Patent Publication No. 2007/0036511, which is incorporated herein by reference in its entirety for all purposes).

In the case of systems that employ different detectors for different signal spectra, assignment of a signal type (for ease of discussion, referred to hereafter as "color classification" or "spectral classification") to a given signal is a matter of correlating the signal pulse with the detector from which the data derived. In particular, where each separated signal component is detected by a discrete detector, a signal's detection by that detector is indicative of the signal classifying as the requisite color.

In preferred aspects, however, the detection systems used in conjunction with the invention utilize an imaging detector upon which all or at least several of the different spectral components of the overall signal are imaged in a manner that allows distinction between different spectral components. Thus, multiple signal components are directed to the same overall detector, but may be incident upon wholly or partly different regions of the detector, e.g., imaged upon different sets of pixels in an imaging detector, and give rise to distinguishable spectral images (and associated image data). As used herein, spectra or spectral image generally indicates a pixel image or frame (optionally data reduced to one dimension) that has multiple intensities caused by the spectral spread of an optical signal received from a reaction location.

In its simplest form, it will be understood that assignment of color to a signal event incident upon a group of contiguous detection elements or pixels in the detector would be accomplished in a similar fashion as that set forth for separate detectors. In particular, the position of the group of pixels upon which the signal was imaged, and from which the signal data is derived, is indicative of the color of the signal component. In particularly preferred aspects, however, spatial separation of the signal components may not be perfect, such that signals of differing colors are imaged on overlapping sets of pixels. As such, signal identification will generally be based upon the aggregate identity of multiple pixels (or overall image of the signal component) upon which a signal was incident.

The spectral classification, or identification of a color, associated with a given signal image on a detector may be accomplished by a number of methods. In particularly preferred aspects, a spectral image associated with a given signal (which may or may not be an incorporation event signal) is compared to a standard set of spectral image profiles associated with the signal events for which the system is being interrogated. Restated, a standard set of spectral image profiles are determined for the labels associated with the four different nucleotides and/or incorporation of those nucleotides, and those standards are used as comparators in identifying to which color a given unknown spectral image corresponds.

In a particular exemplary calibration process, a signal source, such as a reaction region is illuminated while containing only the individual fluorescent labels or fluorescently labeled nucleotide analogs of one dye color that give rise to signals during the monitored reaction, e.g., in the absence of the reaction complex. The spectral image for each color of dye is then stored for use in the later comparison with the spectral images from actual reaction derived signals. This standard set is then used as the comparator in identifying whether the spectral image from an actual signal event can be assigned to a given color with an acceptable level of confidence, and if so, what that color is. In some cases, the spectral profiles may be determined based upon theoretical models of the optical system and the emission spectra of the signal producing reagents, e.g., labeled nucleotides, without the need for empirical determination of the standard spectral images.

As noted above, because signal separation may not be perfect in imaging signals upon a detector array, the comparison of a given signal's spectral image to the standard spectral image profiles for the various colors of signals will assess the confidence with which a color may be assigned to a given signal event, based upon a number of parameters. By way of example, whether a given spectral image is identified as matching one of the standard spectral image profiles may be determined by subjecting the comparison to any of a variety of statistical correlation evaluations including, e.g., cross-correlation tests, $\chi^2$, least squares fit, and the like.

As will be appreciated, the steps of incorporation signal identification and color assignment may be performed in either order and are not dependent upon each other. Restated, one may first assign a color to the signal before categorizing it as a significant pulse, or alternatively, one may first categorize a signal as a significant pulse and then assign a color to that pulse.

Once a particular signal is identified as a significant pulse and is assigned a particular spectrum, the spectrally assigned pulse may be further assessed to determine whether the pulse can be called an incorporation event and, as a result, call the base incorporated in the nascent strand, or its complement in the template sequence. Calling of bases from color assigned pulse data will typically employ tests that again identify the confidence level with which a base is called. Typically, such tests will take into account the data environment in which a signal was received, including a number of the same data parameters used in identifying significant pulses, etc. For example, such tests may include considerations of background signal levels, adjacent pulse signal parameters (spacing, intensity, duration, etc.), spectral image resolution, and a variety of other parameters. Such data may be used to assign a score to a given base call for a color assigned signal pulse, where such scores are correlative of a probability that the base called is incorrect, e.g., 1 in 100 (99% accurate), 1 in 1000 (99.9% accurate), 1 in 10,000 (99.99% accurate), 1 in 100,000 (99.999% accurate), or even greater. Similar to PHRED or similar type scoring for chromatographically derived sequence data, such scores may be used to provide an indication of accuracy for sequencing data and/or filter out sequence information of insufficient accuracy.

Once a base is called with sufficient accuracy, subsequent bases called in the same sequencing run, and in the same primer extension reaction, may then be appended to each previously called base to provide a sequence of bases in the overall sequence of the template or nascent strand. Iterative processing and further data processing, as described in greater detail below, can be used to fill in any blanks, correct any erroneously called bases, or the like for a given sequence.

While the foregoing process generally describes the processes of the invention, additional detail is provided with reference to an exemplary sequencing process, below.

III. Exemplary Sequencing by Incorporation Process and System

The processes described above are further described in the context of a particularly preferred sequence-by-incorporation analysis using as a source of signals, a gridded array of optically confined, polymerase/template/primer complexes that are exposed to four different nucleotide analogs, e.g., A, T, G and C, that are each labeled at the terminal phosphate group of either a tri, tetra or pentaphosphate chain of the nucleotide or nucleotide analog (e.g., as a phosphate labeled nucleoside triphosphate, tetraphosphate or pentaphosphate). In preferred aspects, the optically confined complexes are provided within the observation volumes of discrete zero mode waveguide (ZMW) cores in an arrayed format. Although described in terms of optically confined reaction regions, it will be appreciated that the methods of the invention in whole or in part may be applicable to other types of sequencing by incorporation reactions and particularly those based upon immobilized reaction complexes, and more particularly, those employing optically resolvable single molecule complexes, e.g., including a single polymerase/template/primer complex.

Figure 4:
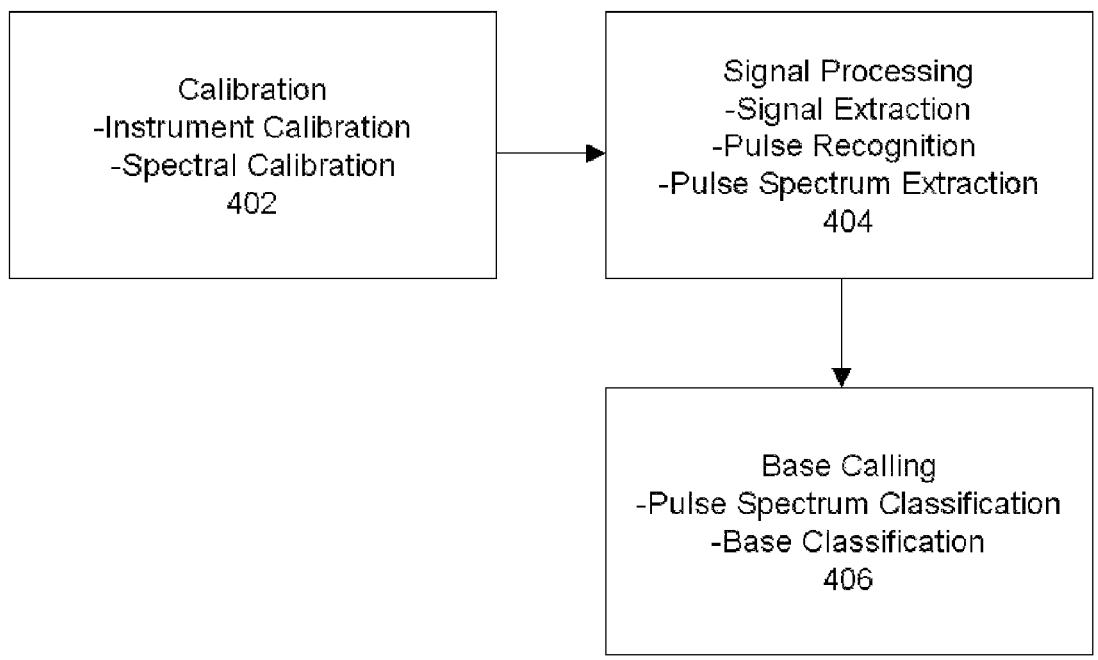
FIG. 4 is a high level flow chart breakdown of an overall real time sequence by incorporation process.

An example of an overall sequence process comprised of three general process categories is generally shown in FIG. 4. As shown, the process includes an initial calibration step 400, in which the system is calibrated from both an instrument standpoint and a reaction standpoint, e.g., to adjust for consistent noise sources, and calibrated for color identification, e.g., using standard dye or label sets. Once an actual sequencing data run commences, the signal data deriving from the system is subjected to initial signal processing at step 402, to identify significant signal events or pulses and to extract spectral signals from the signal data. Following the initial signal processing, classified pulses are then assessed at step 404 to classify signal data as corresponding to a given spectral signal event, and consequently as corresponding to incorporation of a particular base, or its complement.

Figure 5:
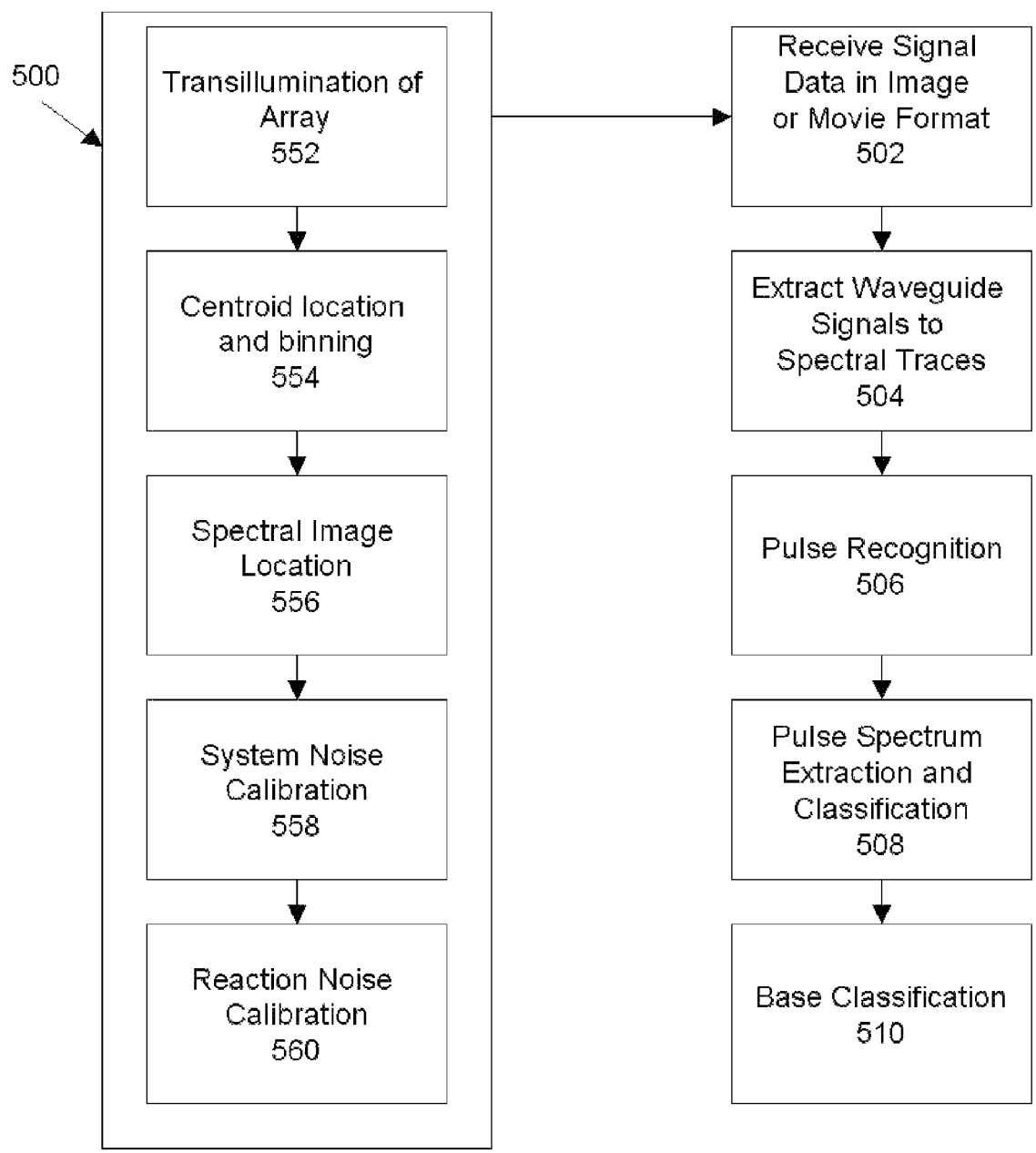
FIG. 5 is a detailed flow chart illustrating a number of the process steps included in the overall process shown in FIG. 4.

This exemplary, overall process is schematically illustrated in greater detail in the flow chart of FIG. 5. As shown, the system is initially calibrated to provide identification of the signals associated with each discrete signal source, to identify within that signal the most relevant signal portion, and to associate spectral information with different signal profiles. This calibration process, provided in greater detail below, is indicated at step 500, and is typically precedent and supplementary to the process of signal data processing from actual sequencing runs.

Following receipt of the signal data at step 502, the signal image or movie files for a given run are converted to spectral data at step 504 by comparing the overall signal data to the spectral standards created in step 500. For example, signals received from each waveguide are converted to two dimensional time-series or one dimensional spectral time series traces. As a result, the output of the conversion or extraction step is a series of individual movies or traces that indicate the different spectral signal components over time, e.g., as a series of n signal traces. For a typical four-color sequencing process, this will typically result in four different traces, where each trace represents the signal spectrum correlated with a different standard spectral image profile. Once the data is converted to spectrally discrete traces, the different traces are subjected to a pulse recognition or classification process at step 506. As noted above, in particularly preferred aspects, the pulse recognition process identifies significant signal pulses (e.g., pulses that meet criteria of significance for assessment to determine if they are associated with an incorporation event) in each trace, and distinguishes those from background or noise signals, e.g., those resulting from normal diffusion of unincorporated label molecules or labeled nucleotides into the observation volume, non-specific adsorption of labels or analogs within or near the observation volume, or the like. The pulse recognition process, as described in greater detail, below, identifies significant pulses based upon a number of signal characteristics as described above, including whether such signals meet signal thresholds described above (intensity, duration, temporal pulse shape, pulse spacing and spectral characteristics). Once a pulse is initially identified as significant, the time collapsed spectrum for a given significant pulse is extracted and classified at step 508 by correlating the pulse spectrum to the standard spectral image for the various signal possibilities, e.g., dye colors, by comparing the pulse spectrum to the standard spectra, based upon one or a number of different pulse metrics, as set forth elsewhere herein. For example, in this process, the statistical significance of the fit of the pulse spectral image may be calculated against those spectral images for the 4 different standard dye images, e.g., using a $\chi^2$ test, or the like.

Once a significant pulse is correlated to a given standard dye spectrum, the pulse is then subjected to the base classification process at step 510, where the spectrum assigned pulse data is further filtered based upon one or more of a number of signal parameters, which provide a basis of classification of the signal as a particular base (also referred to herein as a base classifier). The base classifier will typically comprise an algorithm that assesses the one or more signal parameters in order to classify the particular pulse as being correlative of a given base incorporation event. By way of example, such algorithms will typically comprise a multi-parameter fit process to determine whether a spectrum assigned signal pulse corresponds to an incorporation event within a selected probability range, as described in greater detail, below.

A. Calibration

1. Gridding

As noted previously, the processes of the invention are particularly useful in processing signal data from arrays of optically confined sequencing or other optically monitored reactions. In particular, the systems and processes of the invention are particularly preferred for use with arrays of zero mode waveguides in which polymerase mediated, template directed primer extension reactions are occurring, where the addition of a nucleotide to an extending primer gives rise to a fluorescent signaling event. The signals emanating from the various signal sources on the array are then imaged onto an imaging detector, such as a CCD, ICCD, EMCCD or CMOS based detector array. As a result, prior to running a sequencing experiment, it is typically desirable to calibrate the system to the locations of the different zero mode waveguides (or other signal sources in other processes) in the overall array, or more importantly, the position upon the detector at which the different signals from each signal source are imaged.

While in some cases, location of imaged signals could be carried out on a completed sequencing run, in many cases, it is preferred to accomplish this prior to capture of sequencing data, so that signal data associated with a given signal can be combined (e.g., binned) prior to extraction from the detector array. In particular, by identifying a collection of pixels associated with a given signal source and/or a given spectral signal from that signal source, one can collapse or combine the signal data from the different pixels prior to extracting it from the detector array. This has the result of reducing the amount of overall signal data that is required to be processed in subsequent steps.

In locating the image of the different signal sources on the detector, the array is typically illuminated so as to provide an imaged signal associated with it on the detector. In the case of an array of ZMWs (zero mode waveguides), the array is trans-illuminated through the waveguide using a reference light source. The referenced light source may be a broad band light source imaged onto the detector through a narrow bandpass filter, e.g., 543 nm, as shown in step 552 in FIG. 5 or may be an emitter of narrow-band light. Such trans-illumination provides for high signal to noise levels for the image, allowing for more accurate centroid estimation for gridding, more accurate point spread function estimation, and provides a fixed spectral reference point for each imaged waveguide.

Figure 6:
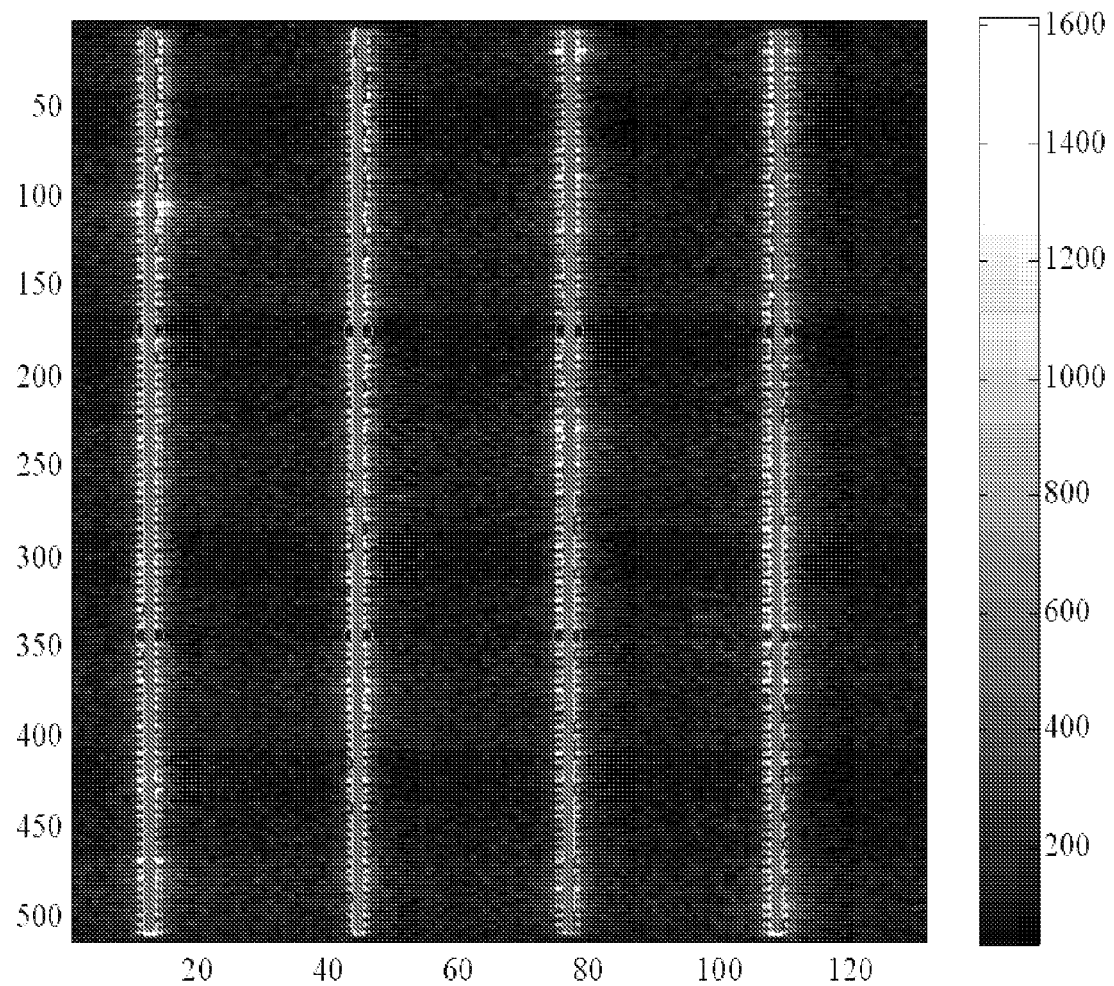
FIG. 6 is an EMCCD image of a trans-illuminated array of zero mode waveguides.

The imaged signals are then aligned to the known spacing of image sources on the waveguide array optionally employing registration marks incorporated into the array. For example, in preferred aspects, rows of waveguides in an array will include one or more blank spaces in place of a waveguide, where the blanks will be spaced at regular, known intervals, for alignment. Other registration marks might include regularly spaced image sources that are separate from the waveguides, but are at known locations and spacing relative to the waveguides in the array to permit alignment of the image to the array. Such image sources may include apertures like waveguides, or may include fluorescent or luminescent marks that provide a signal event that can be used for alignment. The gridding step also permits the identification and calibration of the system to take into account any artifacts in a given waveguide array, e.g., blank waveguides other than registration blanks, irregularly spaced waveguides, or the like. FIG. 6 is an image of a trans-illuminated waveguide array that includes four rows of approximately 100 waveguides per row. Alignment may additionally be aided by feature recognition software that correlates signal peaks in the trans-illuminated array image with the known relative locations of waveguides on an array.

Figure 7:
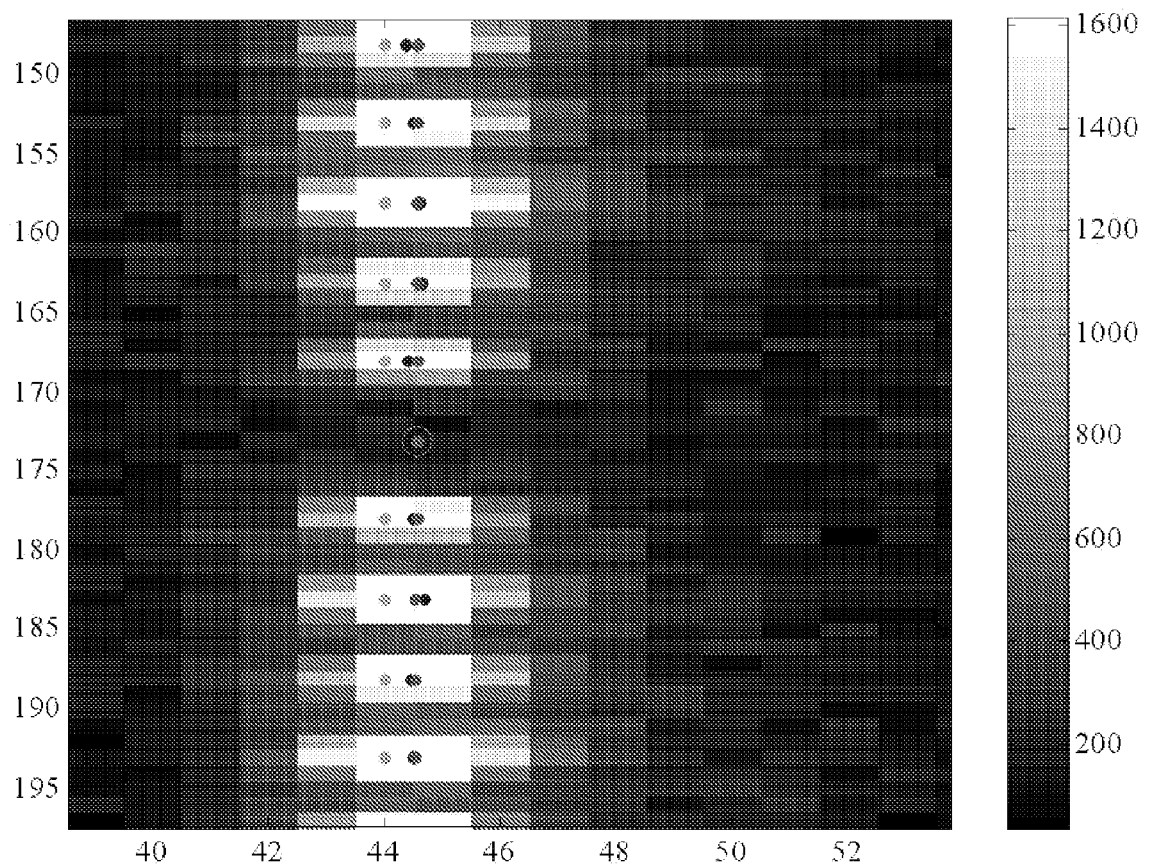
FIG. 7 is a close up image of a subset of the trans-illuminated waveguides in the array which also shows the centroid determination for each imaged waveguide.

During the gridding step, the position of each waveguide image in the intra-row dimension is determined. Typically, a multi-point spread function is fit to each image to identify the image centroids in the intra-row dimension (See step 504 in FIG. 5). This is schematically illustrated in FIG. 7, which provides a close-up image of a series of trans-illuminated waveguide images in a given row, showing the identified centroids for each image. Also shown in FIG. 7 is a blank space that is used in registration of the overall array image, as discussed above. The image positions are then used in subsequent processing to associate a given set of signal data to a given waveguide, and consequently a given extension reaction, and to permit collapsing of image data from a given location to spectral images from that location.

2. Spectral Extraction

Once the location of the imaged waveguides is determined, the range of the full imaged spectra for each waveguide are identified and this range may be communicated to detector 116 to allow binning and other data reduction operations to be performed prior to extraction from the detector. By way of example, an image of each ZMW typically has its narrowest dimension along the axis of the specific row in which the waveguide is disposed (and that is orthogonal to the axis of the spectrally separated image). For purposes of discussion, the row axis is termed the spatial axis, while the axis that runs through the elongated image of the spectral components of the waveguide is termed the spectral axis. For example, in at least one exemplary system, the spatial axis dimension of an image will fall within a 5 pixel range, while the spectral axis will typically fall within a pixel range of from about 12 pixels to about 20 or more pixels, depending upon the extent of spectral separation of the image, and the size of the image in the first instance. Thus, the pixels corresponding to the full spectral image of a given waveguide may range from 60 to 100 or more pixels in a rectangular area. These pixels that are associated with each waveguide are optionally combined (binned) by the detector 116 prior to further analysis. This combination may optionally be performed upon full image data extracted from a detector, e.g., a software process, or it may be performed within the detector, e.g., a firmware process, and output to the software process.

The software based process has a number of advantages, including, e.g.: minimizing data loss during the acquisition of the image data or movie; maximizing the signal to noise ratio of pulses based on establishing flux distribution around each waveguide in spatial dimension and noise characteristics of detector and doing appropriate weighted sum of pixel intensities; detecting and compensating for any instrument drift during movie acquisition; allowance for algorithmically distinguishing some instrument systematic artifacts such as Clock Induced Charge (CIC) noise and cosmic ray events on the CCD from the signals of interest based upon the two dimensional images being processed; the ability to estimate and potentially correct spatial cross-talk between ZMWs.

Certain disadvantages of the software process include, e.g.: a decrease in the maximum frame rate of the detector camera, as more pixels are read out from the camera, reducing the ability to detect shorter pulses; and increased instrument noise compared with firmware processes described below, resulting from read-noise that is associated with each pixel that is read out.

To maximize the signal to noise ratio (SNR) of the extracted spectrum, a weighted sum of pixels along the spatial axis of the ZMW is performed. Weights that maximize the SNR are determined by the inverse variance of each pixel. The first step is to estimate ZMW flux distribution shape in the spatial dimension for each line of ZMWs. This shape for individual ZMW signals in the trans-illumination phase is identical (governed by the instrument Point Spread Function (PSF)). This will typically provide a good estimate of the PSF for subsequent analyses, e.g., in a sequencing movie.

In measuring the PSF in the transilluminated waveguide image typically the regular nature of the grid allows for accurate estimates in the spatial dimension by summing lines centered along a line of ZMWs. By subtracting adjacent lines an accurate local background correction can be made to leave a one dimensional intensity profile of ZMWs whose shapes are governed entirely by the instrument point spread function. The instrument PSF can be modeled (e.g., by a Gaussian or Moffat function). Fits to the one dimensional profile of a line of ZMWs may solve for all ZMW amplitudes, the ZMW spacing, and a PSF width. These fits can also solve for more parameters (e.g. a polynomial model of PSF width as a function of FOV position) in order to account for second order effects, such as variation of the optical PSF across the field of view (FOV) of the camera or variations in chip geometry.

In certain additional cases, the variance of the pixel signal intensity for a given camera is also determined. Generally for CCDs this relationship is predictable and measurable being governed by the Shot noise on the detected photons and the CCD read-noise, as well as variances from the gain register for, e.g., EMCCDs. These CCD parameters are typically estimated from the calibration data using static signal data taken at different intensities, but they can also be measured from stable pixels (pulse free) in a sequencing movie. Using the PSF estimate and the signal-variance relationship the CCD pixels are weighted-summed by their inverse variance to maximize the SNR in the collapsed spectrum. Typically, this binning or data reductions process reduces a two-dimensional pixel image for each ZMW into a one-dimensional line of pixel values. The differences in pixels along this line are due to spectral refraction as described herein. Thus, each pixel of this line is at times herein referred to as a spectral pixel of a ZMW and the line of pixels is at times herein referred to as a spectra of the ZMW.

In an alternative extraction process, the binning of spectral images from each waveguide is carried out on the detector (e.g., a camera chip in a firmware controlled process). In particular, a high resolution calibration image is taken and used to establish a map for on-chip binning in the spatial axis of the CCD in hardware to essentially read out spectra directly from the camera. In contrast to the software driven process above, this process provides benefits of: reading out fewer pixels, allowing for increased maximum frame rate, for increased sensitivity to the shorter timescale pulses; fewer pixels imaged per ZMW and therefore less instrument read-noise; and less data storage of raw output from camera. Of course, certain disadvantages of this process include, e.g.: potential for data loss during acquisition from pixels not binned; lower signal to noise ratios per pulse (if pixels are not in regime where read-noise dominates); instrument stability and/or dynamic drift correction must be done by the instrument during acquisition, rather than as a software correction; a reduced ability to distinguish instrument artifacts such as CIC noise and cosmic rays based on spatial profile; and reduced ability to account for and remediate spatial cross-talk between ZMWs, due to loss of spatial information in the image.

In this process, the location of ZMW signals is determined from a full illumination frame, and on-camera (or "on-chip") binning sums (in the spatial direction) only those CCD lines associated with a line of ZMW holes which contains the majority of the signal and reads out only those lines during the actual movie acquisition. This effectively turns output of the CCD from reading out images of waveguides and waveguide arrays, to directly reading out spectra from the camera chip. As noted previously, by reducing the number of pixels output from the camera over a larger field of view, higher maximum frames rates can be maintained. The optimal binning strategy is the one that maximizes the SNR of pulses from each hole.

3. Color Calibration

During the calibration process, the system is also calibrated for the image spectra from each source. In particular, in a sequencing reaction, signals associated with each of the different incorporated bases have a distinguishable spectrum. The system used in the preferred sequencing process, e.g., as schematically illustrated in FIG. 1, through the use of a wedge prism or other similar optical train component(s), directs each spectrally different signal component from a given waveguide, to a different spot on the detector, where each type of signal from a given waveguide, is separated from the others in one dimension. In particular, a wedge prism will deflect spectrally different signal components to a greater or lesser degree, depending upon their wavelengths, and image those components on different portions of the detector (See, e.g., U.S. Patent Publication No. 2007/0036511, previously incorporated herein by reference). In order to identify a signal from a sequencing reaction as corresponding to a given label, the system must first be calibrated to the shape and location on the detector at which each spectrally different signal component from each waveguide, will be imaged, e.g., as shown at step 556 of FIG. 5.

During spectral calibration, the waveguide array is provided with a standard reference label that may include each pure dye, a pure labeled nucleotide, or another relevant pure component, e.g., a polymerase/template/primer complexed labeled nucleotide. The signal of each pure label compound is then imaged upon the detector and its location is mapped. This is repeated for each different label that is to be used in a reaction. For a typical sequencing operation, this would include the four different labels used in identifying each of the four different nucleotides. The result is a spectral template or map for the overall array and for the various different labels to be used in a sequencing operation.

In many cases, the calibration spectra will be taken at different locations on a waveguide array, e.g., from different waveguides, than analytical reads, e.g., sequencing movies. As such, the positions of the spectral images are measured relative to the reference wavelength used in the transillumination phase, above, which can then be used to correlate spectral images from different waveguide locations obtained during a sequencing movie. These spectral templates can then be aligned to the different locations on the CCD as given by the centroids of the transillumination image in the sequencing movie. Typically however the spectra as seen on the CCD are coarsely sampled and the spectral shape is sensitive to the subpixel centroid location of the ZMW within the image. To improve on estimating this shape accurately the calibration spectra are taken at multiple subpixel centroids, e.g., 0.1 pixels samplings. These can then be combined into a much higher resolution spectrum than a single image can provide. With a subpixel spectral reference centroid estimated from a ZMWs transillumination image, this high resolution spectrum can then be accurately downsampled to account for any pixelation of the camera. In addition, due to potential distortions in the optics (e.g. coma, chromatic and spherical aberration) one may also obtain calibration spectra across the field of view of the chip. In this way, a unique spectrum is used from the calibration data for a ZMWs position, thereby accounting for spatially dependent effects that may arise from the optics.

4. Other System Calibration

In addition to the location calibration and spectral calibration, it will be appreciated that other calibration processes may also be performed. For example, in some cases, the detector is calibrated by providing for an imaging step while the shutter is closed, to ascertain and calibrate for any noise that may be deriving from the detector itself. Likewise, an overall system noise calibration step may be performed in the absence of any fluorescent or other labeling components within the waveguides in the array, to ascertain and calibrate for noise that derives from the system as a whole, e.g., autofluorescence of the optical train components, the array substrate, etc. (See step 558 of FIG. 5). Typically, these noise sources will be factored into one or more of the filtering steps in an overall process, e.g., subtracted from overall signal levels, or in one of the other calibration steps, e.g., in identification of the image locations and/or generation of the spectral template. The system is also typically calibrated for additional noise sources deriving from the reaction itself, e.g., resulting from nonspecific adsorption of dyes within an observation volume, presence of multiple complexes, and the like, as shown at step 560 of FIG. 5.

B. Signal Extraction to Traces

Images or movies of signal data deriving from an actual sequencing reaction is processed initially based upon the calibration of the system, as set forth above. In particular, signal data is associated with a particular signal source, e.g., waveguide, in the array based upon the positional data obtained during the calibration process. The result of the calibration process, above, is a time series of spectra for each waveguide, which is stored as an image with dimensions of the number of scans and number of spectral pixels (See, e.g., FIG. 8). The next step is to identify and classify pulse spectra from this image. Since the spectral templates for experimentally represented dyes for each ZMW are known through the above calibration process, these 2D images can be converted to 1D time series signals (one for each dye). This conversion can be achieved by a number of methods. For example, one may employ a linear matrix inversion in which the dye calibration templates are used to decompose the spectrum into the individual intensities of the pure dye spectra at each time point. Alternatively, or additionally, one may employ a weighted sum of spectral pixels using the dye templates to maximize the SNR of a pure dye sum in its trace.

Figure 8:
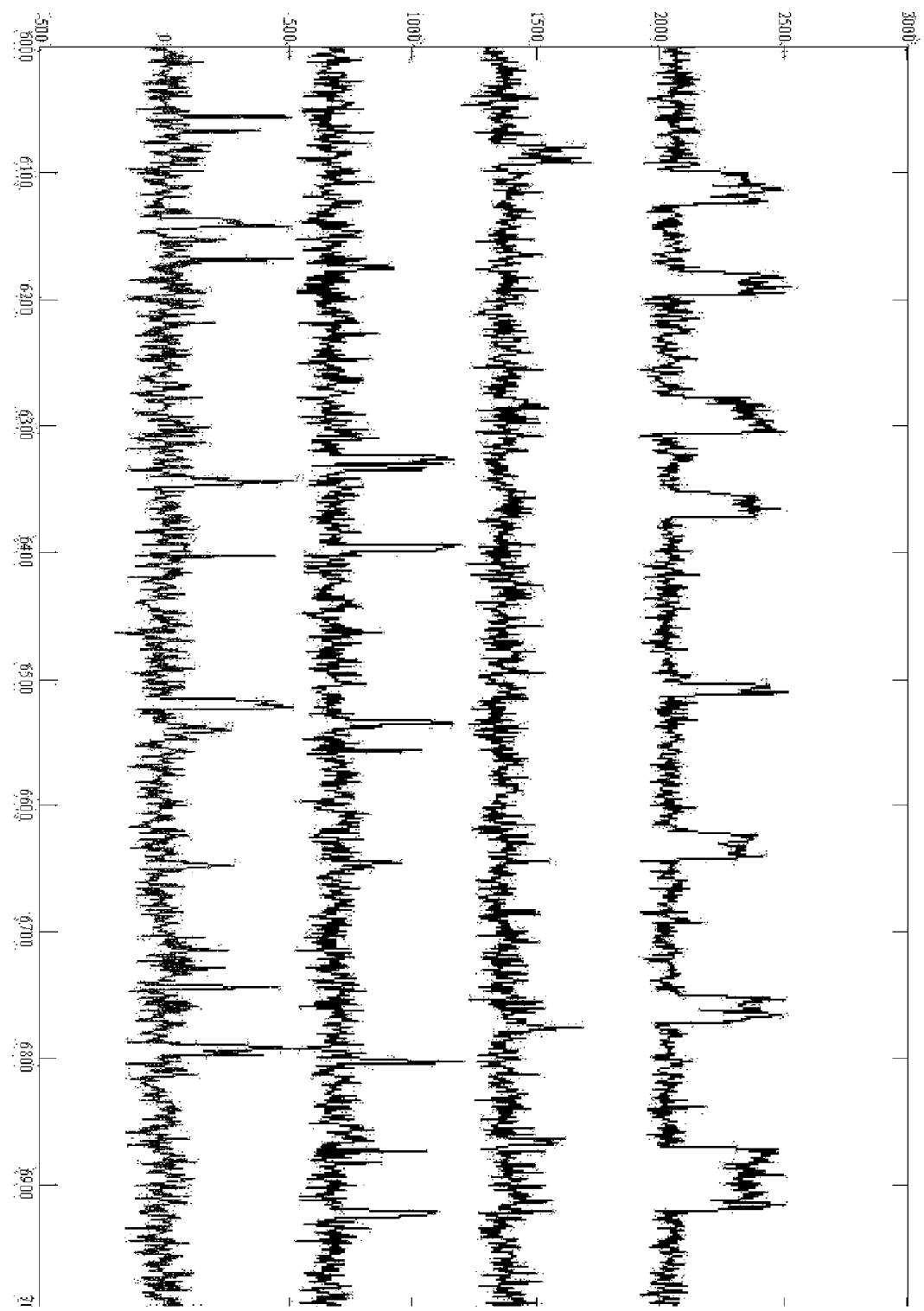
FIG. 8 illustrates an exemplary 4 channel signal trace derived from an imaged waveguide.

In either event, the signals for each waveguide are compared to the spectral template and for each located signal source, each spectral component is then collapsed into an individual trace. In particular, the signal intensity at the image location that corresponds to a particular spectral signal from a particular signal source is plotted and/or monitored as a function of time, to provide a time resolved trace of signal activity of a given color for a given waveguide. As a result, for each located waveguide using a four color sequencing process, four different traces will be generated that reflect the intensity of the different signal components over time. An example of trace data from four spectral traces from a single waveguide is shown in FIG. 8.

As noted above, the signal data represented in each trace is an aggregate signal of the particular pixels associated with a given spectral component of the signal. In particular, an image location may include a plurality of pixels in the detector, in order to yield the most accurate data. Rather than process signal data from each pixel in the image, the overall image can be aggregated and processed as a single data unit. Aggregation of the pixel data can be accomplished in the processor but is preferably carried out in the detector, itself, as an initial process, to minimize the amount of data created by the system and subject to further processing.

C. Pulse Recognition

Figure 9:
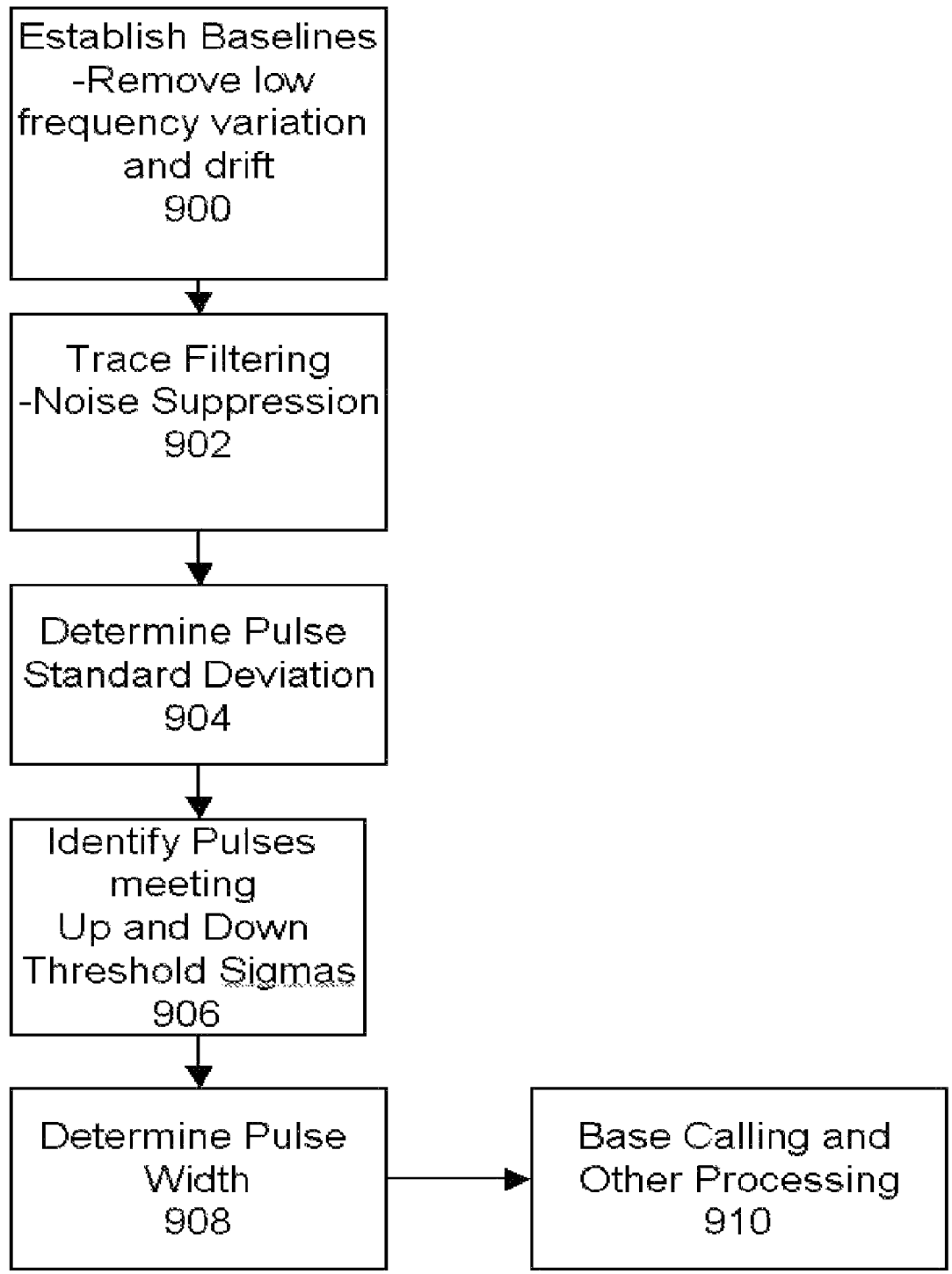
FIG. 9 provides a schematic flow-chart of a pulse recognition process.

Once the traces have been generated for a given waveguide, they are subjected to the pulse recognition process. The pulse recognition process is schematically illustrated in the flow chart of FIG. 9. In the initial step 900, a baseline is established for the trace. Typically, the baseline may comprise signal contributions from a number of background sources (depending on the details of the spectral and trace extraction steps). For example, such noise will typically include, e.g., global (out-of-focus) background (e.g., auto-fluorescence and large scale spatial cross-talk from the optics) and diffusion (in focus) background from the individual waveguides considered). These backgrounds are generally stable on the timescales of pulses, but still may vary slowly over longer timescales. Baseline removal comprises any number of techniques, ranging from, e.g.: a median of the trace, running lowest-percentile with bias correction, polynomial and/or exponential fits, or low-pass filtering with an FFT. Generally these methods will attempt to be robust to the presence of pulses in the trace and may actually be derived at through iterative methods that make multiple passes at identifying pulses and removing them from consideration of baseline estimation.

Other baselining functions include correction for drift or decay of overall signal levels. For example, photobleaching of organic material sometimes present on the back of the waveguide array is believed to cause decay in the level of background, and thus result in a decreasing baseline over time. This same global background decay is present on portions of the substrate at which there is no waveguide, thus allowing the traces derived from these locations to be used in combination with the two dimensional global background image to estimate the contribution of this signal to every trace/channel across the chip. This component of variability can then be subtracted from each trace and is usually very effective at removing this decay. Typically, this is carried out prior to the baselining processes described above.

As shown, each trace's baseline is established at step 900. Following establishment of the baseline the traces are subjected to noise suppression filtering to maximize pulse detection (step 902). In particularly preferred aspects, the noise filter is a 'matched filter' that has the width and shape of the pulse of interest. While pulse timescales (and thus, pulse widths) are expected to vary among different dye labeled nucleotides, the preferred filters will typically look for pulses that have a general "top-hat" shape with varying overall duration. As such, a boxcar filter that looks for a pulse of prolonged duration, e.g., from about 10 ms to 100 or more ms, provides a suitable filter. This filtering is generally performed in the time-domain through convolution or low-pass frequency domain filtering. Other filtering techniques include: median filtering (which has the additional effect of removing short timescale pulses completely from the trace depending on the timescale used), and Savitsky-Golay filtering which tends to preserve the shape of the pulse—again depending on the parameters used in the filter).

Although described in terms of a generic filtering process across the various traces, it will be appreciated that different spectral traces may have different characteristics, and thus may be subjected to trace specific filtering protocols. For example, in some cases, a given dye labeled analog (e.g., A) may have a different pulse duration for an incorporation event than another different dye labeled analog (e.g., T). As such, the filtering process for the spectral trace corresponding to the A analog will have different filtering metrics on the longer duration pulses, than for the trace corresponding to the T analog incorporation.

In identifying pulses on a filtered trace, a number of different criteria may be used. For example, one could use absolute pulse height, either with or without normalization. Alternatively, one could identify pulses from the pulse to diffusion background ratio as a metric for identifying the pulse. In still other methods, one may use statistical significance tests to identify likely pulses over the background noise levels that exist in a given analysis. The latter method is particularly preferred as it allows for variation in potential pulse intensities, and reduces the level of false positives called from noise in the baseline.

As noted previously, a number of signal parameters may be and generally are used in pulse identification (as well as in pulse classification). For purposes of illustration, however, the process illustrate in the flow chart of FIG. 9 focuses primarily on the use of two main pulse metrics, namely pulse intensity and pulse width. As will be appreciated, the process steps at step 906 and 908 may generally include any one or more of the various pulse metric comparisons set forth elsewhere herein.

As such, following filtering, standard deviation of the baselines (noise and pulses) is determined at step 904. Preferred methods for determining the standard deviation of a trace include robust standard deviation determinations including, e.g., being based upon the median absolute difference about the baseline, a Gaussian or Poisson fit to the histogram of baselined intensities, or an iterative sigma-clip estimate in which extreme outliers are excluded. Once determined for each trace, a pulse is identified if it exceeds some preset number of standard deviations from the baseline, at step 906. The number of standard deviations that constitute a significant pulse may vary depending upon a number of factors, including, for example, the desired degree of confidence in identification or classification of significant pulses, the signal to noise ratio for the system, the amount of other noise contributions to the system, and the like. In a particularly preferred aspect, the up-threshold for an incorporation event, e.g., at the initiation of a pulse in the trace, is set at about 5 standard deviations or greater, while the down-threshold (the point at which the pulse is determined to have ended) is set at 1.25 standard deviations. The pulse width is then determined from the time between the up and down thresholds at step 910. Once significant pulses are initially identified, they are subjected to further processing to determine whether the pulse can be called as a particular base incorporation event at step 912, and as described in greater detail, below.

In some cases, multiple passes are made through traces examining pulses at different timescales, from which a list of non-redundant pulses detected at such different time thresholds may be created. This typically includes analysis of unfiltered traces in order to minimize potential pulse overlap in time, thereby maximizing sensitivity to pulses with width at or near the highest frame rate of the camera. This allows the application of pulse shape or other metrics to pulses that inherently operate on different timescale. In particular, an analysis at longer timescales may establish trends not identifiable at shorter timescales, for example, identifying multiple short timescale pulses actually correspond to a single longer, discrete pulse.

In addition, some pulses may be removed from consideration/evaluation, where they may have been identified as the result of systematic errors, such as through spatial cross-talk of adjacent waveguides, or spectral cross-talk between detection channels for a given waveguide (to the extent such issues have not been resolved in the calibration processes, supra). Typically, the calibration process will identify spectral and spatial cross-talk coefficients for each waveguide, and thus allow such components to be corrected.

Pulse recognition, e.g., on the one dimensional traces, as described above, may provide sufficient distinction to classify pulses as corresponding to particular dyes, and consequently, particular bases, based purely on their peak height. In most preferred aspects, however, the pulses identified for each waveguide are used to return to the waveguide's spectra to extract individual waveguide's spectra for each pulse for additional pulse metrics and to identify any interfering signal components, such as whether a detected pulse in a trace is due to spectral cross-talk.

D. Pulse Spectrum Extraction and Classification

Classification of an extracted pulse spectrum is then carried out by comparing the extracted spectrum to the spectra of the standard dye sets established in the calibration process. A number of comparative methods may be used to generate a comparative metric for this process. For example, in preferred aspects, a $\chi^2$ test is used to establish the goodness of fit of the comparison. In a particular example, for an extracted pulse spectrum ($S_i$), the amplitude (A) of the fit of an individual dye spectral shape, as measured from the pure dye calibration spectrum, $P_i$, is the only variable to solve and will have a $\chi^2$ value of:

$$\chi^2 = \sum_i \frac{(S_i - AP_i)^2}{V_i}$$

The probability that the pure dye spectrum fits with the extracted spectrum is then derived from the $\chi^2$ probability distribution (with a number of degrees of freedom for the number of data points used, $\nu$).

The classification of a given pulse spectrum is then identified based upon calculating values for each of the four different dyes. The lowest $\chi^2$ value (and the highest probability fit), assigns the pulse to that particular dye spectrum, and the pulse is called as corresponding to that dye.

Again, other techniques may be employed in classifying a pulse to a particular spectrum, including for example, measuring correlation coefficients for each of the 4 possible dyes for the spectrum, with the highest correlation providing the indication to which base or dye the pulse will be classified.

In addition to comparison of the pulse spectra to the calibration spectra, a number of other pulse metrics may be employed in addition to a straight spectral comparison in classifying a pulse as correlating to a given dye/nucleotide. In particular, in addition to the spectral properties associated with a given dye, signals associated with incorporation of a given dye labeled nucleotide typically have a number of other characteristics that can be used in further confirming a given pulse classification. For example, and as alluded to above, different dye labeled nucleotides may have different characteristics such as pulse arrival time (following a prior pulse), pulse width, signal intensity or integrated counts (also referred to as pulse area), signal to noise ratio, power to noise ratio, pulse to diffusion ratio (ratio of pulse signal to the diffusion background signal in each waveguide), spectral fit (e.g., using a minimum $\chi^2$ test, or the like), spectrum centroid, correlation coefficient against a pulse's classified dye, time interval to end of preceding pulse, time interval to the ensuing pulse, pulse shape, polarization of the pulse, and the like.

In particularly preferred aspects, a plurality of these various pulse metrics are used in addition to the spectral comparison, in classifying a pulse to a given dye, with particularly preferred processes comparing two, three, five, 10 or more different pulse metrics in classifying a pulse to a particular dye/nucleotide.

E. Base Calling

Figure 10:
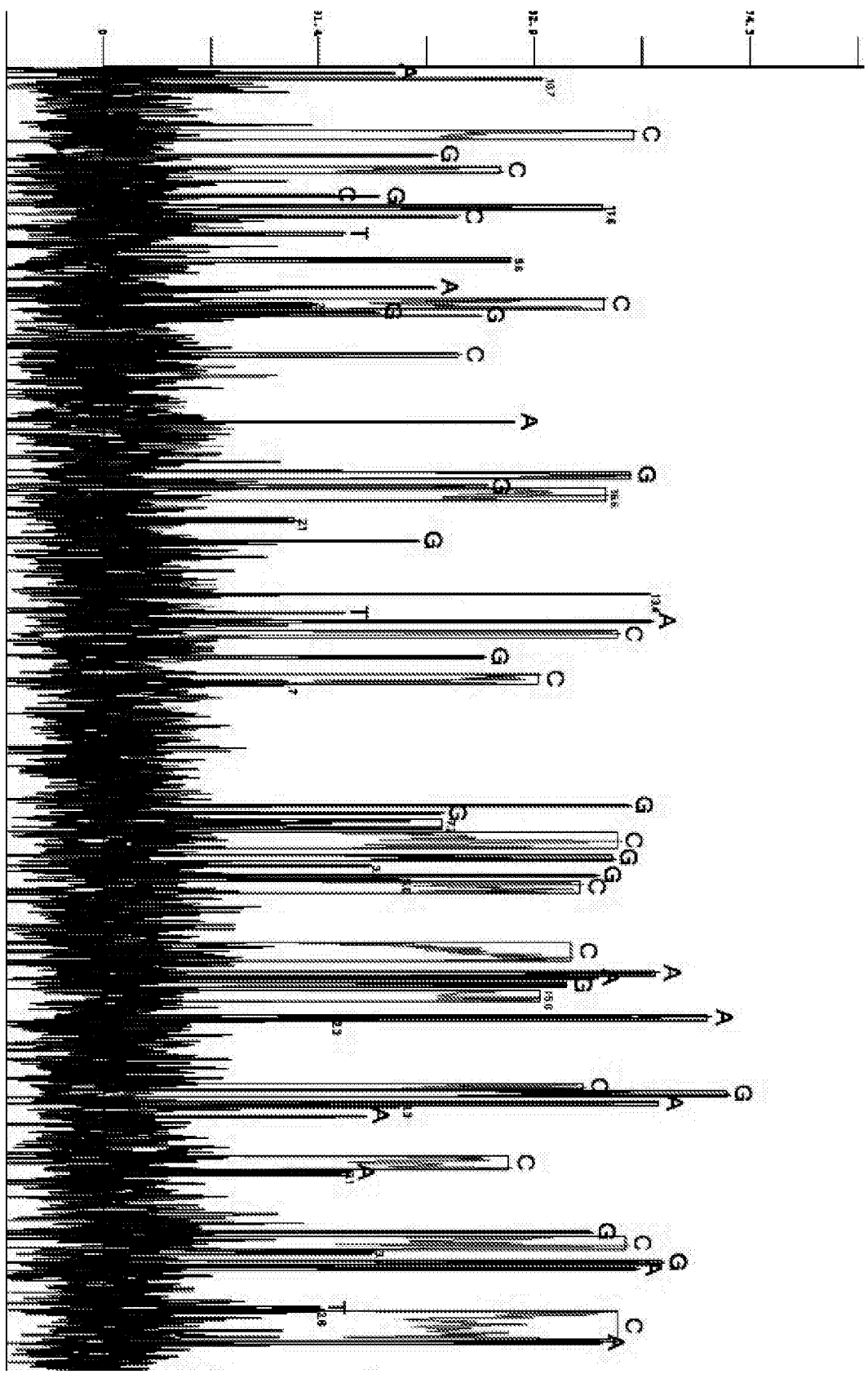
FIG. 10 illustrates an integrated trace following base classification of a pulse trace, including base calls.
Figure 11:
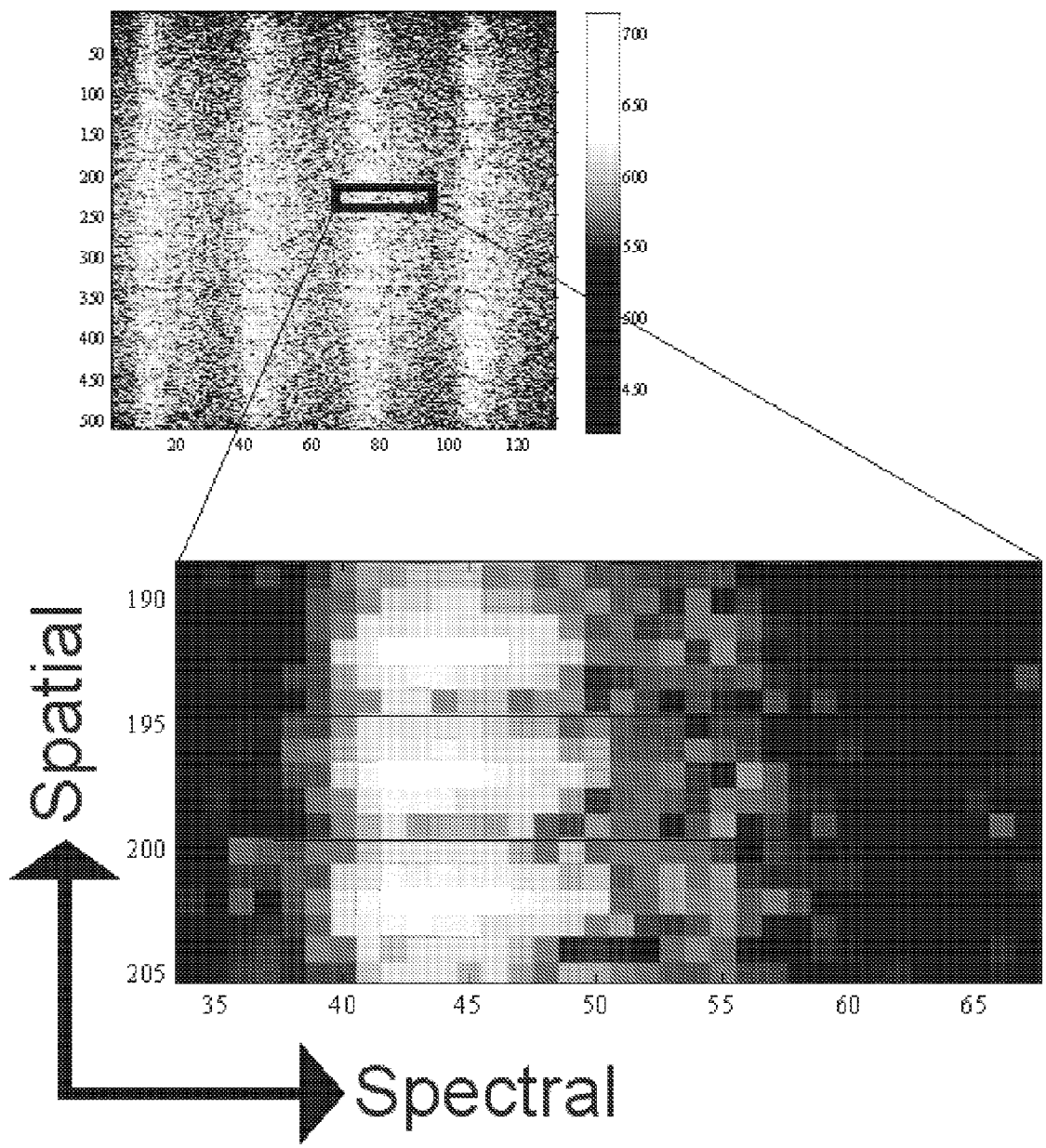
FIG. 11 is a spectral reference pixel image of a trans-illuminated array of zero mode waveguides according to specific embodiments of the invention.

Once the pulse spectrum is classified as corresponding to a particular dye spectrum, that correlation is then used to assign a base classification to the pulse. As noted above, the base classification or "calling" may be configured to identify directly the dye labeled base added to the extended primer sequence in the reaction, or it may be set to call the complementary base to that added (and for which the pulse spectrum best matches the dye spectrum). In either case, the output will be the assignment of a base to each recognized and classified pulse. An illustration of bases being called or assigned to different pulses is shown in FIG. 10, which shows such pulses on a collapsed timescale.

In an ideal situation, once a pulse is identified as significant and its spectrum is definitively identified, a base could simply be called on the basis of that information. However, as noted above, in typical sequencing runs, signal traces include a substantial amount of signal noise, false positive pulses, e.g., resulting from nonspecifically adsorbed analogs or dyes or the like. Accordingly, pulse classification can in many cases involve a more complex analysis. As with pulse identification, above, base classification typically relies upon a plurality of different signal characteristics in assigning a base to a particular identified significant pulse. In many cases, two, three, five, ten or more different signal characteristics may be compared in order to call a base from a given significant pulse. Such characteristics include those used in identifying significant pulses as described above, such as pulse width, pulse intensity, signal to noise ratio, power to noise ratio, integrated counts in pulse peak, shape of and distance/time to neighboring pulses, spectral signature of the pulse, pulse centroid location, and the like. Typically, such comparison will be based upon standard pattern recognition of the metrics used as compared to patterns of known base classifications, yielding base calls for the closest pattern fit between the significant pulse and the pattern of the standard base profile.

Comparison of pulse metrics against representative metrics from pulses associated with a known base identity will typically employ predictive or machine learning processes. In particular, a "training" database of "N previously solved cases" is created that includes the various metrics set forth above. From that database, a learning procedure is applied to the data in order to extract a predicting function from the data. A wide variety of learning procedures are known in the art and are readily applicable to the database of pulse metrics. These include, for example, linear/logistic regression algorithms, neural networks, kernel methods, decision trees, multivariate splines (MARS), support vector machines. Further, employing machine learned meta-algorithms for performing supervised learning, or "boosting" may be applied to any of the foregoing processes or any combinations of those. Briefly, such boosting incrementally adds to the current learned function. At every stage, a weak learner (i.e., one that yields an accuracy only slightly greater than chance) is trained with data, and that output is added to the learned function with some strength (proportional to how accurate the weak learner is. The data is then reweighted. Identifications that the current learned function has missed are then boosted in importance so that subsequent weak learners may be applied to attempt to correct the errors. Examples of boosting algorithms include, for example, AdaBoost, LPBoost, TotalBoost, and the like.

As will be appreciated, and as alluded to previously, assignment or classification of a particular pulse as incorporation of a particular base, e.g., employing the processes above, will typically be based, at least partially, on a desired probability score, e.g., probability that the called base is accurate. As noted, the probability scores for base calling, like PHRED scores for base calling in chromatographically identified bases, will typically take into account the closeness of fit of a pattern of signal metrics to a standard signal profile, based upon a plurality of different signal characteristics that include those elements described elsewhere herein, including the signal environment around a given pulse being called as a particular base, including adjacent pulses, adjacent called bases, signal background levels, pulse shape (height or intensity, width or duration, etc.), signal to noise ratios, and other signal contributors. Typically, preferred base calls will be made at greater than the 90% probability level (90% probability that the called base is correct), based upon the probability evaluation, preferably, greater than 95% probability level, more preferably greater than 99% probability, and even more preferably, greater than 99.9% or even 99.99% probability level.

The processes of the invention will typically be integrated with sequence arrangement processes for arranging and outputting the individual called bases into a linear sequence, and outputting such data to the user in any of a variety of convenient formats. Additionally, such processes will optionally verify and correct such sequence data based upon iterative sequencing of a given template, multiple sampling of overall sequence fragments through the sequencing of overlapping templates, and the like, to provide higher confidence in sequence data obtained.

A number of other filtering processes may be used in the overall evaluation of data from sequencing by incorporation reactions as discussed herein. For example, a number of filtering processes may be employed to identify signal sources or waveguides that are yielding the highest quality level of data, e.g., resulting from a single fully functional polymerase/template/primer complex, immobilized on the bottom surface of the waveguide. These filters may rely upon a number of the metrics described above. Alternatively, these filters may employ holistic characteristics associated with a long time scale showing a large number of pulses, and determining whether the longer timescale metrics of the traces have characteristics of a typical sequence by incorporation trace, e.g., relatively regular, high confidence (based upon one or a number of relevant pulse metrics) pulses coming out over the course of the trace, yielding a "picket fence" appearance to the trace. Alternatively, additional components may be introduced to the reactants, e.g., labeling of the complexes, to facilitate their identification in the filtering process. As such, the existence of the indicator would be an initial filter to apply to any waveguide's data traces.

Although described in some detail for purposes of illustration, it will be readily appreciated that a number of variations known or appreciated by those of skill in the art may be practiced within the scope of present invention. To the extent not already expressly incorporated herein, all published references and patent documents referred to in this disclosure are incorporated herein by reference in their entirety for all purposes.

FURTHER EXAMPLE EMBODIMENT

In order to further illustrate the invention, details are provided below regarding data collection and data analysis related to particular example sequencing systems. The details below are provided as a further example of embodiments of the invention and should not be taken to limit the invention. In some sequencing systems of interest, the relative weakness of detected signals, the levels of noise, the very small feature sizes of the reaction locations, and the speed and variation of the incorporation reaction, present challenges for signal data analysis and base-calling. These challenges are addressed by a number of novel data analysis methods and systems according to specific embodiments of the invention.

Example of Raw Data from an Array of Reaction Locations

In order to better illustrates aspects of particular embodiments of the invention, characteristics of an example set of captured data are briefly described. An particular example system of the type illustrated in FIG. 1 can be further understood as follows. Substrate 102 is an ordered arrangement (e.g., an array) of reaction locations and/or reaction wells and/or optical confinements and/or reaction optical sources 104. Detector/camera 116 is an ordered array of optical signal collectors or detectors, such as a CCDs, EMCCDs, or other devices able to detect optical signals and report intensity values. Such devices are well understood in the art and typically are known as able to detect light intensity incident on the detector during a given time interval (or frame) and able to output a numerical intensity value representative of the light intensity collected during a particular interval. Detector 116 will typically include an array of addressable areas, each able to make an intensity measure and data output. The separate areas are commonly referred to as pixels. Each pixel generally has an address or coordinate (e.g., x, y) and outputs one or more intensity levels for a given interval or frame. Pixels that output only one intensity level are sometimes referred to as gray-scale or monochrome pixels. A static pixel array of light intensity values (e.g., generally for one interval) is commonly referred to as an image or frame. A time sequence of frames is referred to as a movie.

A detector/camera such as 116 may be capable of only the most basic functions necessary to capture and output intensity levels. Alternatively, a detector/camera such as 116 may include or be associated with logic circuitry able to perform various optical adjustments and/or data collection and/or data manipulation functions such as adjusting frame rate, correcting for noise and/or background, adjusting alignment or performing tracking, adjusting pixel size, combining indicated pixels prior to output, ignoring or filtering indicated pixels, etc. Thus, the raw data available from a detector 116 typically can be understood as a sequence of 2-dimensional arrays of pixel values at a particular frame rate. In an example system as in FIG. 1, the raw pixel data is mono-chrome. FIG. 2 is an example of a single frame or image of monochrome raw data captured by detector 116. In specific embodiments of the present invention, detector 116 captures and outputs 1 frame each 10 milliseconds (or 100 frames per second (f.p.s.)).

Data from One Reaction Location/Optical Source

While the present invention is generally directed to collection of data from many optical sources in parallel, some aspects of the invention are better understood with reference to data captured from a single optical source. In specific embodiments, the optical signal (or light) from one location 102 will pass through an optical train including a spectral spreading or refracting component such as prism 112 and lens 114. In a specific embodiment, the optical signal from one location 102 will generally be imaged on and detected by a rectangular to nearly rectangular area of pixels on detector 116. One dimension or axis (typically the longer dimension) is primarily due to spectral refraction and is herein referred to as the spectral axis. The other dimension (typically the shorter dimension) is referred to as the spatial axis. This axis is defined as the axis orthogonal to the spectral axis and is primarily due to the point source spread onto detector 116 through the optical train from location 102. In many preferred implementations the spatial axis will be reduced to one pixel or a few pixels using one or more known combination techniques, such as a point spread function (PSF) analysis. This reduction may be performed before or after data collection from the optical system as described below. In some example embodiments, the raw-data spectral dimension for one imaged location 102 is about 8 pixels to about 20 or more pixels. However, this value can vary widely as a result of the minimum size of pixels available in a detector 116 or other optical component and could feasibly range in the 100s or 1000s. In some example embodiments, the raw-data spatial dimension for one imaged location 102 is about 3 pixels to about 5 pixels. However, this value can also vary widely as a result of the minimum size of pixels available in a detector 116 or other optical component and could feasibly range in the 100s or 1000s. In some example embodiments, the frame-rate for raw captured images is about 100 frames per second (f.p.s.). However, this value could also vary widely depending on desired characteristics of the system and available computational and/or optical components.

Analysis of Arrays of Reaction Locations

In specific embodiments, data capture and data analysis according to the present invention includes many novel elements related to analyzing a large number of individual sequencing reactions located in an array of reaction locations or optical confinements. The invention, in specific embodiments, addresses the difficulties that arise in such a system and takes advantage of the unique properties of the data arising from such a system.

Figure 12:
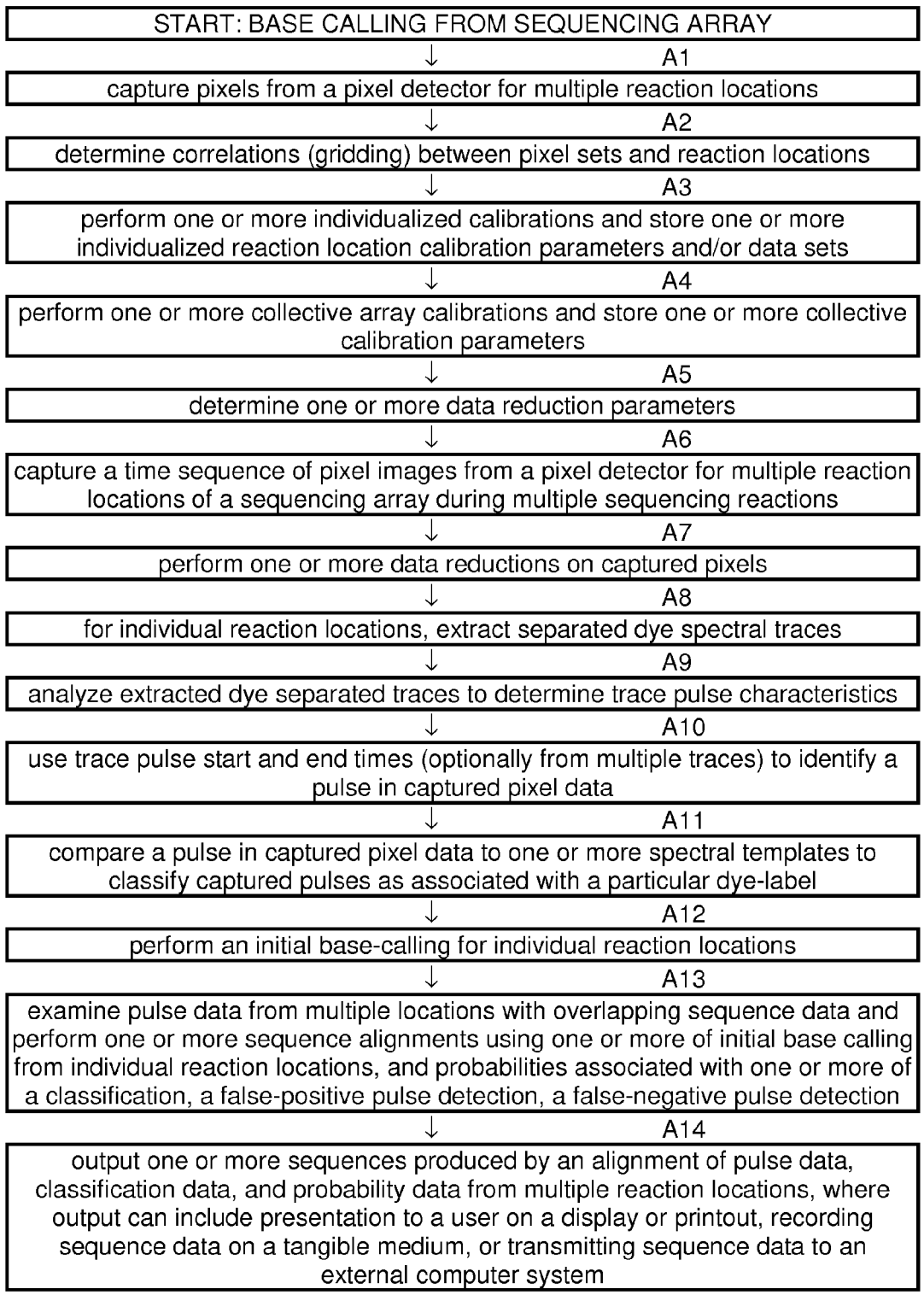
FIG. 12 is a flow chart illustrating an example method of base calling from a sequencing array using a logic processing system according to specific embodiments of the invention.

FIG. 12 is a flow chart illustrating an example method of base calling from a sequencing array using a logic processing system according to specific embodiments of the invention. This figure illustrates a number of steps that are explained in greater detail below. Not all of these steps will be performed in all embodiments. In general terms, data capture and analysis involves: capturing pixels from a pixel detector for multiple reaction locations of a sequencing array (Step A1); determining correlations (gridding) between pixel sets and reaction locations (Step A2); performing one or more individualized calibrations and storing one or more individualized reaction location calibration parameters and/or data sets (Step A3); performing one or more collective array calibrations and storing one or more collective calibration parameters (Step A4); determining one or more data reduction parameters (Step A5); capturing a time sequence of pixel images from a pixel detector for multiple reaction locations during multiple incorporation reactions (Step A6); performing one or more data reductions on captured pixels (Step A7); for individual reaction locations, extracting separated dye spectral traces (Step A8); analyzing extracted dye separated traces to determine significant trace pulses and trace pulse characteristics or optionally to exclude locations with traces indicating poor quality reaction data (Step A9); using trace pulse start and end times (optionally from multiple traces) to identify a pulse in captured pixel data (Step A10); comparing a pulse in captured pixel data to one or more spectral templates to classify captured pulses as associated with a particular dye-label (Step A11); performing an initial base-calling for individual reaction locations (Step A12); examining pulse data from multiple reaction locations with overlapping sequence data and perform one or more sequence alignments using one or more of initial base calling from individual reaction locations, and probabilities associated with one or more of a classification, a false-positive pulse detection, a false-negative pulse detection (Step A13); outputting one or more consensus sequences produced by an alignment of pulse data, classification data, and probability data from multiple reaction locations, where output can include presentation to a user on a display or printout, recording sequence data on a tangible medium, or transmitting sequence data to an external computer system) (Step A14).

Figure 13:
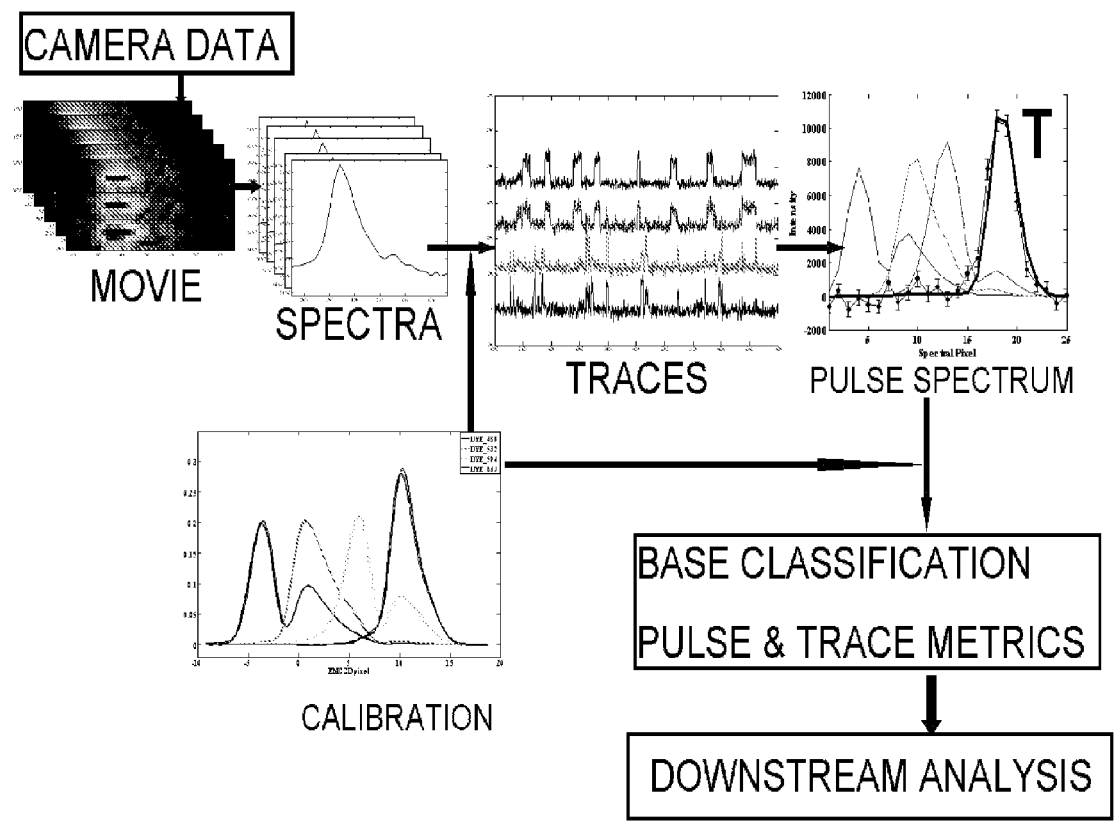
FIG. 13 is a diagram illustrating an example method of base calling from a sequencing array using a logic processing system according to specific embodiments of the invention.

Analysis of sequencing-by-incorporation-reactions on an array of reaction locations according to specific embodiments of the invention is also illustrated graphically in FIG. 13. In this summary figure, data captured by a CAMERA is represented as a MOVIE, which is also a time sequence of SPECTRA. Spectral CALIBRATION templates are used to extract TRACES from the spectra. Pulses identifies in the traces are then used to return to the SPECTRA data and from that data produce a temporally averaged PULSE SPECTRUM for each pulse. The Spectral CALIBRATION templates are then also used to classify PULSE SPECTRUM to a particular base. Base classifications and pulse and trace metrics are then stored or passed to other logic for further analysis.

Calibrations

Typically, various adjustments or calibrations are made in digital imaging systems both prior to and during image capture. These adjustments can include such things as determining and correcting for background noise or various distortions caused by the optical and/or digital capture components, adjusting frame or shutter speed based on intensity levels, adjusting contrast in reported intensity levels, etc. Various such calibrations or adjustments may be made according to specific embodiments of the invention so long as the adjustments to not interfere with the data analysis as described below. Calibrations particular to specific embodiments of the present invention are described in more detail herein. Some of these calibration steps described herein may be performed periodically (such as once a week or once a day), other calibrations may be performed once at the beginning of a sequencing reaction data capture and analysis, and some calibrations are performed on a more continuous basis, throughout or at intervals during a reaction capture and analysis. These calibration steps can include such things as centroid determination, alignment, gridding, drift correction, initial background subtraction, noise parameter adjustment, spectral calibration, frame-rate adjustment, etc. Some calibration steps, such as binning, may involve communication from the processor back to the detector/camera, as discussed further below.

Gridding

An initial step in analyzing data from a system such as illustrated in FIG. 1 is determining which sets of pixels of detector 116 correspond to individual reaction locations 104. (In some implementations, this step could be addressed in the construction of the system, so that detectors and reaction locations are manufactured to have a fixed association.) Gridding, in particular embodiments, is an initial identification of particular reaction locations with particular areas of pixels in an image. According to specific embodiments of the invention, imaged signals are correlated to the known spacing of image sources on the waveguide array. Optionally, one or more registration marks incorporated into the array can be used. For example, in preferred aspects, rows of waveguides in an array will include one or more blank spaces in place of a waveguide, where the blanks will be spaced at regular, known intervals. Other registration marks might include regularly spaced image sources that are separate from the waveguides, but are at known locations and spacing relative to the waveguides in the array to permit alignment of the image to the array. Such image sources may include apertures like waveguides, or may include fluorescent or luminescent marks that provide a signal. Gridding in generally accomplished with an illuminated reference frame.

Determining Individualized Sub-Pixel Reference Centroids

Figure 14:
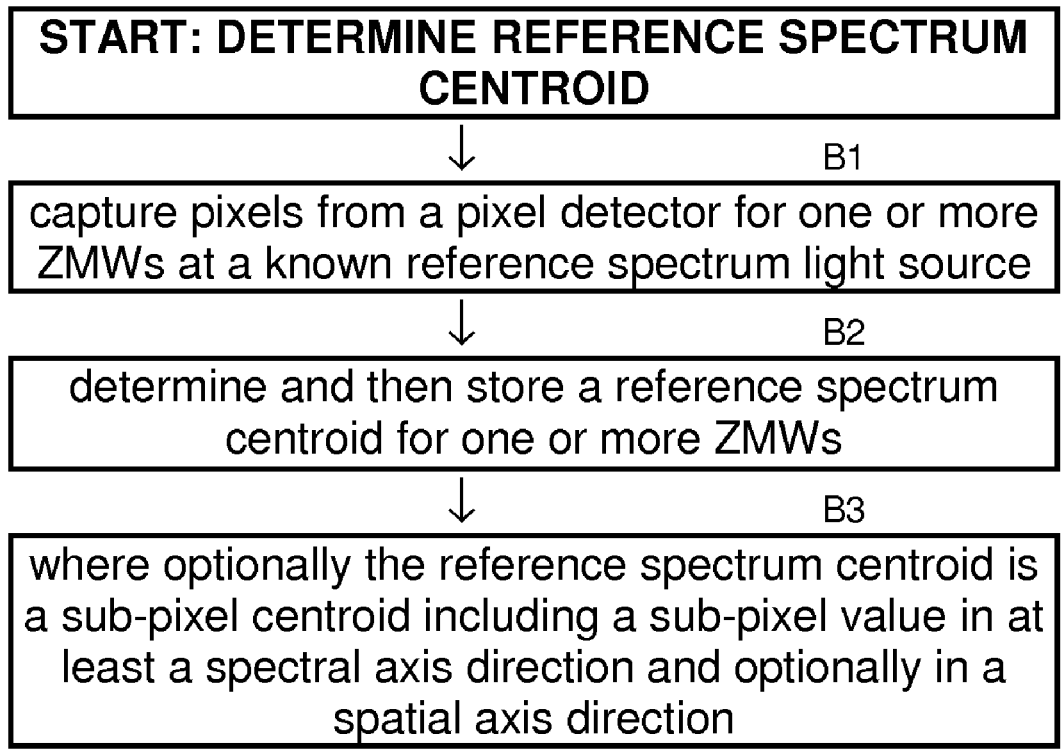
FIG. 14 is a flow chart illustrating an example method of determining a reference spectral centroid for a reaction location image according to specific embodiments of the invention.
Figure 15:
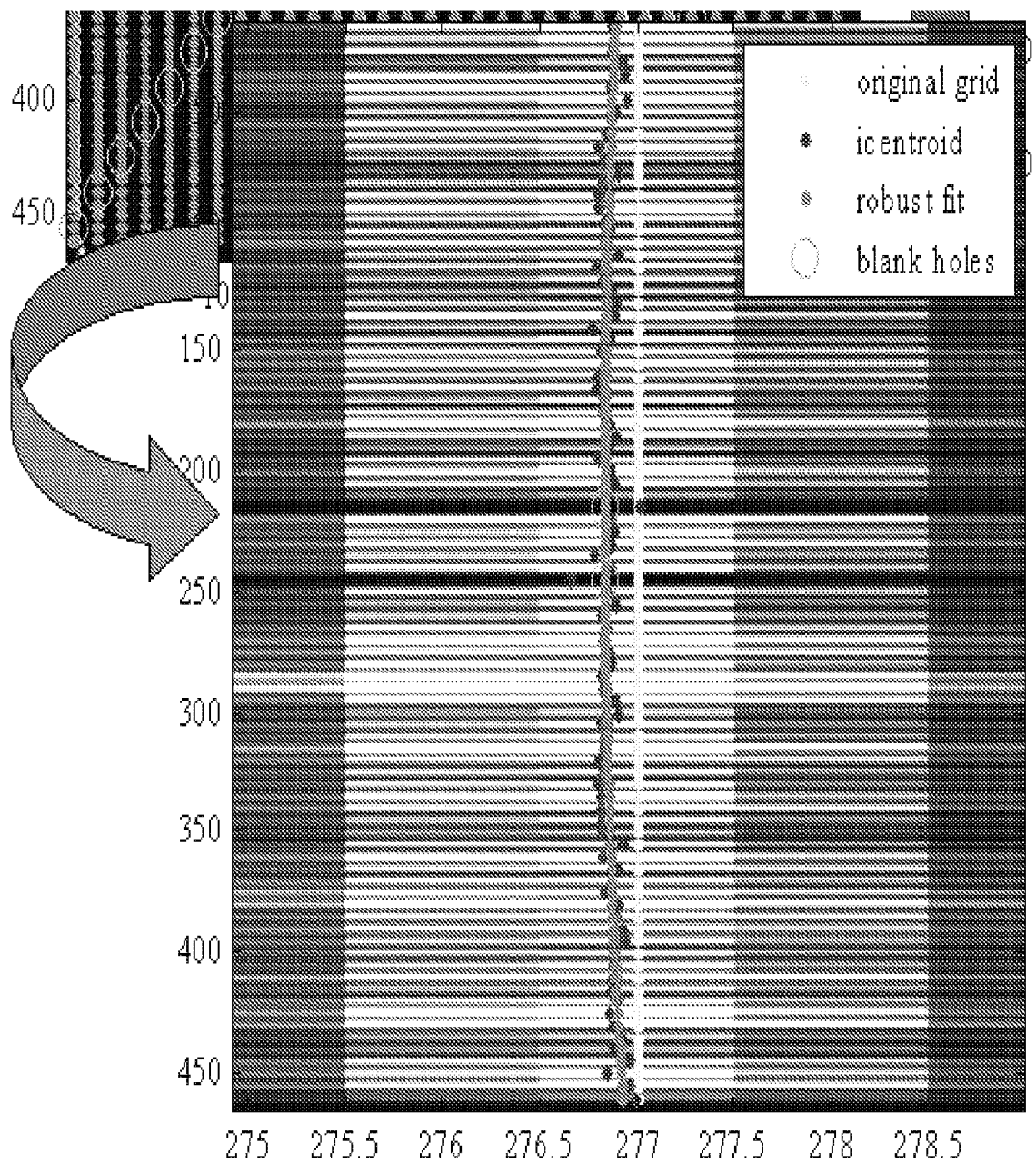
FIG. 15 is a diagram illustrating an initial gridding step and corrected centroids according to specific embodiments of the invention.

According to specific embodiments of the invention, after a initial association of pixel areas in an image with particular ZMWs (gridding), an individualized reference centroid is determined and stored for each or nearly each ZMW. This centroid is determined by finding the geometric center or Gaussian center from a known spectrum, high SNR, narrow band light source that is imaged on detector 116 through generally the same optical train as sequencing reaction optical signals. With reference to FIG. 1, the illumination is directed through the partially transparent waveguides 104 and then through the optical train. Note that, while pixel address locations are generally integer values, formulas for determining a Gaussian center provide a decimal result. Using an accurate illumination through generally the exact optical path allows determination of a subpixel reference centroid by using a selected number of decimal positions from the Gaussian center provide a decimal result. The reference sup-pixel centroid is stored for each ZMW and used as described further below. In specific embodiments, trans-illumination is provided by a light source with a narrow band-pass filter (e.g., 543 nm) or by a narrow band light source, such as an 730 nm light source. In an example embodiment, the subpixel reference centroid is rounded to a closest 0.1 interval. This subpixel reference centroid may then be used to estimate sub-pixel centroids for one or more detection signals as described herein. FIG. 14 is a flow chart illustrating an example method of determining a reference spectral centroid for a reaction location image according to specific embodiments of the invention. FIG. 15 is a diagram illustrating an initial gridding step and corrected centroids according to specific embodiments of the invention. In this figure, the central white line down the center of pixel 277 indicates centroid locations as determined by an initial gridding step. The individual dots to the left of this line indicate individually determined centroids for each ZMW as discussed above. The spline through these individual dots indicates an optionally spline fitting or similar step that can be used to smooth centroid locations and provide a smoothed individualized sub-pixel centroid.

Alignment Across Multiple Reaction Locations

Figure 16:
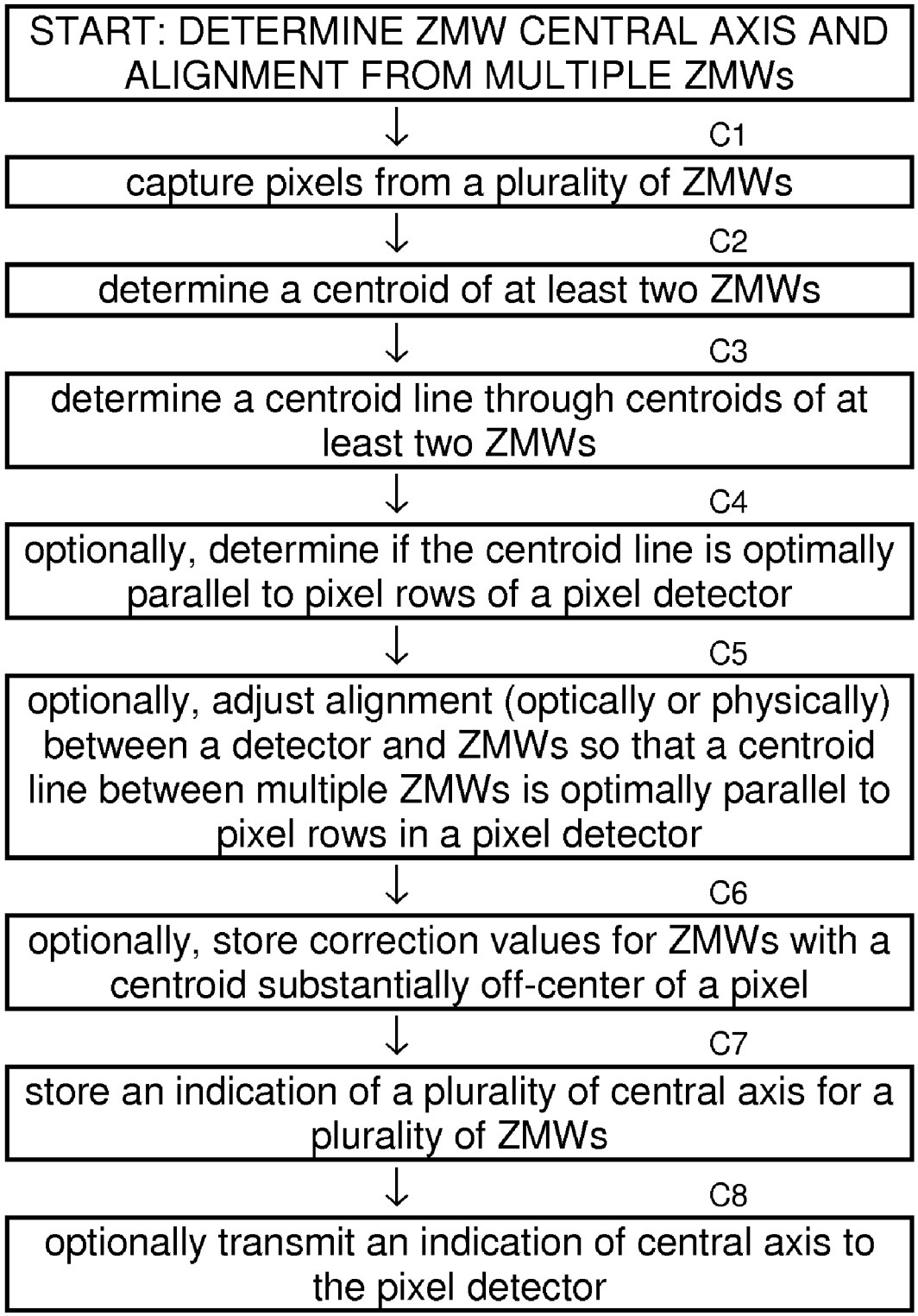
FIG. 16 is a flow chart illustrating an example method of determining an alignment for reaction locations and a central axis for individual reaction locations from multiple reaction location images according to specific embodiments of the invention.

FIG. 16 is a flow chart illustrating an example method of determining an alignment for reaction locations and a central axis for individual reaction locations from multiple reaction location images according to specific embodiments of the invention. After the initial gridding step and determination of a sub-pixel centroid effectively in the spatial axis, an alignment along a spatial axis may be performed to more accurately determine a location of a sub-pixel centroid in the spectral axis. This generally involves capturing pixels from a plurality of ZMWs (Step C1); determining a sub-pixel centroid of at least two ZMWs (Step C2); determining a centroid line through centroids of at least two ZMWs (Step C3); optionally, determining if the centroid line is optimally parallel to pixel rows of a pixel detector (Step C4); optionally, adjusting alignment (optically or physically) between a detector and ZMWs so that a centroid line between multiple ZMWs is optimally parallel to pixel rows in a pixel detector (Step C5); optionally, storing correction values for ZMWs with a centroid substantially off-center of a pixel (Step C6); storing an indication of a plurality of central axes for a plurality of ZMWs (Step C7); optionally transmitting an indication of binning parameters for each ZMW to the pixel detector (Step C8).

Individualized Spectral Templates and Spectral Calibration

Figure 17:
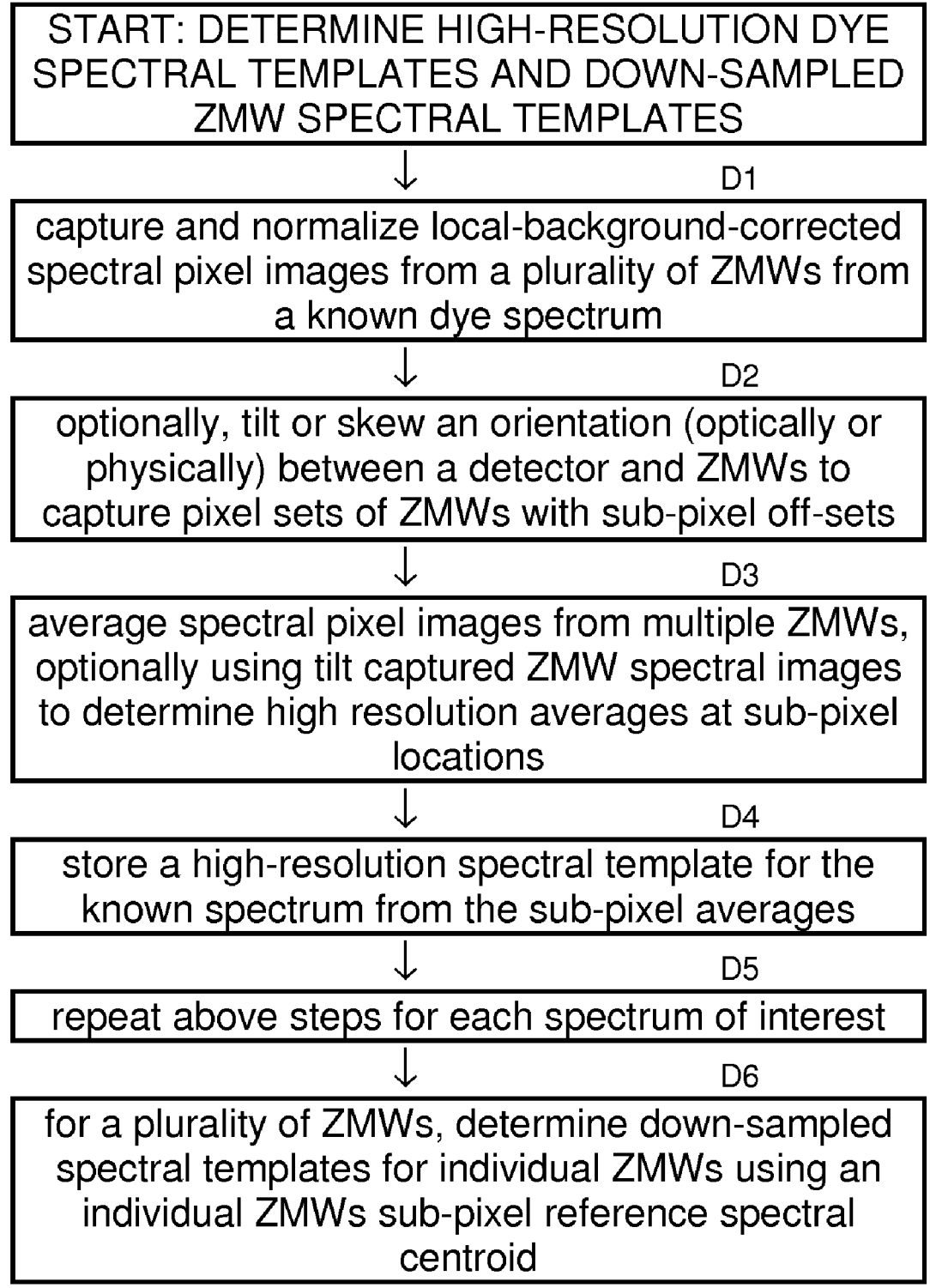
FIG. 17 is a flow chart illustrating an example method of determining high-resolution dye spectral templates and down-sampled individualized spectral templates according to specific embodiments of the invention.

FIG. 17 is a flow chart illustrating an example method of determining high-resolution dye spectral templates and down-sampled individualized spectral templates according to specific embodiments of the invention. In order to provide a more accurate spectral trace extraction and spectral classification, a high resolution spectral template is optionally produced using multiple ZMWs. During spectral calibration, the waveguide array is provided with a standard reference label that may include each pure dye, a pure labeled nucleotide, or another relevant pure component, e.g., a polymerase/template/primer-complexed labeled nucleotide. The signal of each pure label compound is then imaged upon the detector using an optical train and its location is mapped. This is repeated for each different label that is to be used in a reaction. The result is a spectral template or map for the various different labels to be used in a sequencing operation. Calibration spectra may be taken at different locations on a waveguide array than analytical reads and are then aligned to the different locations on the detector using the centroids of the transillumination image. Typically however the spectra as seen on the detector are coarsely sampled and the spectral shape is sensitive to the subpixel centroid location of the ZMW within the image.

Stitching

Figure 18:
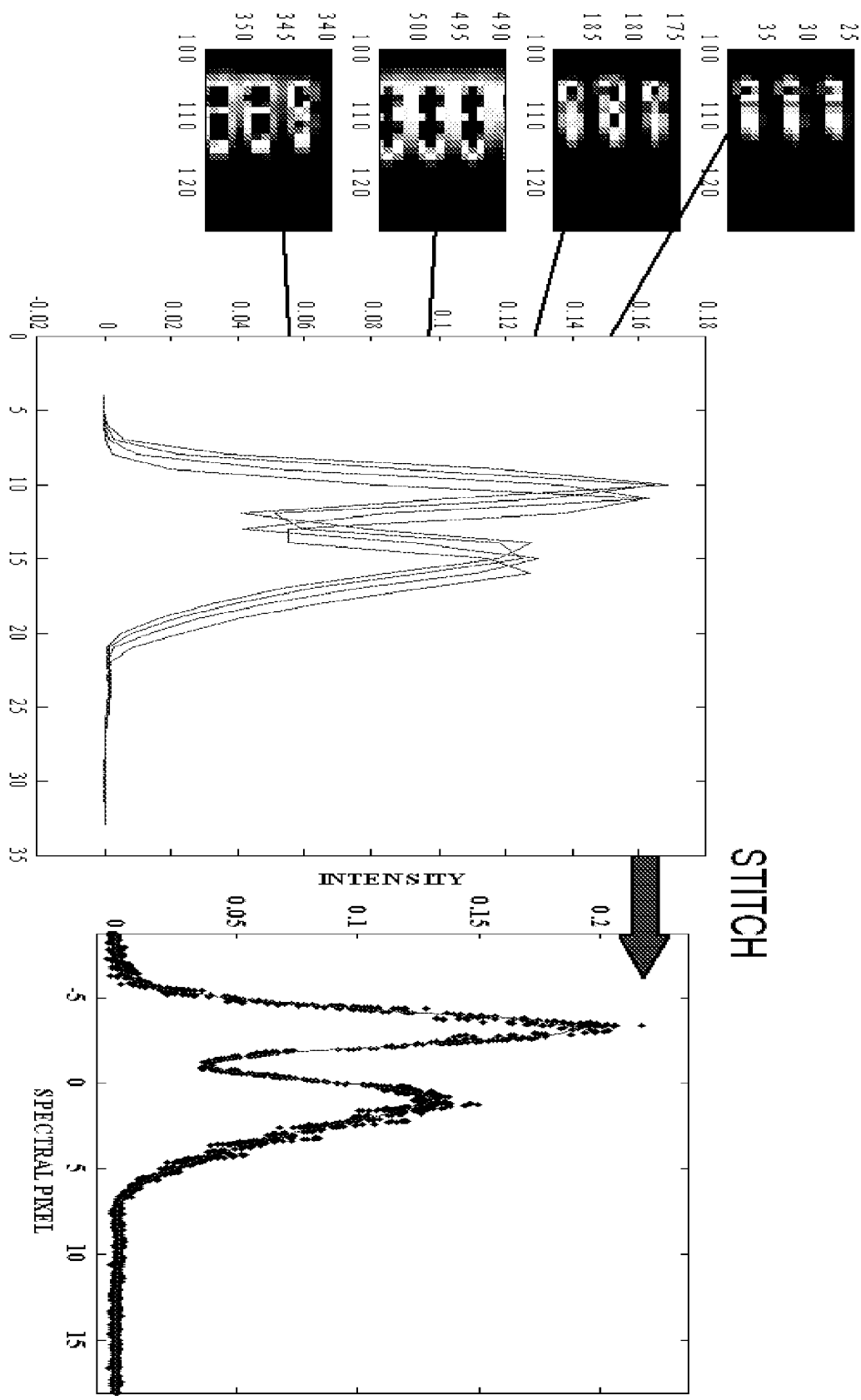
FIG. 18 is a diagram illustrating stitching high-resolution dye spectral templates from multiple captured spectral calibration data according to specific embodiments of the invention.

To improve on estimating this shape accurately the calibration spectra are taken at multiple subpixel centroids, e.g., 0.1 pixels samplings. These can then be combined into a much higher resolution spectrum than a single image can provide. With a subpixel spectral reference centroid estimated from a ZMWs transillumination image, this high resolution spectrum can then be accurately downsampled to account for pixelation of the camera. In addition, due to potential distortions in the optics (e.g. coma, chromatic and spherical aberration) one may also obtain calibration spectra across the field of view of the chip. In this way, unique spectral templates are used from the calibration data for a ZMWs position, thereby accounting for spatially dependent effects that may arise from the optics. In a specific embodiment, an array of ZMWs is mechanically or optically tilted slightly during spectral calibration data collection. The tilting provides a mechanism for capturing calibration spectra with sub-pixel offsets for averaging to provide spectral templates of higher resolution. FIG. 18 is a diagram illustrating stitching high-resolution dye spectral templates from multiple captured spectral calibration data according to specific embodiments of the invention.

One method of accomplishing high resolution calibrations relies on the alignment of reaction locations (e.g., ZMWs) according to specific embodiments of the invention. To understand this, consider a vertical row of 100 ZMWs, each 10 pixels wide along the spectral axis and effectively 1 pixel high in the spatial dimension (although more spatial pixels could be used.). One means of averaging a spectral calibration template of the 100 ZMWs would be to simply average each of the 10 pixel locations separately down the 100 ZMWs. This would provide an averaged spectral template, but not a higher resolution one. Now, however, imagine tilting the vertical row of ZMWs so that the top most ZMW (designated herein as $ZMW_{100}$) was roughly one pixel tilted (e.g., for purpose of discussion, to the right, towards pixels) from the bottom most ZMW, $ZMW_1$. In this case, averages can be taken at sub-pixel locations, where, for example, the leftmost sub-pixel location, $pixel_{0.1}$, will be the average of $pixel_1$ for the 10 lowest ZMWs for that location (e.g., $ZMW_1$ through $ZMW_{10}$). The next sub-pixel, $pixel_{0.2}$, will be the average of a sliding window of 10 ZMWs (e.g., $ZMW_2$ through $ZMW_{11}$ for $pixel_{0.2}$, $ZMW_3$ through $ZMW_{12}$ for $pixel_{0.3}$, etc.). In this example, $pixel_{1.1}$ will be an average of pixel, for 9 ZMWs (e.g., $ZMW_{91}$ through $ZMW_{99}$) and the second pixel for $ZMW_{100}$. In this way, in this example, 100 ZMWs with 10 points of spectral pixel resolution are averaged into one spectral template with 100 points of spectral pixel resolution.

In practice, the spectra taken for $ZWM_1$-$ZWM_{100}$ will in general have their spectral reference wavelength placed at varying sub-pixel shifts, relative to the centroid pixel of the ZMW, because the centroids of the ZMWs will vary more or less uniformly across ~1 pixel. Now, assume that a ZMW centroid can be localized to within ~1/10 pixel as described herein. The ZMW spectra can therefore be characterized as arising from a re-binning of spectra at 10× the resolution, where the higher resolution bin offset is known. The high-resolution spectrum can then be estimated by placing each ZMW spectrum in its corresponding high-resolution bin locations (shift and pitch), and then averaging the values in each bin.

Alternative Spectral Calibration Using Known Segments Added to a Template

In specific embodiments, the generation of high resolution spectral calibration templates is done periodically, such as once a day or once a week, as it involves generally four different rounds of exposing an array 102 to four different dyes, with the overhead of preparation of the array for each of the four different reactions. The high resolution spectral templates are then individualized (and optionally downsampled) using an spectral subpixel centroid, generally during each run. In alternative embodiments, however, a spectral template can be determined for each ZMW for each sequencing reaction by including a series of known bases in a known sequence. In such a case, spectral calibration data for each dye is collected for each ZMW and averaged to provide an individualized ZMW spectral template, optionally using additional relevant data as provided herein.

Determining Background Noise

Figure 19:
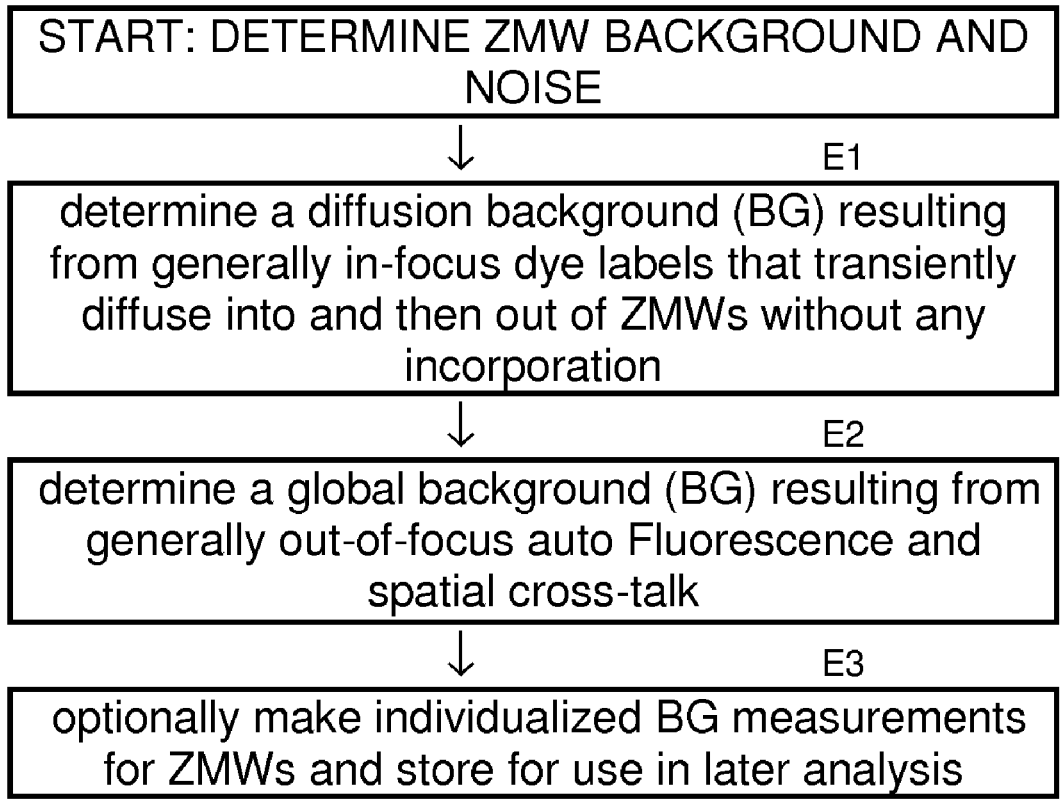
FIG. 19 is a flow chart illustrating an example method of determining background noise for reaction location images according to specific embodiments of the invention.

FIG. 19 is a flow chart illustrating an example method of determining background noise for reaction location images according to specific embodiments of the invention.

Software Spatial Data Reduction

Figure 20:
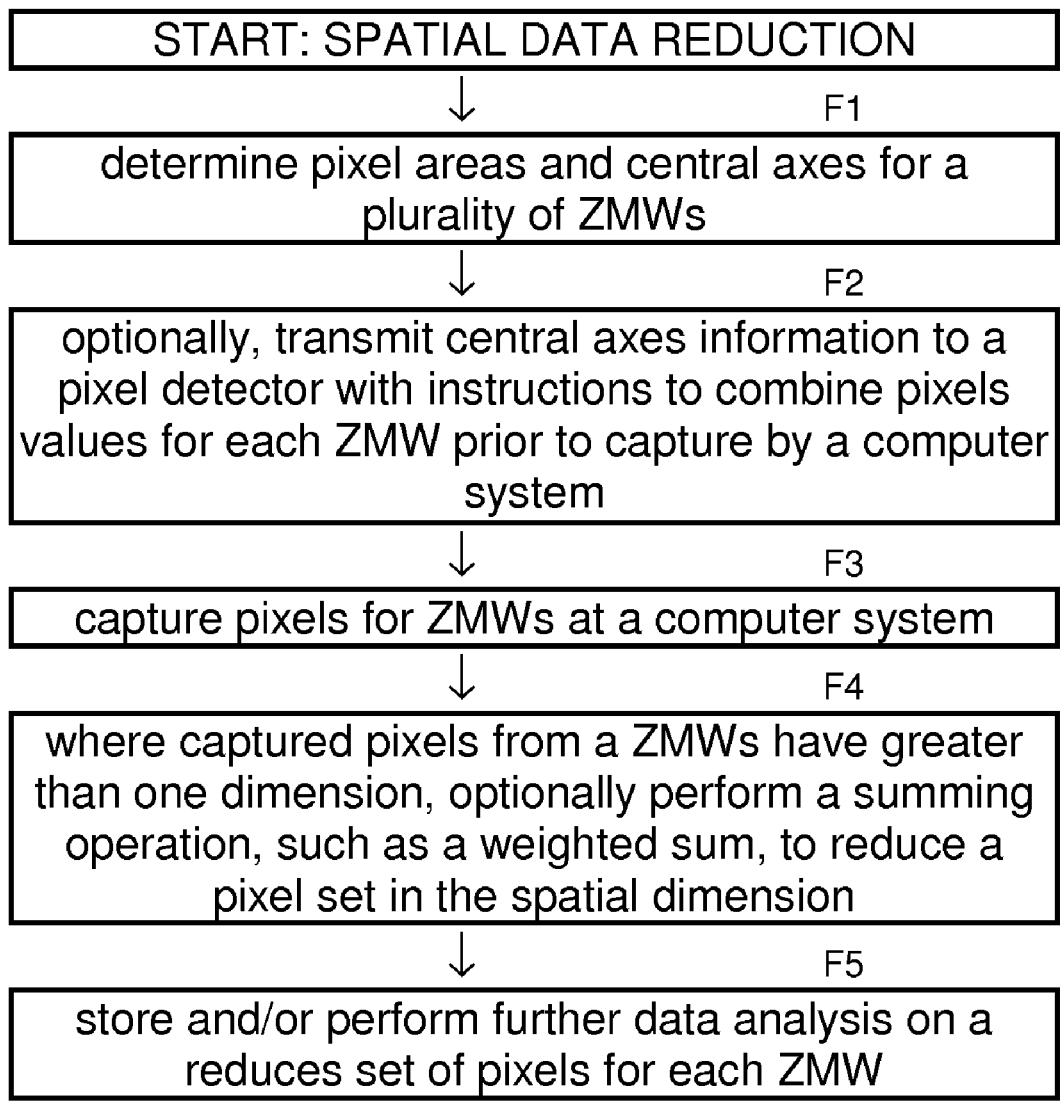
FIG. 20 is a flow chart illustrating an example method of data reduction for a reaction location image according to specific embodiments of the invention.

FIG. 20 is a flow chart illustrating an example method of data reduction for a reaction location image according to specific embodiments of the invention. In specific embodiments, to maximize the signal to noise ratio (SNR) of the extracted spectrum, a weighted sum of pixels along the spatial axis of a ZMW (or reaction location) image area is performed. Weights that maximize the SNR are determined by the inverse variance of each pixel. In an grid array 102 of many reaction locations, optical signal detected from multiple locations can be used to determine a line of pixels through multiple locations, and this line of pixels can be used as the central line for a PSF function. By subtracting adjacent lines an accurate local background correction can be made to leave a one dimensional intensity profile of ZMWs whose shapes are governed entirely by the instrument point spread function. The instrument PSF can be modeled (e.g., by a Gaussian or Moffat function). Fits to the one dimensional profile of a line of ZMWs may solve for all ZMW amplitudes, the ZMW spacing, and a PSF width. These fits can also solve for more parameters (e.g. a polynomial model of PSF width as a function of FOV position) in order to account for second order effects, such as variation of the optical PSF across the field of view (FOV) of the camera or variations in chip (e.g., array substrate 102) geometry.

On-Camera Data Reduction (Binning)

In an alternative extraction process, binning to derive spectral images from each location 104 waveguide is carried out on the camera chip (in a firmware controlled process). In this process, the location of ZMW signals is determined from a full illumination frame, and on-camera (or "on-chip") binning sums (in the spatial direction) only those CCD lines associated with a line of ZMW holes which contains the majority of the signal and reads out only those lines during the actual movie acquisition. This effectively turns output of the CCD from reading out images of waveguides and waveguide arrays, to directly reading out spectral-spread images from the camera chip. As noted previously, by reducing the number of pixels output from the camera over a larger field of view, higher maximum frames rates can be maintained. The optimal binning strategy is the one that maximizes the SNR of pulses from each reaction location.

Spectral Trace Extraction

After the calibration and data reduction steps described above, according to specific embodiments of the invention, the optical signal data for an individual ZMW or location 104 is a sequence or movie of a small area (e.g., an area of about 1×14 pixels) of monochrome spectral-images also referred to herein as spectra. The optical signal data for an individual ZMW can also be understood or represented as a time series of arrays (or vectors) of intensity values (e.g., a sequence of 1 by 14 intensity values). According to specific embodiments of the invention, from these intensity values, one or more spectral traces are extracted for further analysis, e.g., pulse detection. A spectral trace, as used herein, is a time series of generally a single intensity value.

Figure 21:
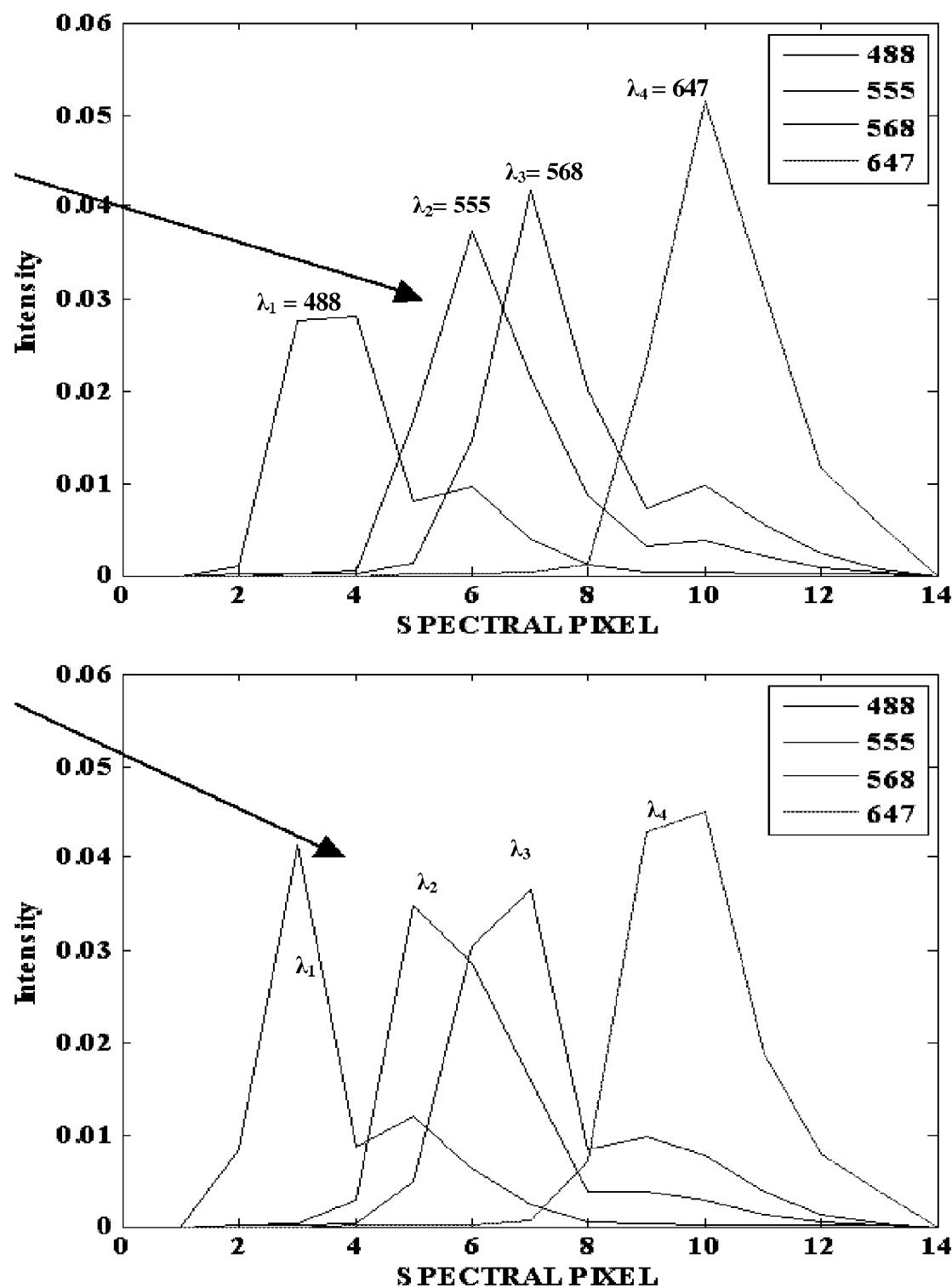
FIG. 21 illustrates an example of four superimposed spectral images representing different dyes imaged from two different reaction locations according to specific embodiments of the invention.

FIG. 21 illustrates an example of four superimposed spectral images representing different dyes imaged from two different reaction locations according to specific embodiments of the invention. FIG. 21 provides some illustration of the nature of the spectral-spread position data and the difficulties in extracting spectral traces that are overcome according to specific embodiments of the invention. The top portion shows four superimposed graphs of 14 pixel values. Each of the four superimposed graphs represents "training data" or "calibration data" from four different known dye spectra at a particular ZMW. Represented numerically, the data at the top portion would approximately be as shown in the table below. For ease of reading, the intensity values shown in the figure are multiplied by 100 in the table below.

TABLE 1

| Dye Spectra | Pixel# | | | | | | | | | | | | | |
| --- | --- | --- | --- | --- | --- | --- | --- | --- | --- | --- | --- | --- | --- | --- |
| | 1 | 2 | 3 | 4 | 5 | 6 | 7 | 8 | 9 | 10 | 11 | 12 | 13 | 14 |
| 488 nm (left most peak) | 0 | 1 | 3 | 2 | 1 | 1 | 0.5 | 0 | 0 | 0 | 0 | 0 | 0 | 0 |
| 555 nm (next peak) | 0 | 0 | 0 | 0 | 1 | 3 | 3 | 1 | 0.5 | 0 | 0 | 0 | 0 | 0 |
| 568 nm (next peak) | 0 | 0 | 0 | 0 | 0.5 | 1 | 4 | 2 | 1 | 0.5 | 0 | 0 | 0 | 0 |
| 647 nm (right most peak) | 0 | 0 | 0 | 0 | 0 | 0 | 0 | 0 | 2 | 5 | 3 | 10 | 5 | 0 |

Figure 22:
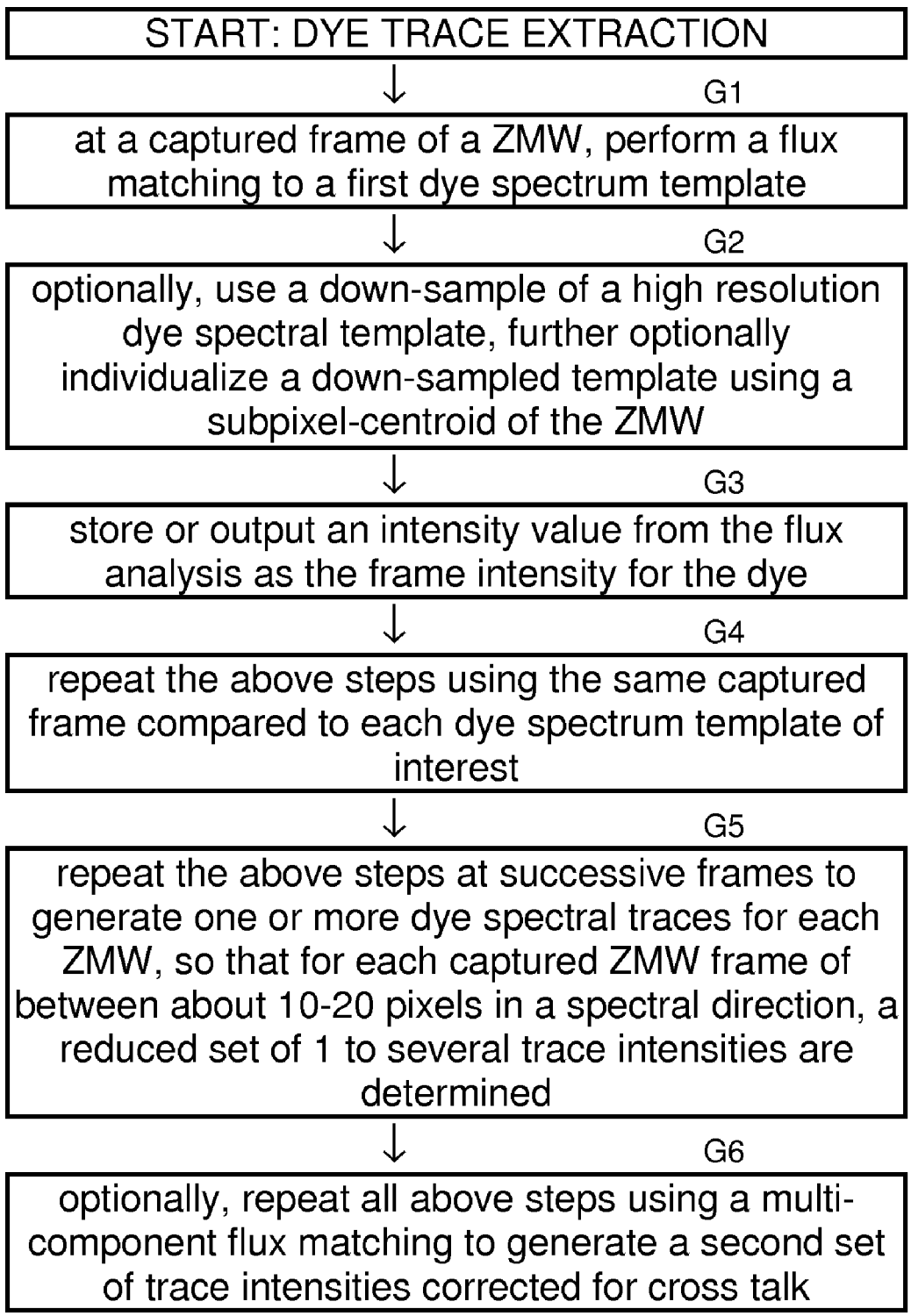
FIG. 22 is a flow chart illustrating an example method of dye trace extraction from a time series of a reaction location images according to specific embodiments of the invention.

The top graph in FIG. 21 indicates one difficulty that is addressed according to specific embodiments of the invention. The figure indicates that even in a situation of "best case" training date, there is can be substantial overlap between the pixel data captured from different dyes, e.g., the 555 and 568 nm dye spectra. In this example, this is to be expected due to the closeness of the wavelengths of the fluorescent signals. However, choice of dye may be constrained for a variety of reasons, and extraction of even closer spectra may be desired in some situations. The bottom graph illustrates another complexity. This figure represents the same data as above, but captured at a different ZMW location. As a result of slight differences in alignment of the true sub-pixel centroid of the ZMW image with the centroid pixel as determined on the detector and/or other slight differences in the optical system, there is variation in the expected data. FIG. 22 is a flow chart illustrating an example method of dye trace extraction from a time series of a reaction location images according to specific embodiments of the invention. The method involves: at a captured frame, performing a flux matching to a first dye spectrum template (Step G1); optionally, using a down-sampled high resolution dye spectral template optionally individualized to a subpixel-centroid (Step G2); storing outputting an intensity value from the flux analysis as the frame intensity for the dye (Step G3); repeating the spectral template comparison on the same captured frame compared for each dye spectrum template (Step G4); repeating the above steps at successive frames to generate one or more dye spectral traces for each ZMW (Step G5); optionally, repeat all above steps using a multi-component flux matching to generate a second set of trace intensities corrected for cross talk (Step G6). Details of this method are described further below.

Figure 23:
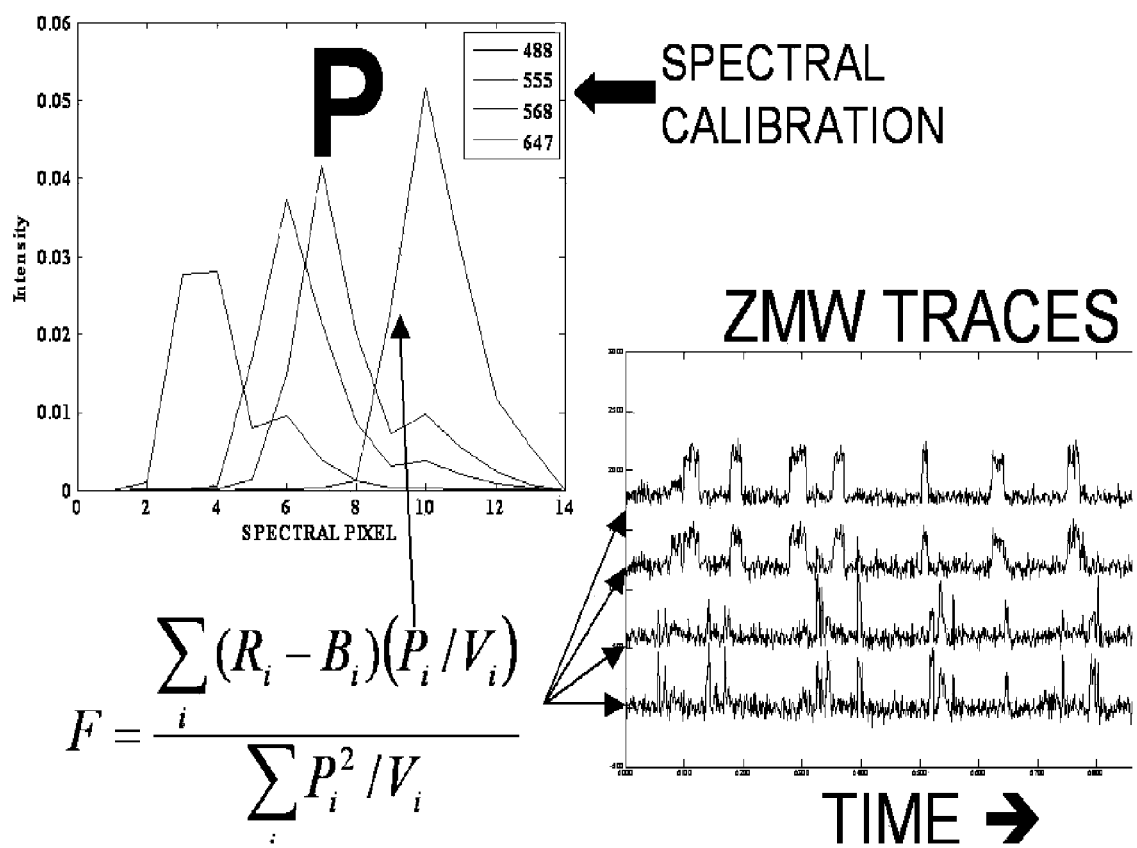
FIG. 23 is a diagram illustrating using an individualized set of spectral templates for a ZMW to extract four spectral traces using a flux calculation according to specific embodiments of the invention.

FIG. 23 is a diagram illustrating using an individualized set of spectral templates for a ZMW to extract four spectral traces using a flux calculation according to specific embodiments of the invention. In a typical embodiment, four spectral traces will be extracted. In an alternative embodiment, one or more of the spectral values may be combined (such as 555 and 568 as indicated above) to derive fewer traces. In other cases, one or more additional traces may be derived. Extraction of the four spectral intensity values (or spectral pixel values) from the 14 raw values is accomplished according to specific embodiments of the invention as follows. With individualized spectral templates determined for each dye for each ZMW, trace extraction can be achieved by a number of methods, as described herein. After spectral extraction, the signal intensity at the image location that corresponds to a particular spectral signal from a particular signal source is plotted and/or analyzed as a function of time. Various techniques for spectral extraction from data similar to the spectral-spread image data are known and can be used for spectral extraction according to specific embodiments of the invention. Horne (1986), for example, discusses a number of spectral extraction techniques used in CCD-based astronomical spectroscopy. In one embodiments, spectral extraction is performed for the four intensities using the reference spectra, and spectral-spread image, according to the following equation:

$$F = \frac{\sum_i (R_i - B_i)(P_i/V_i)}{\sum_i P_i^2/V_i}$$

where F is F is the summed flux at each spectral pixel that maximizes S/N. This technique is used for spectral extraction according to specific embodiments of the invention.

As an alternative to a spectral trace determination, methods of the invention may also analyze a single signal derived from the intensity levels at the multiple pixel positions (this may be referred to as a summed spectral signal or a gray-scale spectral signal or an intensity level signal). In many situations, it has been found that spectral extraction, however, provides better SNR and therefore pulse detection when extracted spectral traces are analyzed for pulses separately. In further embodiments, a method according to the invention may analyze the multiple captured pixel data using a statistical model such as a Hidden Markov Model. In present systems, however, determining multiple (e.g., four) spectral traces from the initial signal data has proven a preferred method.

Figure 24:
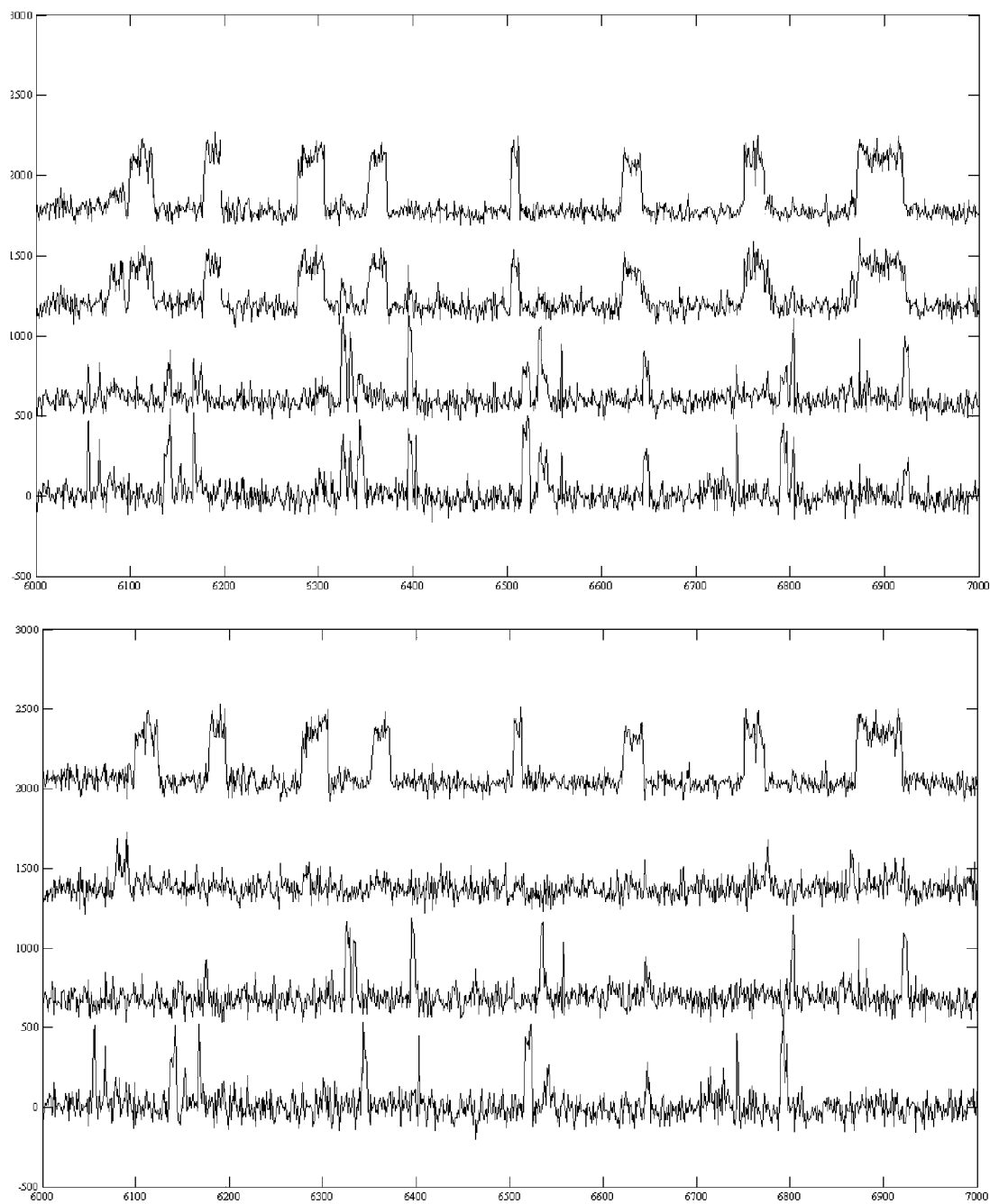
FIG. 24 is a diagram illustrating a set of dye-weighted spectral traces (to) and a set of multi-component spectral traces (bottom) extracted from captured data for a reaction location according to specific embodiments of the invention.
Figure 25:
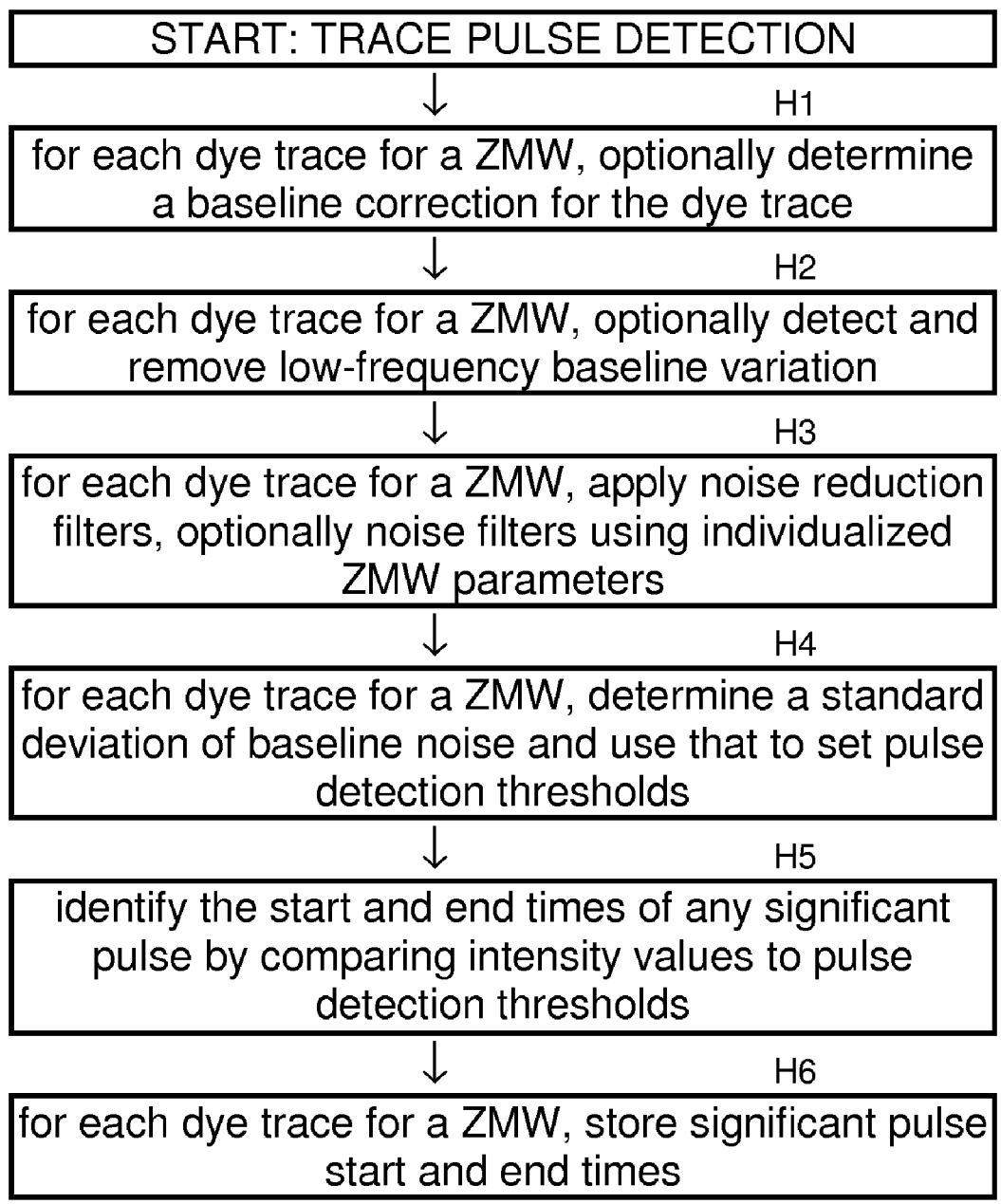
FIG. 25 is a flow chart illustrating an example method of pulse detection in a dye trace according to specific embodiments of the invention.
Figure 26:
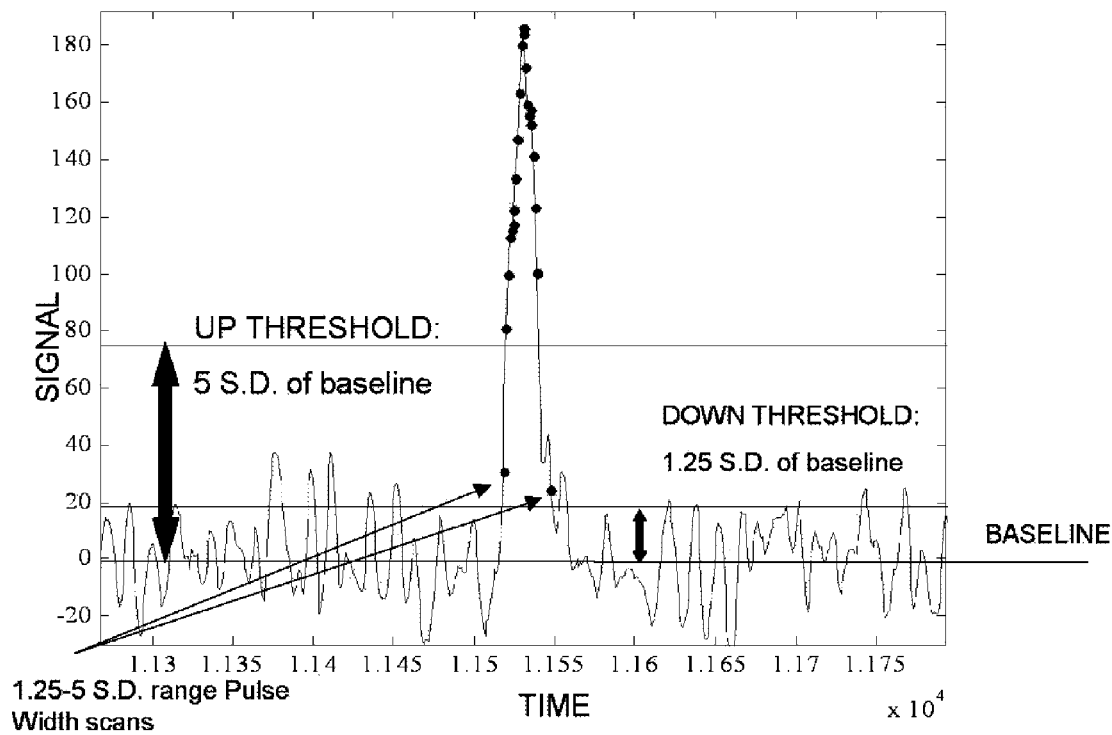
FIG. 26 is a diagram illustrating an example of analysis of one pulse in one spectral trace according to specific embodiments of the invention.

FIG. 24 is a diagram illustrating a set of dye-weighted spectral traces (to) and a set of multi-component spectral traces (bottom) extracted from captured data for a reaction location according to specific embodiments of the invention.
Pulse Recognition FIG. 25 is a flow chart illustrating an example method of pulse detection in a dye trace according to specific embodiments of the invention. FIG. 26 is a diagram illustrating an example of analysis of one pulse in one spectral trace according to specific embodiments of the invention.

Figure 27:
FIG. 27 is a diagram illustrating a number of pulses associated with incorporation events and showing that some pulses with low amplitude are likely to be indicative of actual incorporation events.
Figure 28:
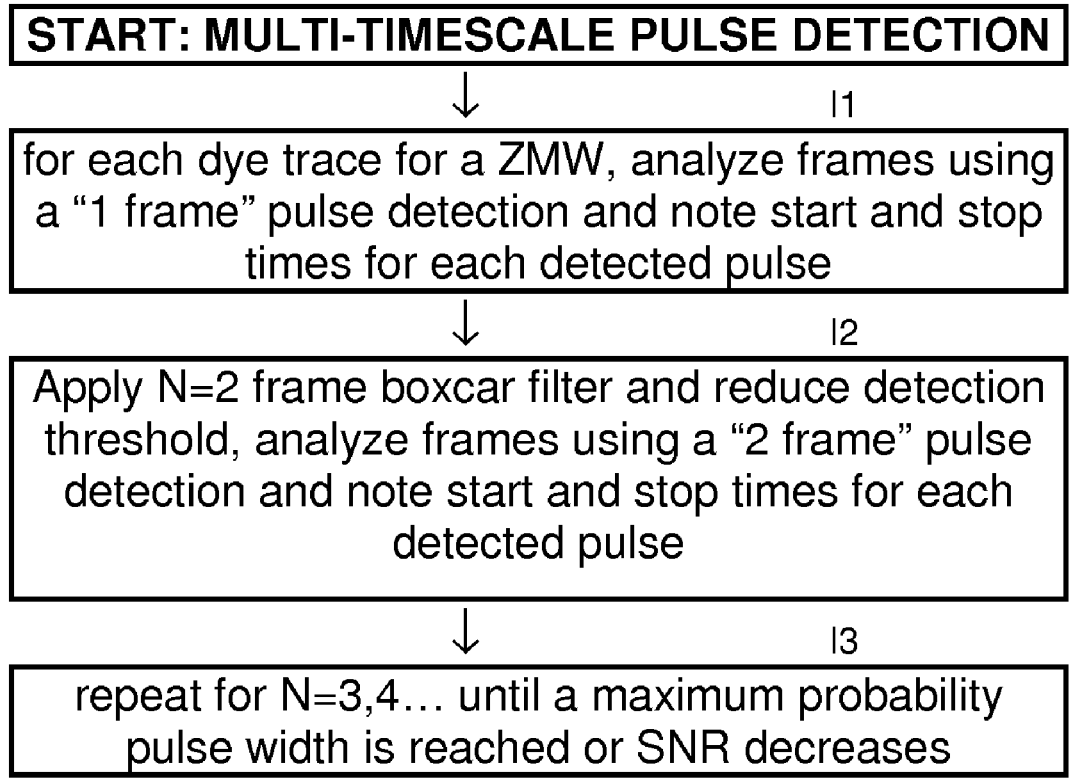
FIG. 28 is a flow chart illustrating an example method of multi-timescale pulse detection according to specific embodiments of the invention.

Further refinements to a pulse detection algorithm from that described above according to specific embodiments of the invention may be made by consideration of variability in captured spectral intensity data that is due solely to the expected kinetic behavior of the underlying sequencing reaction. Such data can, for example, include noiseless traces created by a kinetic model simulator. FIG. 27 is a diagram illustrating a number of pulses associated with incorporation events and showing that some pulses with low amplitude are likely to be indicative of actual incorporation events. The figure illustrates an example of a captured data frames for a number of zero mode waveguides according to specific embodiments of the invention. It has been determined from this analysis that even in the absence of noise or other system variability, the pulse width or duration of an actual incorporation event, as well as the between pulse intervals, stochastically varies. The variation in incorporation event timing affects the both the duration and amplitude of pulses. The duration affect is clearly understood. Amplitude is affected because of the nature of the detectors 116, which provide an intensity value in proportion to the total optical signal energy received during the collection interval. In the discussion herein, this interval is referred to as a frame.

In understanding the data shown in FIG. 27, assume that an incorporation event produces an optical signal intensity at a normalized intensity value of 1 during each capture interval (e.g., frame). Further, assume that a frame is 10 milliseconds. Then, an incorporation event that happens to begin at a frame boundary, and that happens to last for one frame, will produce a pulse with a 10 millisecond (1 frame) width and an amplitude of 1. However, it is equally likely that a 10 millisecond incorporation event will begin in the middle of one frame and complete in the middle of the next frame. In such a case, the same incorporation event will produce a pulse with a 20 millisecond (2 frame) width and an amplitude of 0.5. Furthermore, there may be a relatively high probability that an incorporation event will last only 5 milliseconds (e.g., ½ a frame). If such an incorporation event occurs entirely during a single frame, such an incorporation event will produce a 1 frame pulse (1 frame being the shortest pulse width detectable) with an amplitude of 0.5. There is also a probability that a 5 millisecond pulse will occur exactly across 2 frames. In such a case, the same incorporation event will produce a pulse with a 20 millisecond (2 frame) width and an amplitude of 0.25. With this understanding, it will be understood that the lower amplitude pulses circled in FIG. 27 can have an equal probability of being valid significant pulses as the higher amplitude pulses.

Using the data as described above, a pulse detection algorithm according to specific embodiments of the invention, can assign confidence levels and make adjustments to account for stochastic false positive (FP) rates (e.g., detecting a pulse as a result of noise alone), stochastic false negative (FN) rates (e.g., failing to detect a pulse because it is masked by background noise), and miss-match (MM) errors (e.g., incorrectly classifying the spectra of a pulse due to its detected width and intensity.) Using such an analysis, for example, the invention can determine that optimal pulse calling thresholds are around 3.5 sigma for each channel based on the kinetic parameters of the incorporation reaction and the frame capture parameters.

According to specific embodiments of the invention, such an analysis shows that increasing the frame rate can increase the SNR of sub-frame pulse-width (PW) pulses by roughly sqrt (f.p.s.), and therefore while the FN rate is initially reduced with an increased FPS, it increases again as pulse peak SNR degrades at inverse sqrt (f.p.s.). Detection of one significant pulse as two (referred to as algorithmic branching) also is found to be an increasing problem at higher frame rates.

Figure 29:
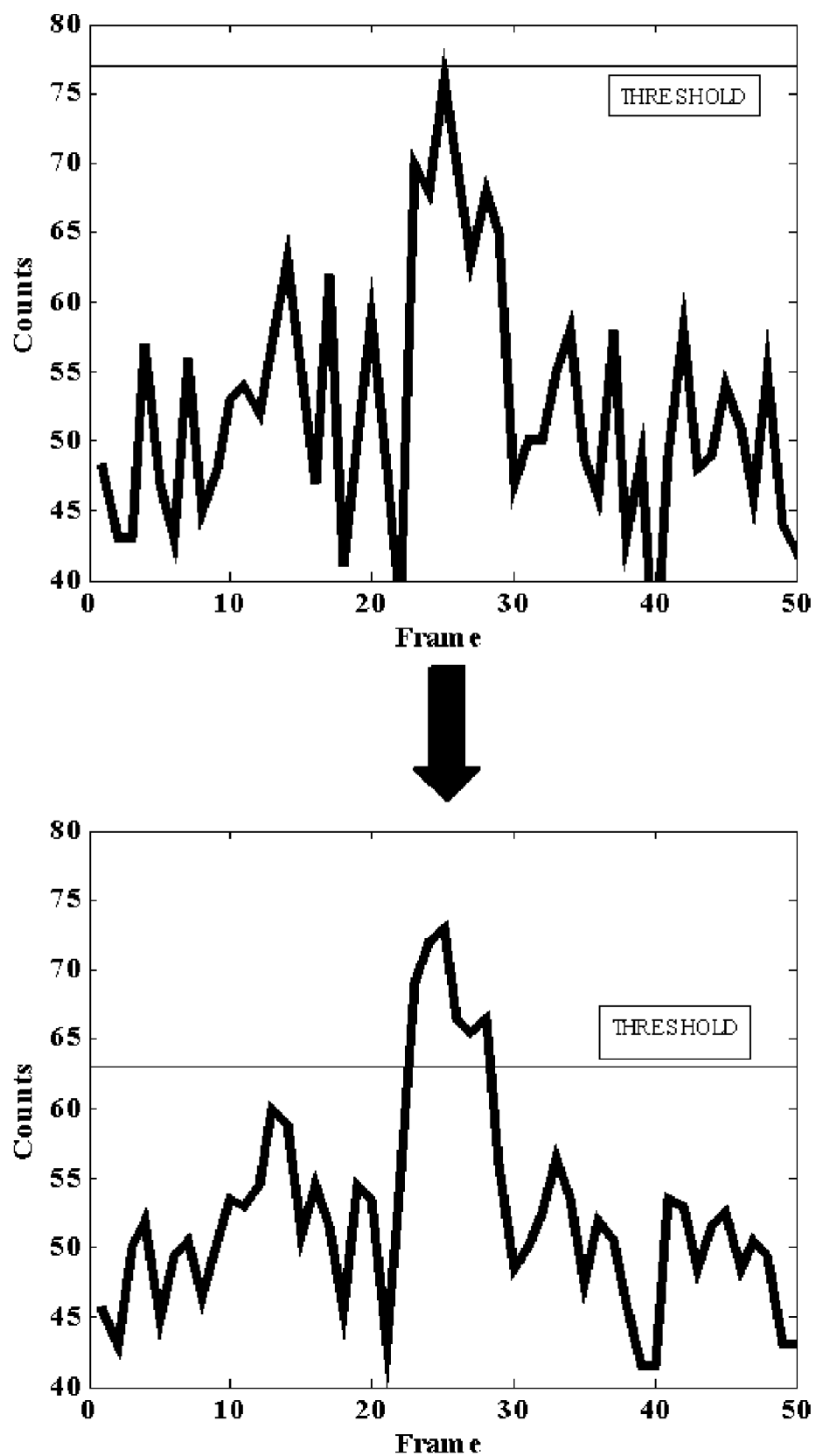
FIG. 29 is a diagram illustrating increasing a time window and reducing a threshold for pulse detection according to specific embodiments of the invention.

According to specific embodiments of the invention, an pulse detection algorithm is optimized to reduce FN rates while allowing an increase in fps rate. Such a pulse detection optimization runs the initial pulse detection algorithm using a standard "1 frame" pulse detector to generate a first pulse list. Then, an N=2 frame boxcar filter is applied, noise reduction is by SQRT(2), the threshold is moved accordingly, and the pulse detector is run to find additional detected pulses. This step can be repeated for N=3, 4 . . . , until N approaches or exceeds the longest expected detectable pulse. FIG. 29 is a diagram illustrating increasing a time window and reducing a threshold for pulse detection according to specific embodiments of the invention. In this example figure, a pulse between frame 23 and 30, with its highest amplitude at just over 75 counts is not detected at N=1 (top) due to a noise threshold set at 77 counts, resulting in a false negative (FN). With N=2, and a subsequent reduction of the noise threshold to about 63, the pulse is detected.

Figure 30:
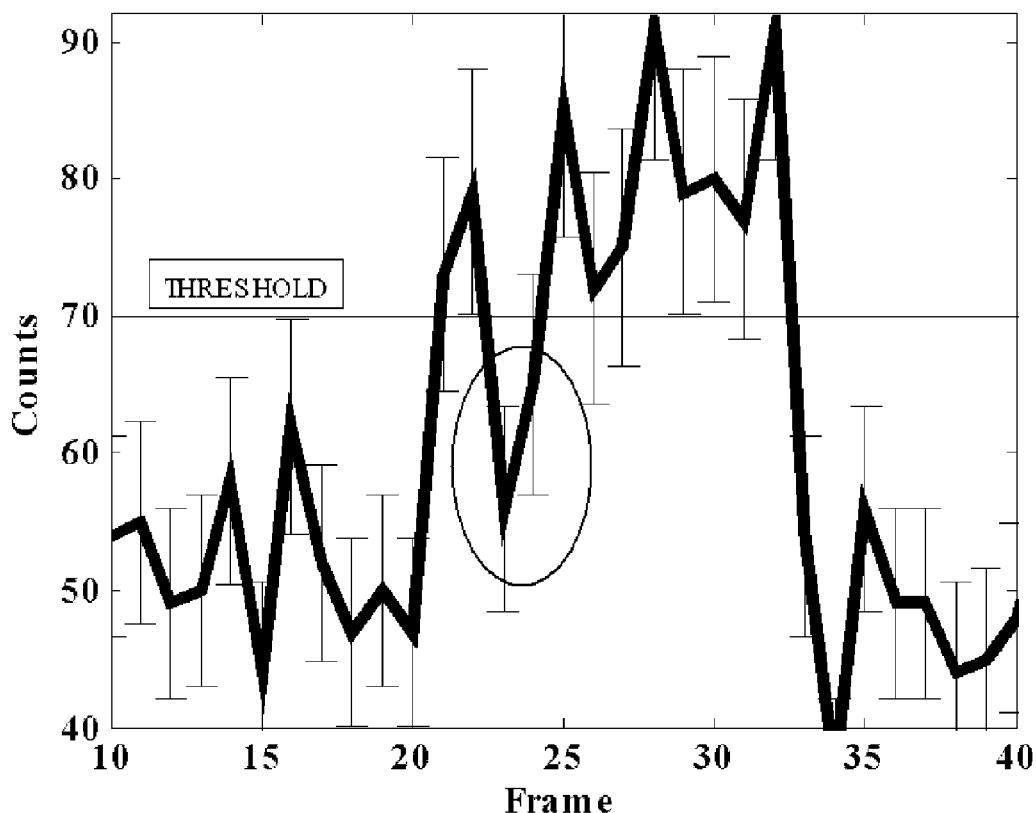
FIG. 30 is a diagram illustrating algorithmic branch detection according to specific embodiments of the invention.
Figure 31:
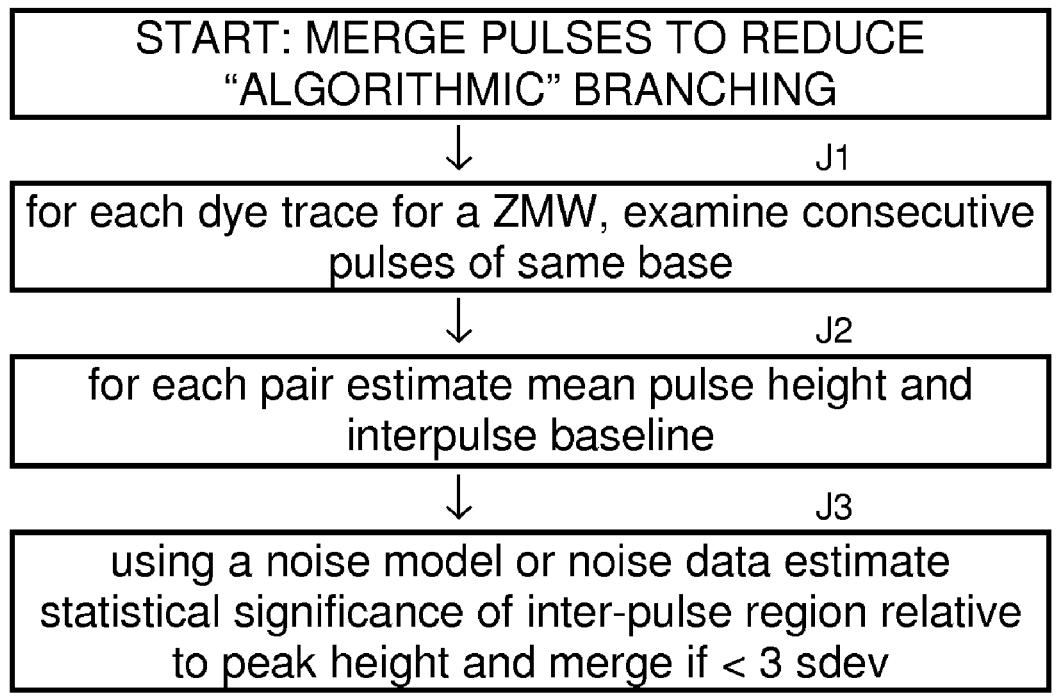
FIG. 31 is a flow chart illustrating an example method of a pulse merging analysis according to specific embodiments of the invention.

In another aspect, it has been determined that lower amplitude pulses are more prone to algorithmic branching near the noise threshold. To address this, a pulse detection according to specific embodiments of the invention uses merge heuristics as follows. For consecutive pulses of same base, for each pair estimate a mean pulse height and interpulse baseline. Using a noise model and/or actual noise data, estimate the statistical significance of inter-pulse region relative to peak height and merge consecutive peaks the statistical significance is <3 standard deviations. FIG. 30 illustrates two consecutive pulses between frames 20 and 34 that would be merged as discussed above according to specific embodiments of the invention, thus eliminating one FP that would occur without the merging. FIG. 31 is a flow chart illustrating an example method of a pulse merging analysis according to specific embodiments of the invention.

Pulse Recognition Using DBR (Diffusional Background Ratio)

As an alternative to pulse recognition using pulse intensity as the primary signal value as described above, according to further specific embodiments, the invention uses the ratio of pulse height to diffusion background, or DBR (diffusional background ratio) in determining significant pulses. While at times this may be referred to a component of SNR (signal to noise ratio), the term DBR is used to avoid confusion with more traditional usages of SNR. In specific embodiments, it has been found that calling pulses by intensity or by sigma can either fail due to laser intensity variations or due to background noise variations (respectively). Calling pulses by the DBR according to specific embodiments of the invention makes the "intensity" component of the pulse less variable even in the presence of laser excitation variations and regardless of background noise envelope fluctuations (due to concentration variations, extremely sticky ZMWs, etc). Furthermore, setting the pulse intensity threshold according to the intensity contributions of freely diffusing fluorophores in the ZMW provides a theoretical framework for locating a single molecule event in a ZMW and provides some immunity from other sources of signal variations and error. There are several methods of obtaining an estimate of the DBR intensity per ZMW.

Thus, in specific embodiments, pulse intensity is described not in absolute counts measured against a threshold, but as a ratio against the background diffusion of fluorophores in and above an individual ZMW.

According to specific embodiments of the invention, for any given pulse, define its DBR as: DBR=(Intensity−dcOffset)/(dcoffset−NDB) where (Intensity−dcOffset) is the average intensity of a pulse above baseline, and "NDB" is the portion of the baseline (dcOffset) that is not diffusion background (e.g., baseline from autofluorescence, base clamping, etc.). In particular embodiments, the NDB is determined from a sample movie of the array (or a neutral substrate, such as a solid aluminum film) with the same laser and camera conditions, which provides values for NDB(ZMW).

The DBR method of pulse calling provides additional information about where in the ZMW a particular pulse originated. This information is used in specific embodiments to determine if multiples polymerase are sequencing in a ZMW, in which case data from that specific ZMW may be excluded from further data analysis. The location of a fluorophore within a ZMW can also be used as one of the parameters in the data analysis as described herein.

The maximum values of the DBR of pulses from a single ZMW also allows estimation of the ZMWs effective diameter according to specific embodiments of the invention. In a particular example implementation, this method was used to estimate the ZMW diameters in an array to vary within 13 nm.

DBR thresholding in some embodiments may be vulnerable to diameter variations of the ZMWs themselves across the array (because more diffusion will occur into larger diameter ZMWs. In specific embodiments, this is accounted for on a per-ZMW basis, for example by transmission light analysis prior to sequencing. With the size of each ZMW known or accurately analyzed, the DBR method is generally preferable to sigma-calling or intensity-calling of pulses.

Trace or Reaction Location Rejection

According to specific embodiments of the invention, as described herein, analysis of individual ZMWs includes repeated evaluation of whether a ZMW should be excluded from further analysis. Because large numbers of reaction locations are being prepared and monitored, it is expected that in some systems some percentage of reaction locations will not provide useful data. This may occur if no reaction enzyme becomes located in a particular ZMW, if more than one reaction enzyme is located in a ZMW or if a reaction enzyme is otherwise producing problematic data. Rejection of particular reaction location data streams may be performed at multiple points during the analysis where the captured data does not match expected data criteria.

Pulse Classification/Confirmation/Base Calling

Figure 32:
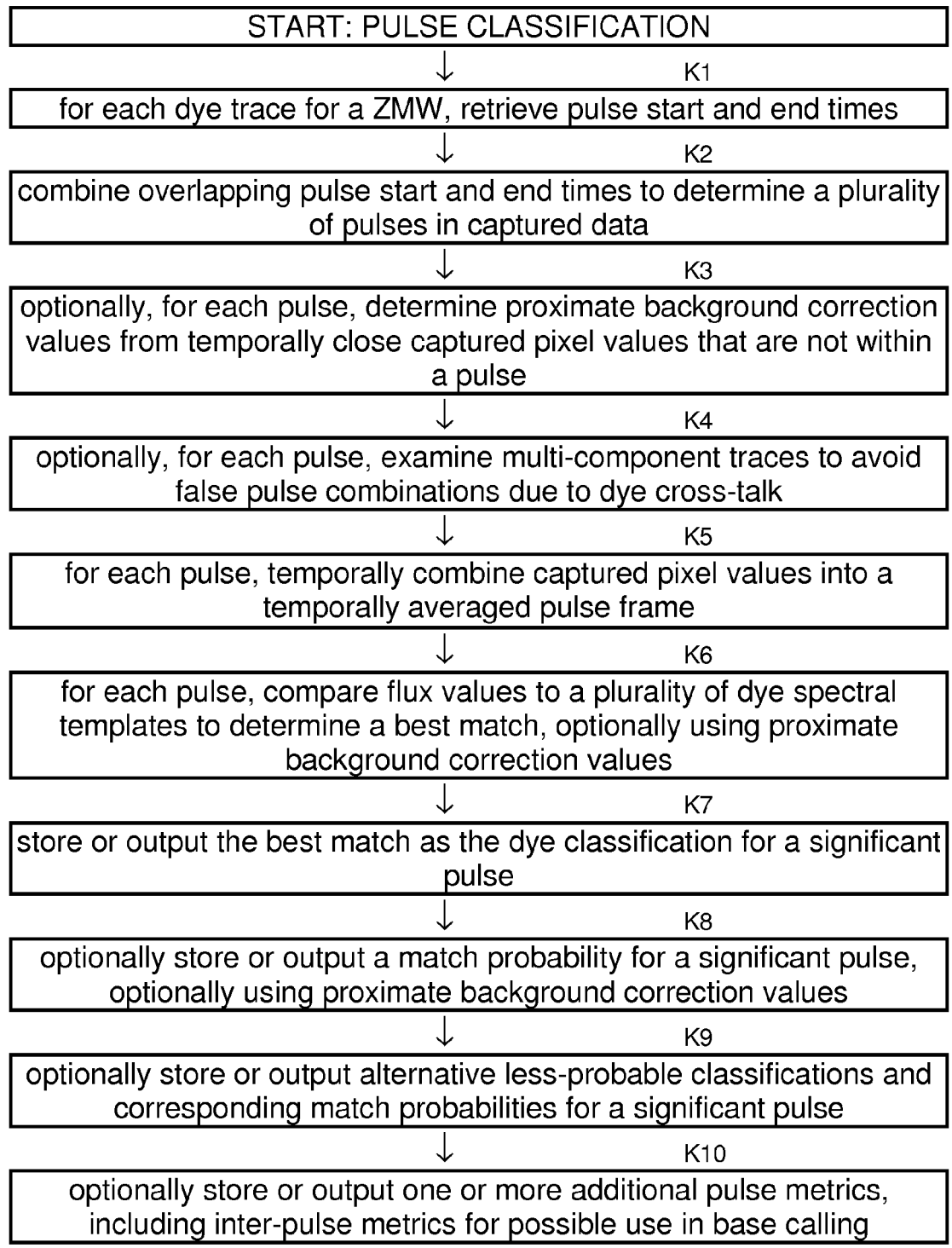
FIG. 32 is a flow chart illustrating an example method of pulse classification according to specific embodiments of the invention.
Figure 33A:
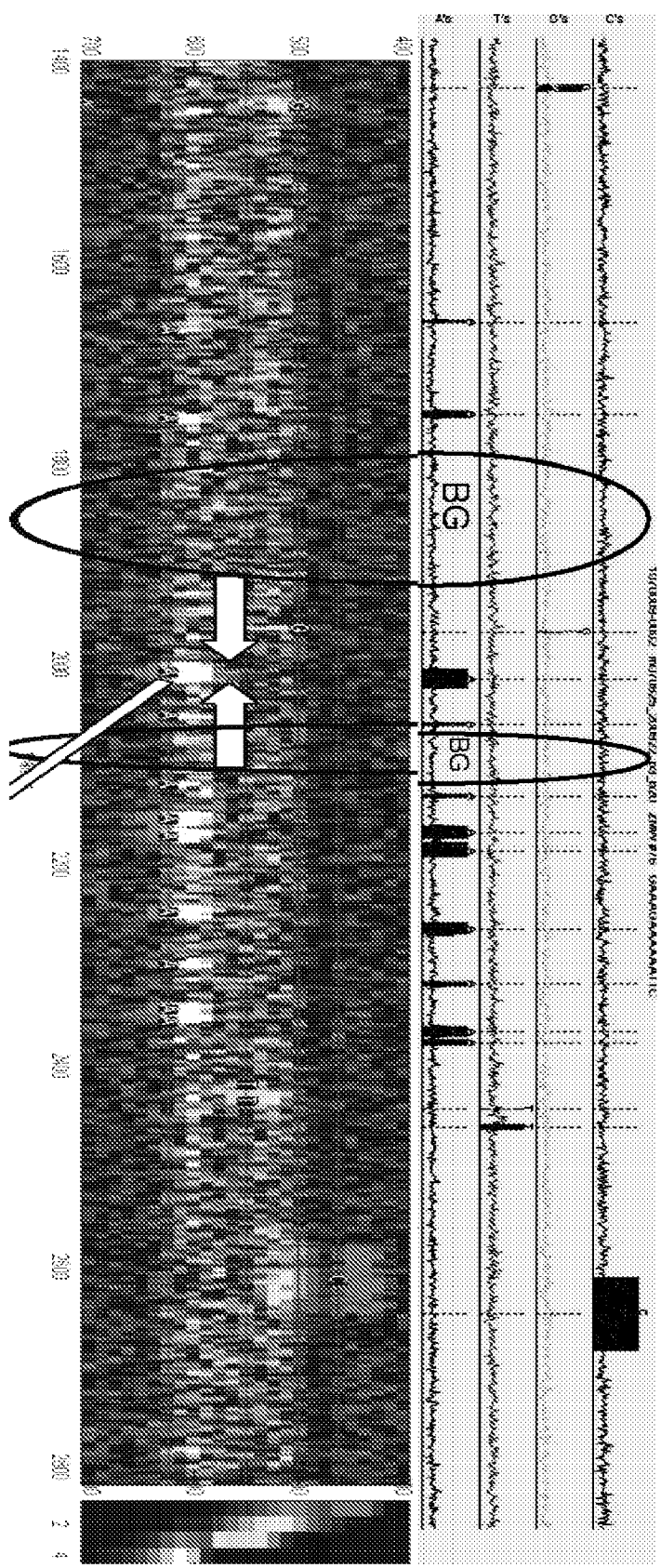
FIG. 33 is a diagram illustrating an example method of pulse classification according to specific embodiments of the invention.
Figure 33B:
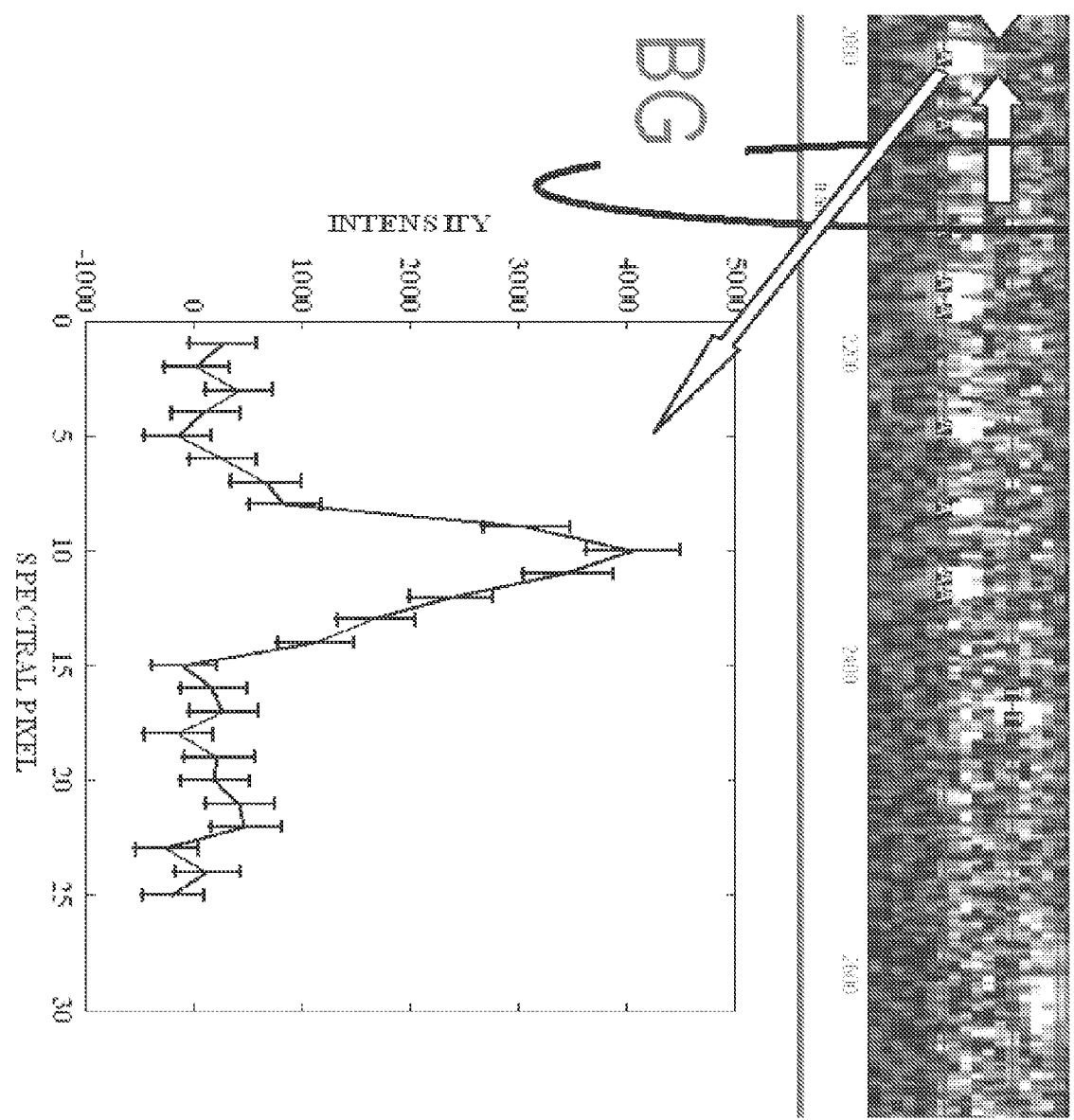
Figure 35:
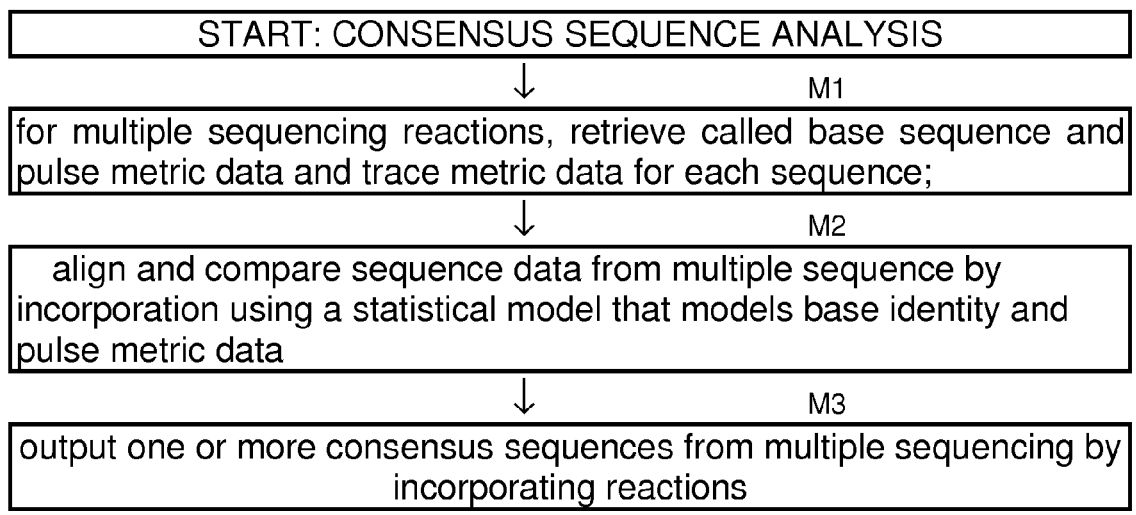
FIG. 35 is a flow chart illustrating an example method of consensus determination according to specific embodiments of the invention.
Figure 36:
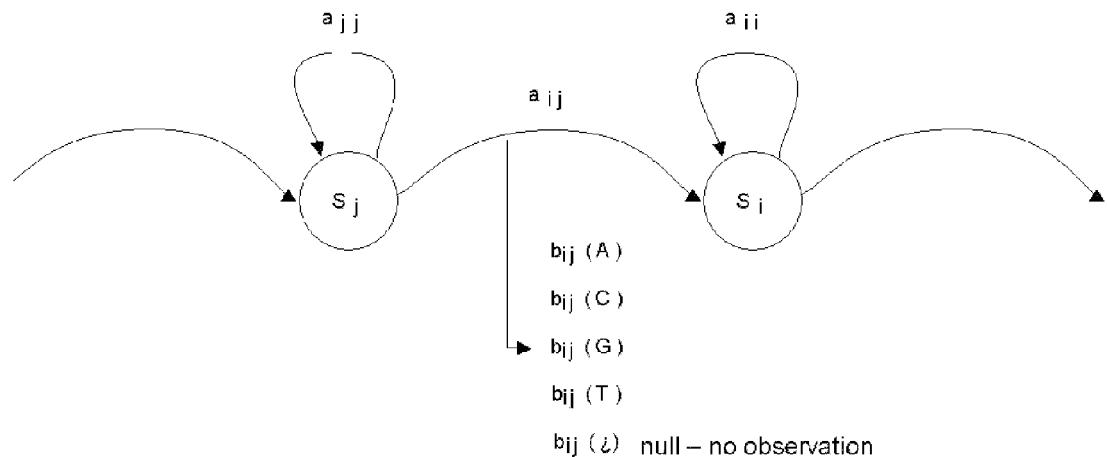
FIG. 36 is a diagram illustrating an example HMM model used in consensus calling according to specific embodiments of the invention.
Figure 37:
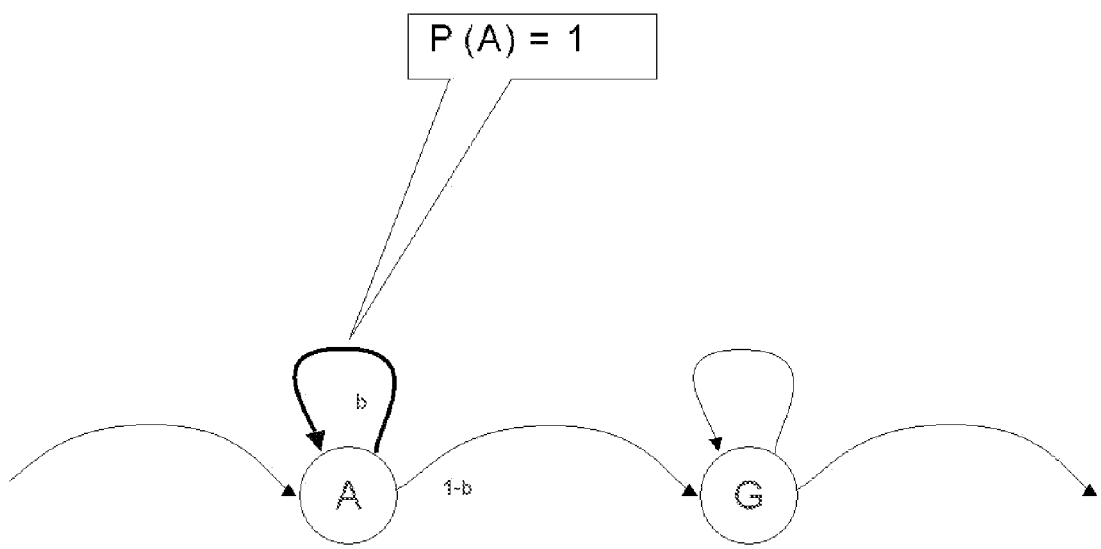
FIG. 37 is a diagram illustrating an example HMM model with a branch prediction probability according to specific embodiments of the invention.
Figure 38:
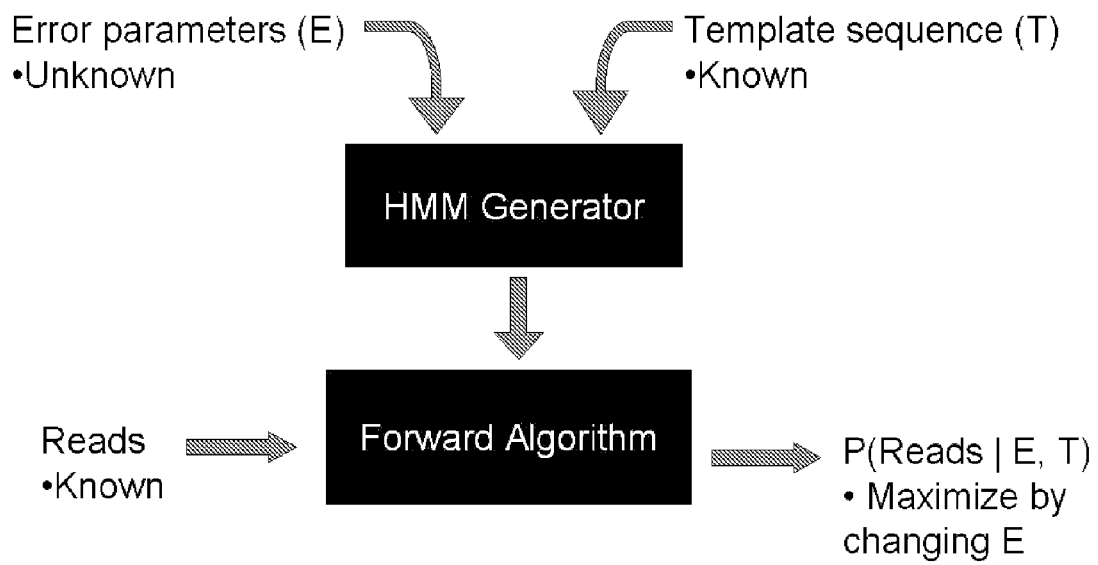
FIG. 38 is a diagram illustrating training an HMM with a set of possibly predictive error parameters and a known read sequence of a known DNA sequence template.
Figure 39:
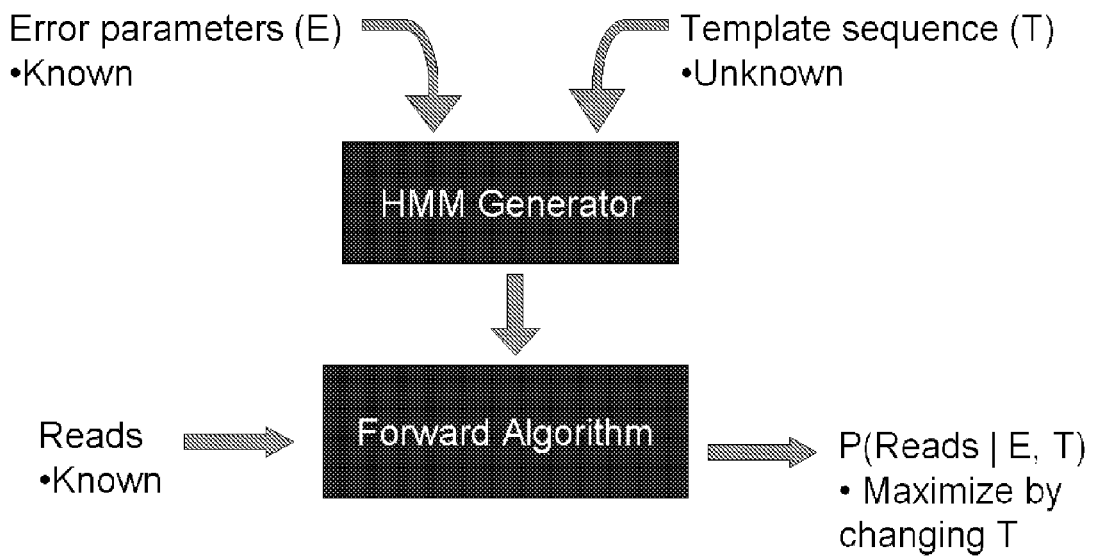
FIG. 39 is a diagram illustrating employing an HMM with a set of predictive error parameters, a known read sequence, and an unknown DNA sequence template.

FIG. 32 is a flow chart illustrating an example method of pulse classification according to specific embodiments of the invention. In this example, for each dye trace for a ZMW, the invention retrieves pulse start and end times (Step K1); these times are combined to determine a plurality of pulses in the pre-extraction captured data (Step K2); optionally, for each pulse, determine proximate background correction values from temporally close captured pixel values that are not within a pulse (Step K3); optionally, for each pulse, examine multi-component traces to avoid false pulse combinations due to dye cross-talk (Step K4); for each pulse, temporally combine captured pixel values into a temporally averaged pulse frame (Step K5); for each pulse, compare flux values to a plurality of dye spectral templates to determine a best match, optionally using proximate background correction values (Step K6); store or output the best match as the dye classification for a significant pulse (Step K7); optionally store or output a match probability for a significant pulse, optionally using proximate background correction values (Step K8); optionally store or output alternative less-probable classifications and corresponding match probabilities for a significant pulse (Step K9); optionally store or output one or more additional pulse metrics, including inter-pulse metrics for possible use in base calling) (Step K10).

A number of comparative methods may be used to generate a comparative metric for this process. For example, in preferred aspects, a test is used to establish the goodness of fit of the comparison. In a particular example, for an extracted pulse spectrum ($S_i$), the amplitude (A) of the fit of an individual dye spectral shape, as measured from the pure dye calibration spectrum, $P_i$, is the only variable to solve and will have a $\chi^2$ value of:

$$\chi^2 = \sum_i \frac{(S_i - AP_i)^2}{V_i}$$

The probability that the pure dye spectrum fits with the extracted spectrum is then derived from the $\chi^2$ probability distribution (with a number of degrees of freedom for the number of data points used, $\nu$). The classification of a given pulse spectrum is then identified based upon calculating values for each of the four different dyes. The lowest $\chi^2$ value (and the highest probability fit), assigns the pulse to that particular dye spectrum, and the pulse is called as corresponding to that dye.

Again, other techniques may be employed in classifying a pulse to a particular spectrum, including for example, measuring correlation coefficients for each of the 4 possible dyes for the spectrum, with the highest correlation providing the indication to which base or dye the pulse will be classified.

In addition to comparison of the pulse spectra to the calibration spectra, a number of other pulse metrics may be employed in classifying a pulse as correlating to a given dye/nucleotide. In particular, in addition to the spectral properties associated with a given dye, signals associated with incorporation of a given dye labeled nucleotide typically have a number of other characteristics that can be used in further confirming a given pulse classification. For example, and as alluded to above, different dye labeled nucleotides may have different characteristics such as pulse arrival time (following a prior pulse), pulse width, signal intensity or integrated counts (also referred to as pulse area), signal to noise ratio, power to noise ratio, pulse to diffusion ratio (ratio of pulse signal to the diffusion background signal in each waveguide), spectral fit (e.g., using a minimum $\chi^2$ test, or the like), spectrum centroid, correlation coefficient against a pulse's classified dye, time interval to end of preceding pulse, time interval to the ensuing pulse, pulse shape, polarization of the pulse, and the like.

In particularly preferred aspects, a plurality of these various pulse metrics are used in addition to the spectral comparison, in classifying a pulse to a given dye, with particularly preferred processes comparing two, three, five, 10 or more different pulse metrics in classifying a pulse to a particular dye/nucleotide.

Optional Additional Trace Extraction to Avoid Conflation

As discussed herein, extraction from spectra to multiple spectral traces is may be performed according to an algorithm that maximizes the flux in each trace. As a result of this and of the fact that selected spectral dyes may have substantial overlap, in certain situations this approach will result in single incorporation pulse being detected in two traces. Because traces are used generally to determine start and end times from the captured data, this situation does not present a problem in most cases.

However, in some cases this may cause a merging of pulses that should be associated with two differently classified incorporation events. To address, in specific embodiments of the invention, a secondary spectral trace extraction is performed that attempts to increase separation between spectral template matches. This secondary trace extraction is then used to confirm that start and end times of pulses represent a pulse in one spectral color and not in two overlapping colors.

Consensus Generation and Sequence Alignment Using Statistical Models and Pulse Features Background Various techniques for automated "smart" base calling of Electrophoretic DNA sequencing data have been discussed. Electrophoretic DNA sequencing often involves trace data from four different dyes that are used to label four bases. PHRED is a base-calling program for automated sequencer traces that outputs at each base generally one of five base identifiers (A C T G and N for not identifiable) and often a quality score for each base. In PHRED processing of DNA traces, predicted peak locations in terms of migration times are determined, observed peaks are identified in the trace and are matched to predicted peak locations, sometimes omitting some peaks and splitting. Unmatched observed peaks may be checked for any peak that appears to represent a base but could not be assigned to a predicted peak in the third phase and if found, the corresponding base is inserted into the read sequence. Peaks in a PHRED analysis may be difficult to distinguish in regions where the peaks are not well resolved, noisy, or displaced (as in compressions). The PHRED algorithm typically assigns quality values to the bases, and writes the base calls and quality values to output files. PHRED can evaluate the trace surrounding each called base using four or five quality value parameters to quantify the trace quality. PHRED can use dye chemistry parameter data to do such tasks as identifying loop/stem sequence motifs that tend to result in CC and GG merged peak compressions. PHRAP is a sequence assembly program often used together with PHRED. PHRAP uses PHRED quality scores to determine highly accurate consensus sequences and to estimate the quality of the consensus sequences. PHRAP also uses PHRED quality scores to estimate whether discrepancies between two overlapping sequences are more likely to arise from random errors, or from different copies of a repeated sequence. Various expert analysis and similar systems have been proposed for analyzing such data, See, for example, U.S. Pat. No. 6,236,944, Expert system for analysis of DNA sequencing electropherograms. The use of statistical models, such as hidden Markov models (HMMs), for DNA sequencing has be discussed by several authors (See, e.g., Petros Boufounos, Sameh El-Difrawy, Dan Ehrlich, HIDDEN MARKOV MODELS FOR DNA SEQUENCING, Journal of the Franklin Institute, Volume 341, Issues 1-2, January-March 2004, Pages 23-36 Genomics, Signal Processing, and Statistics. HMMs have been discussed as an approach to DNA basecalling, using techniques such as modeling state emission densities using Artificial Neural Networks, and a modified Baum-Welch re-estimation procedure to perform training. Consensus sequences have been proposed to label training data to minimizing the need for hand-labeling.

In further specific embodiments, software methods of the present invention include techniques for generating consensus DNA sequence information of high accuracy from a collection of less accurate reads generated by a real-time sequencing by incorporation system. In specific embodiments, two features of data typical of some such systems that motivate these techniques are: (1) the errors in the raw data are mostly insertions or deletions of base symbols from the correct sequence, rather than 'mismatches' or misidentified bases; (2) a relatively large number (e.g., 1000 or more) of data points are collected in real time for each base symbol in the raw read.

As described above, a signal intensity and signal spectrum is measured through time. This results in a large collection of data features associated with each base in the raw read sequence. The time series data are summarized by finding regions of high signal intensity 'pulses', and measuring a series of features of those pulses, such as their duration, average intensity, average spectrum, time until the following pulse, and best reference spectra match. Observable pulses are generated when nucleotides are productively incorporated by the polymerase ("incorporation pulses"), as well as by interfering processes (such as incorrect bases that stick temporarily but are not incorporated or correct bases that become illuminated temporarily, but are not fully incorporated, and then are incorporated and produce a second pulse (branching)) that introduce errors into the observed sequence. (Pulses that are entirely due to random noise may also be detected and are attempted to be identified as described above). The statistical nature of the process that generates the pulses results in wide, but measurable distributions of pulse features. Processes that generate spurious pulses generate pulses with different distributions of pulse features, although the distributions between spurious pulses and incorporation pulses will overlap.

Thus, in specific embodiments, a predictive HMM observation distribution model, is extended to not only identity of the called base, but also the features of the associated pulse. In this method each class of microscopic event (true incorporations as well as interfering events) generates pulses with different but overlapping probability distributions in the space of pulse features. The distribution over pulse feature space for each pulse type is learned from experimental data and used to generate an approximate observation distribution via density estimation techniques. In a final sequence alignment step, a most likely template (sequence) is discovered by constructing a series of trial models that maximize the likelihood of the observed data under the model, via an expectation maximization procedure.

The following example describes this algorithmically. Let $b_{ij}(O)$ represent the probability distribution of observations received when transitioning from state i to state j of the HMM. In typical alignment applications, the alphabet of observations that it is possible to observe is limited to {A,G,C,T}. That is, each pulse observed is summarized only by its base identity. When combining multiple reads of the same DNA into a single consensus read, it is necessary to resolve the ambiguity that exists between reads. For example, in a base detection from two sources as follows:

AGCG
AGCG

A probability model according to specific embodiments of the invention must decide among a number of competing hypotheses about the true template. For example, in attempting to decide between a T and an A at the highlighted position the model asks which event is more likely, that a T base generates an emission that is called as an A, or that an A base is called as a T. While a standard alignment approach of choosing the template that maximizes the likelihood still applies, in the present invention the $b_{ij}(O)$ that models the probability of an observation is a function not solely of the base identity, but is also extended to return a measure of the probability of observing a pulse and various of its associated features on that transition. In this example, if the T pulse has stored or associated with it observed features indicating it was a higher intensity, longer pulse (and therefore less likely to be misclassified), while the A pulse was weaker and briefer, these features would be included in the probability model with other alignment probabilities to determine whether T or A was more probable. Other features being equal, the probability of having misclassified the bright T pulse being generated from an A template location would be much smaller than the probability of the weak brief A pulse being generated from a T base, therefore the model would call T as the consensus in that position. Because the data analyzed during the consensus alignment phase includes a number of different physical parameters of identified pulses and overall reaction parameters, rather than just a single quality score, many different characteristics of a real-time incorporation sequencing reaction can be used in the predictive model. The predictive model can thus be trained to account for the probability that a detected pulse was due to a branch or a stick of a labeled nucleotide analog, probabilities of which will vary for different bases, as well as account for overall reaction quality features such as overall noise detected at a reaction location or overall confidence of spectral classifications at a reaction location.

In a particular example embodiment, each state of an example HMM models a location along the template DNA strand where the synthesizing polymerase will reside between incorporation events. Two classes of transitions that can occur from this state are (1) a "move" transition where the polymerase incorporates a base and proceeds one position along the template, with a probability denoted by $a_{i,i+1}$ and (2) a "stay" transition where the polymerase binds a nucleotide, but unbinds before the incorporation event (a "branch") or a labeled nucleotide "sticks" transiently to the surface of the ZMW, inside the illumination region, and the polymerase does not move along the template, with probability given by $a_{i,i}$. A branch generally emits the symbol corresponding to the current template location while a stick generates a random symbol. The probability of branching and sticking are modeled as a function of the observation symbols (A C T G and null), and optionally modeled as a function of symbols for pulse metrics, such as intensity, duration, forward interval, subsequent interval, etc.

There are a variety of potential methods for generating the $b_{ij}(O)$ probability distribution for a multi-dimensional space of pulse parameters. Given the various pulse parameters and reaction parameters that may be calculated and stored as described herein, one presently preferred approach is to learn the distribution from empirical data acquired from known templates. By aligning the acquired pulse stream to the known template, pulses from a variety of classes can be used to generate empirical parameter distributions.

One method of scoring such a model during training is determining parameters that result in a maximum alignment length as is understood in the art.

Embodiment in a Programmed Information Appliance

Figure 40:
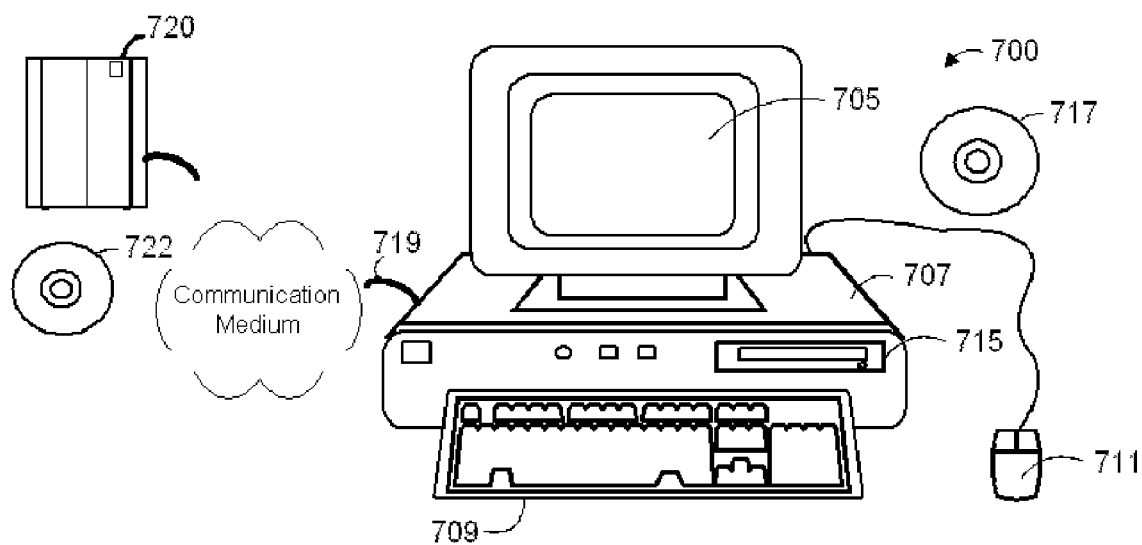
FIG. 40 is a block diagram showing a representative example logic device in which various aspects of the present invention may be embodied.

FIG. 40 is a block diagram showing a representative example logic device in which various aspects of the present invention may be embodied. As will be understood to practitioners in the art from the teachings provided herein, the invention can be implemented in hardware and/or software. In some embodiments of the invention, different aspects of the invention can be implemented in either client-side logic or server-side logic. As will be understood in the art, the invention or components thereof may be embodied in a fixed media program component containing logic instructions and/or data that when loaded into an appropriately configured computing device cause that device to perform according to the invention. As will be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

FIG. 40 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional monitor 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

The invention also may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

OTHER EMBODIMENTS

The invention has now been described with reference to specific embodiments. Other embodiments will be apparent to those of skill in the art. In particular, a viewer digital information appliance has generally been illustrated as a personal computer. However, the digital computing device is meant to be any information appliance for interacting with a remote data application, and could include such devices as a digitally enabled television, cell phone, personal digital assistant, etc.

Although the present invention has been described in terms of various specific embodiments, it is not intended that the invention be limited to these embodiments. Modification within the spirit of the invention will be apparent to those skilled in the art. In addition, various different actions can be used to effect a request for sequence data.

It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this application, including any references filed as part of an Information Disclosure Statement, are incorporated by reference in their entirety.

What is claimed is:

1. A method of identifying a nucleotide in a nucleic acid sequence, comprising:
   receiving a first optical signal from a reaction that produces optical signals during a template dependent primer extension reaction, wherein
      the first optical signal is emitted from a detectable label on a polyphosphate chain of a nucleotide analog,
      the detectable label is liberated from the nucleotide analog during an incorporation of the nucleotide analog in the template dependent primer extension reaction, and
      an optical pulse width of the first optical signal correlates with an amount of time the nucleotide analog is associated with a polymerase prior to liberation of the detectable label;
   classifying the first optical signal as a significant pulse based upon at least one of the optical pulse width of the first optical signal and an intensity of the first optical signal;
   associating the first optical signal with a spectrally distinguishable signal profile that correlates to a particular dye spectrum;
   when the first optical signal is (i) deemed a significant pulse by the classifying and (ii) is associated with a spectrally distinguishable signal profile by the associating, determining whether the first optical signal is an incorporation event based upon a signal environment around the first optical signal, wherein the signal environment includes a characterization of an optical signal preceding the first optical signal or a characterization of an optical signal that comes after the first optical signal; and
   identifying the nucleotide in the nucleic acid sequence when the first optical signal is determined to be an incorporation event,
   wherein the receiving, classifying, associating, determining, or identifying is performed using a suitably programmed computer.

2. The method of claim 1, wherein the step of classifying the first optical signal as a significant pulse comprises correlating the first optical signal with a plurality of pulse metrics indicative of a significant pulse, wherein the plurality of pulse metrics comprises at least one of the optical pulse width of the first optical signal and the intensity of the first optical signal.

3. The method of claim 2, wherein at least one of the plurality of pulse metrics indicative of a significant pulse is selected from the group consisting of, pulse area, signal to noise ratio, pulse to diffusion background ratio, spectral correlation coefficient to identified dye, spectrum centroid, pulse spacing, pulse shape, and pulse polarization.

4. The method of claim 2, wherein at least one of the plurality of pulse metrics indicative of a significant pulse is pulse shape.

5. The method of claim 2, wherein the step of classifying the optical first signal as a significant pulse comprises determining that the first optical signal exceeds one or more of a signal intensity threshold and a signal duration threshold.

6. The method of claim 1, wherein the step of classifying the first optical signal as a significant pulse comprises determining that the first optical signal exceeds both a signal intensity threshold and a signal duration threshold.

7. The method of claim 1, wherein
the step of receiving the first optical signal comprises translating a received first optical signal into optical signal data, and wherein the optical signal data comprises a first component indicative of an intensity of the first optical signal, and a second component indicative of a location in a detection system at which the first optical signal was received.

8. The method of claim 7, wherein
the step of receiving the first optical signal comprises imaging the first optical signal on pixels of the detecting system,
the first component of the optical signal data comprises signal intensity data from a first plurality of pixels, and
the second component of the optical signal data comprises a position of the plurality of pixels in the detection system.

9. The method of claim 7, wherein the step of associating the first optical signal with the spectrally distinguishable signal profile comprises comparing the second component of the optical signal data to a standard signal data component indicative of a location in the detection system at which a standard optical signal from a standard fluorescent label associated with the spectrally distinguishable signal profile was received.

10. The method of claim 7, further comprising the step of providing a set of first and second standard signal data components for each of a plurality of different standard fluorescent labels or fluorescently labeled nucleotides, wherein the step of associating the first optical signal with the spectrally distinguishable signal profile comprises comparing at least one of the first and second components of the optical signal data to the set of first and second standard signal data components.

11. A method for calling bases in a nucleic acid sequencing process, comprising:
receiving a first optical signal detected from a reaction that produces optical signals during a reaction of a nucleotide analog with a polymerase/template/primer sequence complex wherein
the first optical signal is emitted from a detectable label on a polyphosphate chain of the nucleotide analog,
the detectable label is liberated from the nucleotide analog during the incorporation of the nucleotide analog in the reaction with the polymerase/template/primer sequence complex, and
an optical pulse width of the first optical signal correlates with an amount of time the nucleotide analog is associated with a polymerase of the polymerase/template/primer sequence complex prior to liberation of the detectable label;
classifying the first optical signal as a significant pulse based upon at least one of the optical pulse width of the first optical signal and an intensity of the first optical signal;
associating the first optical signal with a spectrally distinguishable signal profile that correlates to a particular dye spectrum;
when the first optical signal is (i) deemed a significant pulse by the classifying and (ii) is associated with a spectrally distinguishable signal profile by the associating, identifying the optical signal data as corresponding to an incorporation event based upon the signal environment around the first optical signal, wherein the signal environment includes a characterization of an optical signal preceding the first optical signal or a characterization of an optical signal that comes after the first optical signal;
calling the base in a template sequence when the first optical signal is determined to be an incorporation event,
wherein the receiving, classifying, associating, identifying or calling is performed using a suitably programmed computer.

12. The method of claim 11, further comprising repeating the receiving, classifying, associating, identifying, and calling steps to call a plurality of contiguous bases in the template sequence.

13. A method of identifying a base in a target nucleic acid sequence, comprising:
receiving a first optical signal pulse from a reaction that produces optical signal pulses during a template dependent primer extension reaction wherein
the first optical signal is emitted from a detectable label on a polyphosphate chain of a nucleotide analog,
the detectable label is liberated from the nucleotide analog during an incorporation of the nucleotide analog in the template dependent primer extension reaction, and
an optical pulse width of the first optical signal correlates with an amount of time the nucleotide analog is associated with a polymerase prior to liberation of the detectable label;
applying the first optical signal pulse to a predicting function, wherein the predicting function was trained using a plurality of pulse metrics derived from signal pulses associated with incorporation of one or more different nucleotide analogs in template dependent primer extension reactions, wherein the identity of the one or more different nucleotides for the plurality of pulse metrics is known and wherein the plurality of pulse metrics includes optical pulse width; and
identifying the first pulse as a pulse associated with incorporation of a specific nucleotide analog when the predicting function indicates that a probability that the first pulse is associated with incorporation of the specific nucleotide exceeds a threshold probability,
wherein the receiving, applying, or identifying is performed on a suitably programmed computer.

14. The method of claim 13, wherein the plurality of pulse metrics comprises at least two different pulse metrics.

15. The method of claim 13, wherein the plurality of pulse metrics comprises at least 5 different pulse metrics.

16. The method of claim 13, wherein the plurality of pulse metrics comprises at least 10 different pulse metrics.

17. A method of identifying a nucleotide in a nucleic acid sequence comprising:
at an optical detector pixel array, capturing a plurality of optical signals from a plurality of locations of a plurality of template dependent primer extension sequencing reactions that produce optical signals;
transmitting the captured plurality of optical signals to a computer system;
identifying pixel areas of said optical detector pixel array that correspond to one or more individual reaction locations;
determining one or more calibration parameters applicable to the one or more reaction locations;
establishing one or more individualized calibration parameters for the one or more individual reaction locations;
for each respective reaction location in the one or more reaction locations, analyzing a subset of the optical signals in the plurality of optical signals captured by corresponding pixels of said optical detector pixel array to identify a series of significant pulses, wherein an optical pulse width of each optical signal in the plurality of optical signals correlates with an amount of time a corresponding nucleotide analog is associated with a polymerase prior to liberation of a detectable label associated with the corresponding nucleotide analog in a template dependent primer extension sequencing reaction in the plurality of template dependent primer extension sequencing reactions, and an optical signal in the subset of optical signals is deemed a significant pulse based upon at least one of the optical pulse width of the corresponding optical signal in the subset of optical signals and an intensity of the corresponding optical signal in the subset of optical signals;

for the series of significant pulses corresponding to a respective reaction location in the one or more reaction locations, classifying each respective pulse in said series of pulses as associated with a type of nucleotide based upon a spectrally distinguishable signal profile of the respective pulse;

for individual reaction locations, calling bases in the nucleic acid sequence from the identification of the nucleotide associated with an optical signal that is also an incorporation signal; and forming one or more consensus sequences of bases by analyzing called bases and identified pulses from a plurality of locations;

wherein the computer system is suitably programmed to perform the identifying, determining, establishing, analyzing, classifying, calling, or forming.

18. The method of claim 17, wherein the step of capturing the plurality of optical signals comprises translating a received optical signal into optical signal data, and wherein the optical signal data comprises a first component indicative of an intensity of the received optical signal, and a second component indicative of a location in a detection system at which the received optical signal was received.

19. The method of claim 17, wherein the step of capturing the plurality of optical signals comprises capturing a sequence of digital image frames, wherein each frame comprises a plurality of pixel intensity and position values for multiple reaction locations.

20. The method of claim 17, wherein the step of forming one or more calibration parameters applicable to a plurality of reaction locations comprises one or more of:

determining an alignment by comparing a line through central image areas of a plurality of reaction locations to the alignment of pixels of the optical detector pixel array;

determining one or more high resolution spectral templates by averaging spectral calibration data detected at a plurality of pixel areas of the optical detector pixel array;

determining one or more high resolution spectral templates by averaging spectral calibration data detected at a plurality of pixel areas during a sub-pixel tilt between said optical detector pixel array and said reaction locations;

determining one or more noise parameters; and determining one or more drift parameters.

21. The method of claim 17, wherein the step of establishing one or more individualized calibration parameters for the one or more individual reaction locations comprises one or more of:

determining individualized reference centroids for the one or more individual reaction locations;

determining individualized sub-pixel reference centroids for the one or more individual reaction locations;

determining individualized spectral templates for the one or more individual reaction locations;

determining individualized background levels for the one or more individual reaction locations; and determining individualized noise characteristics for the one or more individual reaction locations.

22. The method of claim 17, wherein the step of, for each respective reaction location in the one or more reaction locations, analyzing a subset of the optical signals in the plurality of optical signals captured by corresponding pixels of said optical detector pixel array to identify a series of significant pulses comprises one or more of:

using individualized spectral templates for respective reaction locations, extracting one or more spectral traces;

identifying significant pulses in said one or more spectral traces by analyzing at least two metrics of said traces;

determining start and stop times for pulses from said one or more spectral traces;

combining start and stop times for one or more spectral trace to identify significant pulses of captured optical signals;

using as two of said at least two metrics, trace amplitude above a base line and duration of amplitudes above a base line;

using as two of said at least two metrics, a signal-to-noise measure of trace above a threshold and duration of measure above a threshold;

using as two of said at least two metrics, a signal to diffusion background ratio measure of trace above a threshold and duration of measure above a threshold; and combining start and stop times for one or more spectral trace to identify background intervals of captured optical signals.

23. The method of claim 22, further comprising additional pulse recognition steps comprising one or more of:

determining a second set of spectral traces to detect spectrally merged pulses;

adjusting a base-line threshold and a duration threshold to detect lower amplitude longer duration pulses; and analyzing adjacent pulses to merge algorithmically branched pulses.

24. The method of claim 17, wherein the step of classifying each respective pulse in said series of pulses as associated with a type of nucleotide based upon a spectrally distinguishable signal profile of the respective pulse further comprises:

temporally averaging pixels of an optical signal pulse to produce a static spectrally spread image of said respective pulse;

comparing said static spectrally spread image to a plurality of spectral calibration templates; and determining a best fit of said static spectrally spread image to said plurality of spectral calibration templates and classifying said respective pulse as the best-fit calibration template.

25. The method of claim 24, wherein a spectral calibration template in said plurality of spectral calibration templates is an individualized spectral calibration template for a particular location.

26. The method of claim 25, wherein said individualized spectral calibration template for a particular location is the same template used to extract a trace for pulse identification.

27. The method of claim 17, wherein the step of capturing a plurality of optical signals further comprises:

capturing a time series of static digital image frames of multiple reaction locations during incorporation reactions, said frames each comprising a first component indicative of an intensity of the optical signal, and a second component indicative of a location in a detection system at which the optical signal was received.

28. The method of claim 17, wherein the step of identifying pixel areas of said optical detector pixel array that correspond to one or more individual reaction locations comprises:
for individual reaction locations, determining a spectral axis of a set of pixel locations corresponding to an individual reaction location, said spectral axis parallel to a spectral refraction of optical signals produced in response to incorporation of a nucleotide analog; and
determining a spatial axis of said set, said spatial axis orthogonal to said spectral axis.

29. The method of claim 28, further comprising:
for individual reaction locations, combining pixels in said spatial axis direction to produce a spectral images of said reaction locations, said spectral images comprising a plurality of pixels parallel to said spectral axis and a reduce number of one or more pixels parallel to said spatial axis.

30. The method of claim 29 wherein said combining further comprises:
at said optical detector, storing parameters indicating pixel locations of said optical detector array that correspond to one or more individual reaction locations;
at said optical detector, storing parameters indicating how pixels should be combined; and
combining pixels prior to said transmitting.

31. The method of claim 29 wherein said combining further comprises:
at said computer system, combining pixels in said spatial direction using weighted values to maximize detected flux.

32. The method of claim 22, wherein said extracting one or more spectral traces comprises at each frame of said one or more spectral traces, analyzing said plurality of pixel levels to determine one or more spectral intensity levels.

33. The method of claim 32, wherein said one or more spectral intensity levels comprises one to four spectral intensity levels.

34. The method of claim 17, wherein said calling bases comprises identifying incorporation events from one or more of said series of significant pulses of said plurality of optical signals.

35. The method of claim 34, wherein the step of identifying incorporation events from one or more of said series of significant pulses comprises correlating the plurality of optical signals with a plurality of pulse metrics indicative of incorporation events.

36. The method of claim 35, wherein at least one of the plurality of pulse metrics is selected from the group consisting of pulse width, pulse intensity, pulse area, signal to noise ratio, pulse to diffusion background ratio, spectral correlation coefficient to identified dye, spectrum centroid, pulse spacing, pulse shape, and pulse polarization.

37. The method of claim 35, wherein at least one of the plurality of pulse metrics is selected from the group consisting of pulse width, pulse height and pulse shape.

38. The method of claim 34, wherein the step of identifying incorporation events from one or more of said series of significant pulses of said plurality of optical signals comprises identifying the optical signal that exceeds one or more of a signal intensity threshold and a signal duration threshold.

39. The method of claim 34, wherein the step of identifying incorporation events from one or more of said series of significant pulses of said plurality of optical signals comprises identifying the optical signal that exceeds both of a signal intensity threshold and a signal duration threshold.

40. The method of claim 35, wherein the plurality of pulse metrics comprises at least two different pulse metrics.

41. The method of claim 35, wherein the plurality of pulse metrics comprises at least 5 different pulse metrics.

42. The method of claim 35, wherein the plurality of pulse metrics comprises at least 10 different pulse metrics.

43. The method of claim 9, wherein said comparing utilizes a probability test.

44. The method of claim 43, wherein the probability test comprises a $\chi^2$ test.

45. The method of claim 1, wherein the signal environment further includes at least one of the group consisting of a time interval to end of a preceding pulse and a time interval to beginning of an ensuing pulse.

46. The method of claim 45, wherein the characterization of an optical signal preceding the first optical signal is selected from at least one of the group consisting of a basecall, signal intensity, signal duration, pulse shape, and pulse width.

47. The method of claim 1, wherein the characterization of the optical signal preceding the first optical signal is an interpulse distance between the first optical signal and the optical signal preceding the first optical signal.

48. The method of claim 1, wherein the characterization of the optical signal that comes after the first optical signal is an interpulse distance between the first optical signal and the optical signal that comes after the first optical signal.

49. The method of claim 11, wherein the characterization of the optical signal preceding the first optical signal is an interpulse distance between the first optical signal and the optical signal preceding the first optical signal.

50. The method of claim 11, wherein the characterization of the optical signal that comes after the first optical signal is an interpulse distance between the first optical signal and the optical signal that comes after the first optical signal.

51. The method of claim 1, wherein the classifying is performed before the associating.

52. The method of claim 1, wherein the associating is performed before the classifying.

* * * * *